US011458473B2

(12) United States Patent
Linder et al.

(10) Patent No.: US 11,458,473 B2
(45) Date of Patent: *Oct. 4, 2022

(54) SYSTEMS AND DEVICES FOR ANALYSIS OF SAMPLES

(71) Applicant: OPKO Diagnostics, LLC, Woburn, MA (US)

(72) Inventors: Vincent Linder, Tewksbury, MA (US); David Steinmiller, Half Moon Bay, CA (US); Jason Taylor, Windham, NH (US)

(73) Assignee: OPKO Diagnostics, LLC, Woburn, MA (US)

( * ) Notice: Subject to any disclaimer, the term of this patent is extended or adjusted under 35 U.S.C. 154(b) by 488 days.

This patent is subject to a terminal disclaimer.

(21) Appl. No.: 16/564,268

(22) Filed: Sep. 9, 2019

(65) Prior Publication Data

US 2020/0070164 A1 Mar. 5, 2020

Related U.S. Application Data

(60) Continuation of application No. 15/588,548, filed on May 5, 2017, now Pat. No. 10,456,784, which is a
(Continued)

(51) Int. Cl.
*B01L 3/00* (2006.01)
*G01N 21/05* (2006.01)
(Continued)

(52) U.S. Cl.
CPC ....... *B01L 3/502746* (2013.01); *B01L 3/5027* (2013.01); *B01L 3/50273* (2013.01);
(Continued)

(58) Field of Classification Search
CPC .... B01L 3/563; B01L 3/52715; B01L 3/5027; B01L 3/502746; B01L 3/50273;
(Continued)

(56) References Cited

U.S. PATENT DOCUMENTS

| 3,735,640 A | 5/1973 | Chizhov et al. |
| 4,318,994 A | 3/1982 | Meyer et al. |

(Continued)

FOREIGN PATENT DOCUMENTS

| CL | 2805-98 | 9/1999 |
| CN | 101379386 A | 3/2009 |

(Continued)

OTHER PUBLICATIONS

U.S. Appl. No. 15/197,107, filed Jun. 29, 2016, Linder et al.
(Continued)

*Primary Examiner* — Christopher Adam Hixson
(74) *Attorney, Agent, or Firm* — Wolf, Greenfield & Sacks, P.C.

(57) ABSTRACT

Systems and methods for analysis of samples, and in certain embodiments, microfluidic sample analyzers configured to receive a cassette containing a sample therein to perform an analysis of the sample are described. The microfluidic sample analyzers may be used to control fluid flow, mixing, and sample analysis in a variety of microfluidic systems such as microfluidic point-of-care diagnostic platforms. Advantageously, the microfluidic sample analyzers may be, in some embodiments, inexpensive, reduced in size compared to conventional bench top systems, and simple to use. Cassettes that can operate with the sample analyzers are also described.

20 Claims, 27 Drawing Sheets

Related U.S. Application Data continuation of application No. 14/554,205, filed on Nov. 26, 2014, now Pat. No. 9,643,182, which is a division of application No. 13/088,102, filed on Apr. 15, 2011, now Pat. No. 8,932,523.

(60) Provisional application No. 61/363,002, filed on Jul. 9, 2010, provisional application No. 61/325,023, filed on Apr. 16, 2010, provisional application No. 61/325,044, filed on Apr. 16, 2010.

(51) Int. Cl.

| | | |
|---|---|---|
| *G01N 21/59* | (2006.01) | |
| *G01N 21/64* | (2006.01) | |
| *G01N 21/76* | (2006.01) | |
| *G01N 33/543* | (2006.01) | |
| *B01L 7/00* | (2006.01) | |
| *G01N 33/574* | (2006.01) | |

(52) U.S. Cl.
CPC ... *B01L 3/502715* (2013.01); *B01L 3/502738* (2013.01); *G01N 21/05* (2013.01); *G01N 21/59* (2013.01); *G01N 21/64* (2013.01); *G01N 21/76* (2013.01); *G01N 33/54313* (2013.01); *G01N 33/54366* (2013.01); *G01N 33/57434* (2013.01); *B01L 7/52* (2013.01); *B01L 2200/025* (2013.01); *B01L 2200/026* (2013.01); *B01L 2200/027* (2013.01); *B01L 2200/028* (2013.01); *B01L 2200/0673* (2013.01); *B01L 2200/0684* (2013.01); *B01L 2200/143* (2013.01); *B01L 2200/146* (2013.01); *B01L 2200/147* (2013.01); *B01L 2300/021* (2013.01); *B01L 2300/023* (2013.01); *B01L 2300/027* (2013.01); *B01L 2300/04* (2013.01); *B01L 2300/0654* (2013.01); *B01L 2300/0816* (2013.01); *B01L 2300/0867* (2013.01); *B01L 2300/12* (2013.01); *B01L 2300/14* (2013.01); *B01L 2300/16* (2013.01); *B01L 2300/168* (2013.01); *B01L 2300/1827* (2013.01); *B01L 2300/1894* (2013.01); *B01L 2400/049* (2013.01); *B01L 2400/0475* (2013.01); *B01L 2400/0666* (2013.01); *B01L 2400/082* (2013.01); *G01N 2201/02* (2013.01); *G01N 2201/062* (2013.01); *G01N 2201/0612* (2013.01); *G01N 2201/0621* (2013.01); *G01N 2201/0697* (2013.01); *G01N 2333/96433* (2013.01); *Y10T 137/0324* (2015.04); *Y10T 436/12* (2015.01)

(58) Field of Classification Search
CPC .................. B01L 3/502738; B01L 7/52; B01L 2200/025; B01L 2200/026; B01L 2200/028; B01L 2200/0673; B01L 2200/0684; B01L 2200/143; B01L 2200/147; B01L 2200/146; B01L 2300/168; B01L 2300/027; B01L 2300/1827; B01L 2300/1897; B01L 2300/0816; B01L 2300/021; B01L 2300/16; B01L 2300/12; B01L 2300/0654; B01L 2300/023; B01L 2300/14; B01L 2300/0867; B01L 2300/04; B01L 2400/049; B01L 2400/082; B01L 2400/0475; B01L 2400/0666

See application file for complete search history.

(56) References Cited

U.S. PATENT DOCUMENTS

| | | |
|---|---|---|
| 4,517,302 A | 5/1985 | Saros |
| 4,534,465 A | 8/1985 | Rothermel et al. |
| 4,919,887 A | 4/1990 | Wakatake |
| 4,963,498 A | 10/1990 | Hillman et al. |
| 5,051,237 A | 9/1991 | Grenner et al. |
| 5,219,762 A | 6/1993 | Katamine et al. |
| 5,268,147 A | 12/1993 | Zabetakis et al. |
| 5,279,791 A | 1/1994 | Aldrich et al. |
| 5,286,454 A | 2/1994 | Nilsson et al. |
| 5,376,252 A | 12/1994 | Ekström et al. |
| 5,478,751 A | 12/1995 | Oosta et al. |
| 5,486,335 A | 1/1996 | Wilding et al. |
| 5,540,081 A | 7/1996 | Takeda et al. |
| 5,571,410 A | 11/1996 | Swedberg et al. |
| 5,585,069 A | 12/1996 | Zanzucchi et al. |
| 5,635,358 A | 6/1997 | Wilding et al. |
| 5,637,469 A | 6/1997 | Wilding et al. |
| 5,638,828 A | 6/1997 | Lauks et al. |
| 5,726,026 A | 3/1998 | Wilding et al. |
| 5,731,212 A | 3/1998 | Gavin et al. |
| 5,866,345 A | 2/1999 | Wilding et al. |
| 5,876,675 A | 3/1999 | Kennedy |
| 5,916,524 A | 6/1999 | Tisone |
| 5,932,799 A | 8/1999 | Moles |
| 5,942,443 A | 8/1999 | Parce et al. |
| 5,955,028 A | 9/1999 | Chow |
| 5,957,579 A | 9/1999 | Kopf-Sill et al. |
| 6,001,231 A | 12/1999 | Kopf-Sill |
| 6,019,944 A | 2/2000 | Buechler |
| 6,042,709 A | 3/2000 | Parce et al. |
| 6,046,056 A | 4/2000 | Parce et al. |
| 6,073,482 A | 6/2000 | Moles |
| 6,103,199 A | 8/2000 | Bjornson et al. |
| 6,114,122 A | 9/2000 | Besemer et al. |
| 6,136,272 A | 10/2000 | Weigl et al. |
| 6,146,489 A | 11/2000 | Wirth |
| 6,146,589 A | 11/2000 | Chandler |
| 6,168,948 B1 | 1/2001 | Anderson et al. |
| 6,176,962 B1 | 1/2001 | Soane et al. |
| 6,184,029 B1 | 2/2001 | Wilding et al. |
| 6,186,660 B1 | 2/2001 | Kopf-Sill et al. |
| 6,190,616 B1 | 2/2001 | Jovanovich et al. |
| 6,207,369 B1 | 3/2001 | Wohlstadter et al. |
| 6,214,560 B1 | 4/2001 | Yguerabide et al. |
| 6,238,538 B1 | 5/2001 | Parce et al. |
| 6,241,560 B1 | 6/2001 | Furusawa et al. |
| 6,251,343 B1 | 6/2001 | Dubrow et al. |
| 6,274,337 B1 | 8/2001 | Parce et al. |
| 6,293,012 B1 | 9/2001 | Moles |
| 6,296,020 B1 | 10/2001 | McNeely et al. |
| 6,331,439 B1 | 12/2001 | Cherukuri et al. |
| 6,333,200 B1 | 12/2001 | Kaler et al. |
| 6,353,475 B1 | 3/2002 | Jensen et al. |
| 6,361,958 B1 | 3/2002 | Shieh et al. |
| 6,413,782 B1 | 7/2002 | Parce et al. |
| 6,416,642 B1 | 7/2002 | Alajoki et al. |
| 6,429,025 B1 | 8/2002 | Parce et al. |
| 6,432,720 B2 | 8/2002 | Chow |
| 6,479,299 B1 | 11/2002 | Parce et al. |
| 6,488,872 B1 | 12/2002 | Beebe et al. |
| 6,488,894 B1 | 12/2002 | Miethe et al. |
| 6,488,896 B2 | 12/2002 | Weigl et al. |
| 6,495,104 B1 | 12/2002 | Unno et al. |
| 6,549,275 B1 | 4/2003 | Cabuz et al. |
| 6,551,841 B1 | 4/2003 | Wilding et al. |
| 6,561,208 B1 | 5/2003 | O'Connor et al. |
| 6,610,499 B1 | 8/2003 | Fulwyler et al. |
| 6,613,512 B1 | 9/2003 | Kopf-Sill et al. |
| 6,613,525 B2 | 9/2003 | Nelson et al. |
| 6,620,625 B2 | 9/2003 | Wolk et al. |
| 6,632,619 B1 | 10/2003 | Harrison et al. |
| 6,638,482 B1 | 10/2003 | Ackley et al. |
| 6,656,430 B2 | 12/2003 | Sheppard, Jr. et al. |
| 6,656,431 B2 | 12/2003 | Holl et al. |
| 6,669,831 B2 | 12/2003 | Chow et al. |

(56) References Cited

U.S. PATENT DOCUMENTS

| | | |
|---|---|---|
| 6,705,357 B2 | 3/2004 | Jeon et al. |
| 6,709,869 B2 | 3/2004 | Mian et al. |
| 6,716,620 B2 | 4/2004 | Bashir et al. |
| 6,742,661 B1 | 6/2004 | Schulte et al. |
| 6,761,962 B2 | 7/2004 | Bentsen et al. |
| 6,780,584 B1 | 8/2004 | Edman et al. |
| 6,794,197 B1 | 9/2004 | Indermuhle et al. |
| 6,818,184 B2 | 11/2004 | Fulwyler et al. |
| 6,827,095 B2 | 12/2004 | O'Connor et al. |
| 6,828,143 B1 | 12/2004 | Bard |
| 6,830,936 B2 | 12/2004 | Anderson et al. |
| 6,858,185 B1 | 2/2005 | Kopf-Sill et al. |
| 6,875,403 B2 | 4/2005 | Liu et al. |
| 6,878,271 B2 | 4/2005 | Gilbert et al. |
| 6,878,755 B2 | 4/2005 | Singh et al. |
| 6,906,797 B1 | 6/2005 | Kao et al. |
| 6,919,045 B1 | 7/2005 | Berndt |
| 6,925,392 B2 | 8/2005 | McNeil, II et al. |
| 6,949,377 B2 | 9/2005 | Ho |
| 6,953,550 B2 | 10/2005 | Sheppard, Jr. et al. |
| 6,982,787 B1 | 1/2006 | Wapner et al. |
| 6,987,263 B2 | 1/2006 | Hobbs et al. |
| 6,989,128 B2 | 1/2006 | Alajoki et al. |
| 7,005,292 B2 | 2/2006 | Wilding et al. |
| 7,010,391 B2 | 3/2006 | Handique et al. |
| 7,015,046 B2 | 3/2006 | Wohlstadter et al. |
| 7,018,830 B2 | 3/2006 | Wilding et al. |
| 7,067,263 B2 | 6/2006 | Parce et al. |
| 7,087,148 B1 | 8/2006 | Blackburn et al. |
| 7,091,048 B2 | 8/2006 | Parce et al. |
| 7,275,682 B2 | 10/2007 | Excoffier et al. |
| 7,611,616 B2 | 11/2009 | Cohen et al. |
| 7,943,386 B2 | 5/2011 | Grumann et al. |
| 8,030,057 B2 | 10/2011 | Linder et al. |
| 8,202,492 B2 | 6/2012 | Linder et al. |
| 8,221,700 B2 | 7/2012 | Steinmiller et al. |
| 8,222,049 B2 | 7/2012 | Linder et al. |
| 8,389,272 B2 | 3/2013 | Linder et al. |
| 8,409,527 B2 | 4/2013 | Linder et al. |
| 8,475,737 B2 | 7/2013 | Linder et al. |
| 8,480,975 B2 | 7/2013 | Steinmiller et al. |
| 8,567,425 B2 | 10/2013 | Tan et al. |
| 8,580,569 B2 | 11/2013 | Linder et al. |
| 8,591,829 B2 | 11/2013 | Taylor et al. |
| 8,765,062 B2 | 7/2014 | Linder et al. |
| 8,802,029 B2 | 8/2014 | Steinmiller et al. |
| 8,802,445 B2 | 8/2014 | Linder et al. |
| 8,915,259 B2 | 12/2014 | Tan et al. |
| 8,932,523 B2 | 1/2015 | Linder et al. |
| 9,075,047 B2 | 7/2015 | Linder et al. |
| 9,075,051 B2 | 7/2015 | Tan et al. |
| 9,116,124 B2 | 8/2015 | Linder et al. |
| 9,234,888 B2 | 1/2016 | Linder et al. |
| 9,555,408 B2 | 1/2017 | Tan et al. |
| 9,561,506 B2 | 2/2017 | Taylor et al. |
| 9,592,505 B2 | 3/2017 | Linder et al. |
| 9,643,182 B2 | 5/2017 | Linder et al. |
| 9,682,376 B2 | 6/2017 | Linder et al. |
| 9,731,291 B2 | 8/2017 | Tan et al. |
| 9,770,715 B2 | 9/2017 | Steinmiller et al. |
| 9,795,697 B2 | 10/2017 | Linder et al. |
| 9,827,563 B2 | 11/2017 | Steinmiller et al. |
| 9,827,564 B2 | 11/2017 | Steinmiller et al. |
| 9,849,455 B2 | 12/2017 | Linder et al. |
| 9,861,980 B2 | 1/2018 | Tan et al. |
| 9,878,324 B2 | 1/2018 | Taylor et al. |
| 9,981,266 B2 | 5/2018 | Linder et al. |
| 10,456,784 B2 | 10/2019 | Linder et al. |
| 2001/0027918 A1 | 10/2001 | Parce et al. |
| 2001/0048637 A1 | 12/2001 | Weigl et al. |
| 2002/0001818 A1 | 1/2002 | Brock |
| 2002/0019059 A1 | 2/2002 | Chow et al. |
| 2002/0054835 A1 | 5/2002 | Robotti et al. |
| 2002/0071788 A1 | 6/2002 | Fujii et al. |
| 2002/0092767 A1 | 7/2002 | Bjornson et al. |
| 2002/0142618 A1 | 10/2002 | Parce et al. |
| 2002/0199094 A1 | 12/2002 | Strand et al. |
| 2003/0012697 A1 | 1/2003 | Hahn et al. |
| 2003/0082081 A1 | 5/2003 | Fouillet et al. |
| 2003/0118486 A1 | 6/2003 | Zhou et al. |
| 2003/0124623 A1 | 7/2003 | Yager et al. |
| 2003/0138969 A1 | 7/2003 | Jakobsen et al. |
| 2003/0207328 A1 | 11/2003 | Yguerabide et al. |
| 2004/0077074 A1 | 4/2004 | Ackley et al. |
| 2004/0115094 A1 | 6/2004 | Gumbrecht et al. |
| 2004/0195728 A1 | 10/2004 | Slomski et al. |
| 2004/0228771 A1 | 11/2004 | Zhou et al. |
| 2005/0014248 A1 | 1/2005 | Canton |
| 2005/0019902 A1 | 1/2005 | Mathies et al. |
| 2005/0026300 A1 | 2/2005 | Samper et al. |
| 2005/0118061 A1 | 6/2005 | Mototsu et al. |
| 2005/0118073 A1 | 6/2005 | Facer et al. |
| 2005/0161669 A1 | 7/2005 | Jovanovich et al. |
| 2005/0221281 A1 | 10/2005 | Ho |
| 2005/0238545 A1 | 10/2005 | Parce et al. |
| 2005/0243304 A1 | 11/2005 | Padmanabhan et al. |
| 2005/0255003 A1 | 11/2005 | Summersgill et al. |
| 2006/0002827 A1 | 1/2006 | Curcio et al. |
| 2006/0013740 A1 | 1/2006 | Berndtson et al. |
| 2006/0046300 A1 | 3/2006 | Padmanabhan et al. |
| 2006/0076482 A1 | 4/2006 | Hobbs et al. |
| 2006/0094119 A1 | 5/2006 | Ismagilov et al. |
| 2006/0172425 A1 | 8/2006 | Neigl et al. |
| 2006/0202133 A1 | 9/2006 | Ok et al. |
| 2006/0210435 A1 | 9/2006 | Alavie et al. |
| 2006/0257290 A1 | 11/2006 | Shimizu |
| 2006/0257941 A1 | 11/2006 | McDevitt et al. |
| 2006/0257992 A1 | 11/2006 | McDevitt et al. |
| 2006/0263888 A1 | 11/2006 | Fritz et al. |
| 2006/0275852 A1 | 12/2006 | Montagu |
| 2007/0003434 A1 | 1/2007 | Padmanabhan et al. |
| 2007/0009386 A1 | 1/2007 | Padmanabhan et al. |
| 2007/0031289 A1 | 2/2007 | Cox et al. |
| 2007/0048189 A1 | 3/2007 | Cox et al. |
| 2007/0075010 A1 | 4/2007 | Gilbert et al. |
| 2007/0116598 A1 | 5/2007 | Hughes et al. |
| 2007/0120903 A1 | 5/2007 | Takagi |
| 2007/0148039 A1 | 6/2007 | Padmanabhan et al. |
| 2007/0166195 A1 | 7/2007 | Padmanabhan et al. |
| 2007/0172388 A1 | 7/2007 | Padmanabhan et al. |
| 2007/0298433 A1 | 12/2007 | Sia et al. |
| 2008/0085219 A1 | 4/2008 | Beebe et al. |
| 2008/0107565 A1 | 5/2008 | Vivienne et al. |
| 2008/0248590 A1 | 10/2008 | Gulliksen et al. |
| 2008/0273918 A1 | 11/2008 | Linder et al. |
| 2008/0280365 A1 | 11/2008 | Grumann et al. |
| 2009/0022625 A1 | 1/2009 | Lee et al. |
| 2009/0075390 A1 | 3/2009 | Linder et al. |
| 2009/0137029 A1 | 5/2009 | Breidenthal et al. |
| 2009/0156966 A1 | 6/2009 | Kontschieder et al. |
| 2009/0266421 A1 | 10/2009 | Linder et al. |
| 2010/0008834 A1 | 1/2010 | Lohf et al. |
| 2010/0027008 A1 | 2/2010 | Bornhop et al. |
| 2010/0047774 A1 | 2/2010 | Van Haag et al. |
| 2010/0093105 A1 | 4/2010 | Lee et al. |
| 2010/0158756 A1 | 6/2010 | Taylor et al. |
| 2010/0196207 A1 | 8/2010 | Steinmiller et al. |
| 2011/0120562 A1 | 5/2011 | Tan et al. |
| 2011/0253224 A1 | 10/2011 | Linder et al. |
| 2011/0256551 A1 | 10/2011 | Linder et al. |
| 2012/0237401 A1 | 9/2012 | Steinmiller et al. |
| 2012/0238033 A1 | 9/2012 | Linder et al. |
| 2012/0241013 A1 | 9/2012 | Linder et al. |
| 2012/0269701 A1 | 10/2012 | Linder et al. |
| 2013/0157286 A1 | 6/2013 | Linder et al. |
| 2013/0224075 A1 | 8/2013 | Linder et al. |
| 2013/0236375 A1 | 9/2013 | Tan et al. |
| 2013/0252321 A1 | 9/2013 | Steinmiller et al. |
| 2014/0023565 A1 | 1/2014 | Taylor et al. |
| 2014/0038166 A1 | 2/2014 | Linder et al. |
| 2014/0093866 A1 | 4/2014 | Tan et al. |
| 2014/0205997 A1 | 7/2014 | Linder et al. |
| 2014/0234180 A1 | 8/2014 | Linder et al. |
| 2015/0044760 A1 | 2/2015 | Tan et al. |

(56) References Cited

U.S. PATENT DOCUMENTS

| | | | |
|---|---|---|---|
| 2015/0079606 A1 | 3/2015 | Linder et al. |
| 2015/0086997 A1 | 3/2015 | Linder et al. |
| 2015/0196908 A9 | 7/2015 | Steinmiller et al. |
| 2015/0251178 A1 | 9/2015 | Tan et al. |
| 2015/0343443 A1 | 12/2015 | Linder et al. |
| 2016/0077087 A1 | 3/2016 | Linder et al. |
| 2016/0305878 A1 | 10/2016 | Steinmiller et al. |
| 2016/0305937 A1 | 10/2016 | Steinmiller et al. |
| 2016/0305938 A1 | 10/2016 | Linder et al. |
| 2017/0165661 A1 | 6/2017 | Taylor et al. |
| 2017/0165664 A1 | 6/2017 | Tan et al. |
| 2017/0165665 A1 | 6/2017 | Linder et al. |
| 2017/0239656 A1 | 8/2017 | Linder et al. |
| 2017/0304822 A1 | 10/2017 | Tan et al. |
| 2018/0071735 A1 | 3/2018 | Linder et al. |
| 2018/0078938 A1 | 3/2018 | Tan et al. |
| 2018/0085753 A1 | 3/2018 | Steinmiller et al. |
| 2018/0099272 A1 | 4/2018 | Taylor et al. |
| 2018/0236448 A1 | 8/2018 | Linder et al. |

FOREIGN PATENT DOCUMENTS

| | | |
|---|---|---|
| DE | 10115474 A1 | 10/2002 |
| EP | 0 110 771 B1 | 3/1988 |
| EP | 0 643 307 A1 | 3/1995 |
| EP | 1 054 259 A1 | 11/2000 |
| EP | 1 542 000 A1 | 6/2005 |
| EP | 1 898 210 A2 | 3/2008 |
| EP | 1 946 830 A1 | 7/2008 |
| EP | 2 071 026 A1 | 6/2009 |
| JP | 2003-531018 A | 10/2003 |
| JP | 2005-106669 A | 4/2005 |
| JP | 2006-038726 A | 2/2006 |
| JP | 2006-308428 A | 11/2006 |
| JP | 2007-017354 A | 1/2007 |
| JP | 2009-115729 A | 5/2009 |
| JP | 2009-229263 A | 10/2009 |
| JP | 2009-257988 A | 11/2009 |
| JP | 2009-282041 A | 12/2009 |
| RU | 2005107721 A | 9/2005 |
| WO | WO 91/01003 A | 1/1991 |
| WO | WO 95/26796 A1 | 10/1995 |
| WO | WO 96/14934 A1 | 5/1996 |
| WO | WO 97/06437 A1 | 2/1997 |
| WO | WO 00/72970 A1 | 12/2000 |
| WO | WO 02/22250 A2 | 3/2002 |
| WO | WO 03/054513 A2 | 7/2003 |
| WO | WO 2004/022233 A1 | 3/2004 |
| WO | WO 2004/061418 A2 | 7/2004 |
| WO | WO 2004/087951 A3 | 10/2004 |
| WO | WO 2004/105946 A2 | 12/2004 |
| WO | WO 2005/056186 A1 | 6/2005 |
| WO | WO 2005/072858 | 8/2005 |
| WO | WO 2006/018044 A1 | 2/2006 |
| WO | WO 2006/056787 A1 | 6/2006 |
| WO | WO 2006/103440 A2 | 10/2006 |
| WO | WO 2006/113727 A2 | 10/2006 |
| WO | WO 2007/082480 A1 | 7/2007 |
| WO | WO 2007/097257 A1 | 8/2007 |
| WO | WO 2008/005248 A2 | 1/2008 |
| WO | WO 2008/028124 A1 | 3/2008 |
| WO | WO 2008/118098 A1 | 10/2008 |
| WO | WO 2008/123112 A1 | 10/2008 |
| WO | WO 2008/137008 A2 | 11/2008 |

OTHER PUBLICATIONS

U.S. Appl. No. 15/787,078, filed Oct. 18, 2017, Steinmiller et al.
U.S. Appl. No. 15/840,159, filed Dec. 13, 2017, Taylor et al.
U.S. Appl. No. 15/828,999, filed Dec. 1, 2017, Tan et al.
U.S. Appl. No. 15/957,023, filed Apr. 19, 2018, Linder et al.
PCT/US2011/032680, Sep. 23, 2011, International Search Report and Written Opinion.
PCT/US2011/032680, Oct. 26, 2012, International Preliminary Report on Patentability.
International Search Report and Written Opinion for PCT/US2011/032680 dated Sep. 23, 2011.
International Preliminary Report on Patentability for PCT/US2011/032680 dated Oct. 26, 2012.
International Search Report and Written Opinion for PCT/US2011/032685 dated Sep. 23, 2011.
International Preliminary Report on Patentability for PCT/US2011/032685 dated Oct. 26, 2012.
[No Author Listed] Proceedings of uTAS 2004, 8th International Conference on Miniaturized Systems in Chemistry and Life Sciences, Sep. 26-30, Malmo, Sweden, Edited by Thomas Laurell, Johan Nilsson, Klavs Jensen, D. Jed Harrison, Jorg P. Kutter, The Royal Society of Chemistry, pp. 1-135 (2004).
Ahn et al., Disposable Smart Lab on a Chip for Point-of-Care Clinical Diagnostics. Proceedings of the IEEE. 2004;92(1): 154-73.
Andersson, et al., Micromachined flow-through filter-chamber for chemical reactions on beads. Sensors and Actuators B. 2000;67:203-08.
Atencia et al., Capillary inserts in microcirculatory systems. Lab Chip. 2006;6: 575-77.
Atencia et al., Steady flow generation in microcirculatory systems. Lab Chip. 2006;6:567-74.
Daridon, et al., Chemical sensing using an integrated microfluidic system based on the Berthelot reaction. Sensors and Actuators B. 2001;76:235-43.
Dodge, et al., Electrokinetically Driven Microfluidic Chips with Surface-Modified Chambers for Heterogeneous Immunoassays. Anal Chem. 2001;73:3400-09.
Fredrickson et al., Macro-to-micro interfaces for microfluidic devices. Lab Chip. 2004;4:526-33.
Gray et al., Interlocking mechanical and fluidic interconnections for micro fluidic circuit boards. Sensors and Actuators A. 2004;112:18-24.
Grodzinski et al., A Modular Microfluidic System for Cell Pre-concentration and Genetic Sample Preparation. Biomedical Microdevices. 2003;5(4):303-10.
Juncker et al., Autonomous Microfluidic Capillary Systems. Anal Chem. 2002;74:6139-44.
Linder, et al., Reagent-Loaded Cartridges for Valveless and Automated Fluid Delivery in Microfluidic Devices. Anal Chem. 2005;77(1):64-71.
Moorthy, et al., Microfluidic tectonics platform: A colorimetric, disposable botulinum toxin enzyme-linked immunosorbent assay system. Electrophoresis. 2004;25:1705-13.
Obeid et al., Microfabricated Device for DNA and RNA Amplification by Continuous-Flow Polymerase Chain Reaction and Reverse Transcription-Polymerase Chain Reaction with Cycle Number Selection. Anal Chem. 2003;75:288-95.
Sia et al., An Integrated Approach to a Portable and Low-Cost Immunoassay for Resource-Poor Settings. Angew Chem Int Ed. 2004;43:498-502.
Sia et al., Microfluidic devices fabricated in poly(dimethlysiloxane) for biological studies. Electrophoresis. 2003;24:3563-76.
Song et al., A microfluidic system for controlling reaction networks in time. Angew Chem Int Ed. 2003;42(7):768-72.
Weigl et al., Lab-on-a-chip for drug development. Advanced Drug Delivery Reviews. 2003;55:349-77.
Sabourin et al., One-step fabrication of microfluidic chips with in-plane, adhesive-free interconnections. Journal of Micromechanics and Microengineering. Feb. 2010;20(3):037001. 7 pages.

SYSTEMS AND DEVICES FOR ANALYSIS OF SAMPLES

RELATED APPLICATIONS

The present application is a continuation of U.S. patent application Ser. No. 15/588,548, filed May 5, 2017 and entitled "Systems and Devices for Analysis of Samples," which is a continuation of U.S. patent application Ser. No. 14/554,205, filed Nov. 26, 2014 and entitled "Systems and Devices for Analysis of Samples," which is a division of U.S. patent application Ser. No. 13/088,102, filed Apr. 15, 2011 and entitled "Systems and Devices for Analysis of Samples," which claims priority under 35 U.S.C. § 119(e) to U.S. provisional applications: U.S. Ser. No. 61/325,023, filed Apr. 16, 2010 and entitled "Feedback Control in Microfluidic Systems", U.S. Ser. No. 61/325,044, filed Apr. 16, 2010 and entitled "Feedback Control in Microfluidic Systems", and U.S. Ser. No. 61/363,002, filed Jul. 9, 2010 and entitled "Systems and Devices for Analysis of Samples", each of which is incorporated herein by reference in its entirety.

FIELD

The present application relates generally to systems, devices and methods for analysis of samples, and in certain embodiments, to microfluidic sample analyzers configured to receive a cassette having a sample therein to analyze the sample. Cassettes for sample analysis are also provided.

BACKGROUND

The manipulation of fluids plays an important role in fields such as chemistry, microbiology and biochemistry. These fluids may include liquids or gases and may provide reagents, solvents, reactants, or rinses to chemical or biological processes. While various microfluidic methods and cassettes, such as microfluidic assays, can provide inexpensive, sensitive and accurate analytical platforms, fluid manipulations—such as sample introduction, introduction of reagents, storage of reagents, control of fluid flow, separation of fluids, mixing of multiple fluids, collection of waste, extraction of fluids for off-chip analysis, and/or transfer of fluids from one chip to the next—can add a level of cost and sophistication. Often, a microfluidic cassette requires an external platform such as an analyzer to perform some such and other fluid manipulations. Various types of analyzers exist to process and analyze a microfluidic sample, however, some such analyzers are expensive, bulky, difficult to use, and/or require complex components for manipulating fluids. Accordingly, advances in the field that could reduce costs, reduce size, simplify use, reduce complexity of components required for fluid manipulations, and/or improve fluid manipulations in microfluidic systems would be beneficial.

SUMMARY

Systems and methods for analysis of samples are described. The subject matter of the present invention involves, in some cases, interrelated products, alternative solutions to a particular problem, and/or a plurality of different uses of one or more systems and/or articles.

In one set of embodiments, a series of methods are provided. In one embodiment, a method of analyzing a microfluidic sample comprises the steps of providing a microfluidic sample analyzer comprising a housing with an opening therein, wherein a cassette is contained in the opening in the housing and, wherein the cassette or a component of the cassette includes at least one channel with a fluid sample therein. The method includes identifying information about the cassette with an identification reader positioned within the housing, and processing information input by a user into a user interface positioned within the housing of the sample analyzer. The method also involves pressurizing the at least one channel in the cassette with a pressure-control system positioned within the housing to move the sample through the at least one channel. The method includes activating an optical system that passes light from a first light source positioning within the housing through a first measurement zone of the cassette, and detecting the amount of light transmission through the first measurement zone of the cassette with a first detector of the optical system positioned within the housing opposite the first light source. The method involves analyzing the sample in the cassette with a control system positioned within the housing which communicates with the identification reader, the user interface, the pressure-control system, the optical system and the temperature regulating system. The method may optionally include heating the cassette with a temperature regulating system positioned within the housing of the sample analyzer.

In another set of embodiments, a series of microfluidic sample analyzers are provided. In one embodiment, a microfluidic sample analyzer comprises a housing, an opening in the housing configured to receive a cassette having at least one channel with a fluid sample therein, wherein the housing includes a component configured to interface with a mating component on the cassette to detect the cassette within the housing, and an identification reader positioned within the housing and configured to read information associated with the cassette. The microfluidic sample analyzer also includes a user interface positioned within the housing and configured for a user to input information into the sample analyzer, and a pressure-control system positioned within the housing, the pressure-control system configured to pressurize the at least one channel in the cassette to move the sample through the at least one channel. The microfluidic sample analyzer further includes an optical system positioned within the housing, the optical system including at least a first light source and a first detector spaced apart from the first light source, wherein the first light source is configured to pass light through a first measurement zone of a cassette when inserted into the sample analyzer and wherein the first detector is positioned opposite the first light source to detect the amount of light transmission through the first measurement zone of the cassette. The microfluidic sample analyzer also includes a temperature regulating system positioned within the housing, the temperature regulating system including a heater configured to heat the cassette, and a control system positioned within the housing and configured to communicate with the identification reader, the user interface, the pressure-control system, the optical system and the temperature regulating system, to analyze the sample in the cassette.

In another embodiment, a microfluidic sample analyzer comprises a housing, and an opening in the housing configured to receive a cassette having at least one channel with a fluid sample therein and at least one microfluidic channel having a cross-sectional dimension of less than 1 mm, wherein the housing includes a component configured to interface with a mating component on the cassette to detect the cassette within the housing. The microfluidic sample analyzer includes a pressure-control system positioned within the housing, the pressure-control system configured to pressurize the at least one channel in the cassette to move the sample through the at least one channel, and an optical system positioned within the housing, the optical system including a plurality of light sources and a plurality of detectors spaced apart from the plurality of light sources, wherein the light sources are configured to pass light through the cassette when the cassette is inserted into the sample analyzer and wherein the detectors are positioned opposite the light sources to detect the amount of light that passes through the cassette. The plurality of light sources includes at least a first light source and a second light source adjacent the first light source, wherein the first light source is configured to pass light through a first measurement zone of the cassette and the second light source is configured to pass light through a second measurement zone of the cassette adjacent the first measurement zone. In some embodiments, the light sources are configured such that second light source is not activated unless the first light source is deactivated.

In another embodiment, a microfluidic sample analyzer comprises a housing, and an opening in the housing configured to receive a cassette having at least one channel with a fluid sample therein. The microfluidic sample analyzer further includes a spring loaded arm positioned within the housing that has a first position where the arm extends at least partially across the opening in the housing such that as a cassette is inserted into the opening in the housing, the spring loaded arm is pushed away from the opening into a second position, and wherein the spring loaded arm is configured to contact a side surface of the cassette as the cassette is inserted into the housing until the spring loaded arm engages an inwardly cammed surface in the cassette that is configured such that the spring loaded arm returns towards the first position where it extends at least partially across the opening in the housing to retain the cassette within the housing.

In another embodiment, a series of microfluidic sample cassettes are provided. In one embodiment, a microfluidic sample cassette comprises a housing comprising at least one microfluidic channel extending through at least a portion of the housing, wherein the channel is configured to receive a sample therein. The housing comprises at least one surface configured to interact with a microfluidic sample analyzer such that the sample cassette may be inserted into and retained within the sample analyzer, the at least one surface of the housing comprising a curved corner surface configured to contact an arm within the sample analyzer, and a notch configured to retain the arm of the sample analyzer.

In one set of embodiments, a kit is provided. The kit includes a first component comprising a first channel in a first material, the first channel including an inlet, an outlet and, between the first channel inlet and outlet, at least one portion having a cross-sectional dimension greater than 200 microns. The kit also includes a second component comprising a second channel in a second material, the second channel including an inlet, an outlet and, between the second channel inlet and outlet, at least one portion having a cross-sectional dimension less than 200 microns. In some embodiments, the first material is different from the second material (although in other embodiments, the first material may be the same as the second material). In some embodiments, the first material has a water vapor permeability of less than about 0.05 g·mm/mm$^2$·d. In certain embodiments, the second material has an optical transmission of greater than 90% between 400 nm and 800 nm wavelengths of light.

The kit also includes a fluidic connector for fluidly connecting the first and second channels, the fluidic connector comprising a fluid path including a fluid path inlet and a fluid path outlet. The fluid path inlet can be fluidly connected to the outlet of the first channel and the fluid path outlet can be fluidly connected to the inlet of the second channel. The kit is packaged such that the fluidic connector is not fluidically connecting the first and second channels.

In another set of embodiments, a device is provided. The device includes a first component comprising a first channel formed in a first material and including at least one inlet and one outlet, the first channel including at least one portion having a cross-sectional dimension greater than 200 microns. The device also includes a second component comprising a second channel formed in a second material and including at least one inlet and one outlet, the second channel including at least one portion having a cross-sectional dimension less than 200 microns. In some embodiments, the first material is different from the second material (although in other embodiments, the first material may be the same as the second material). In some embodiments, the first material has a water vapor permeability of less than about 0.05 g·mm/mm$^2$·d. In certain embodiments, the second material has an optical transmission of greater than 90% between 400 nm and 800 nm wavelengths of light. The device also includes a fluidic connector that can be connected to the first and second components, the fluid connector comprising a fluid path including a fluid path inlet and a fluid path outlet, wherein upon connection, the fluid path inlet fluidically connects to the outlet of the first channel and the fluid path outlet fluidically connects to the inlet of the second channel to allow fluid communication between the first and second channel. The first and second channels are not in fluid communication with one another prior to first use, and at first use, the first and second channels are brought into fluid communication with one another.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

The accompanying drawings are not intended to be drawn to scale. In the drawings, each identical or nearly identical component that is illustrated in various figures is typically represented by a like descriptor. For purposes of clarity, not every component may be labeled in every drawing.

Various embodiments will now be described, by way of example, with reference to the accompanying drawings, in which.

DETAILED DESCRIPTION

Figure 1A:
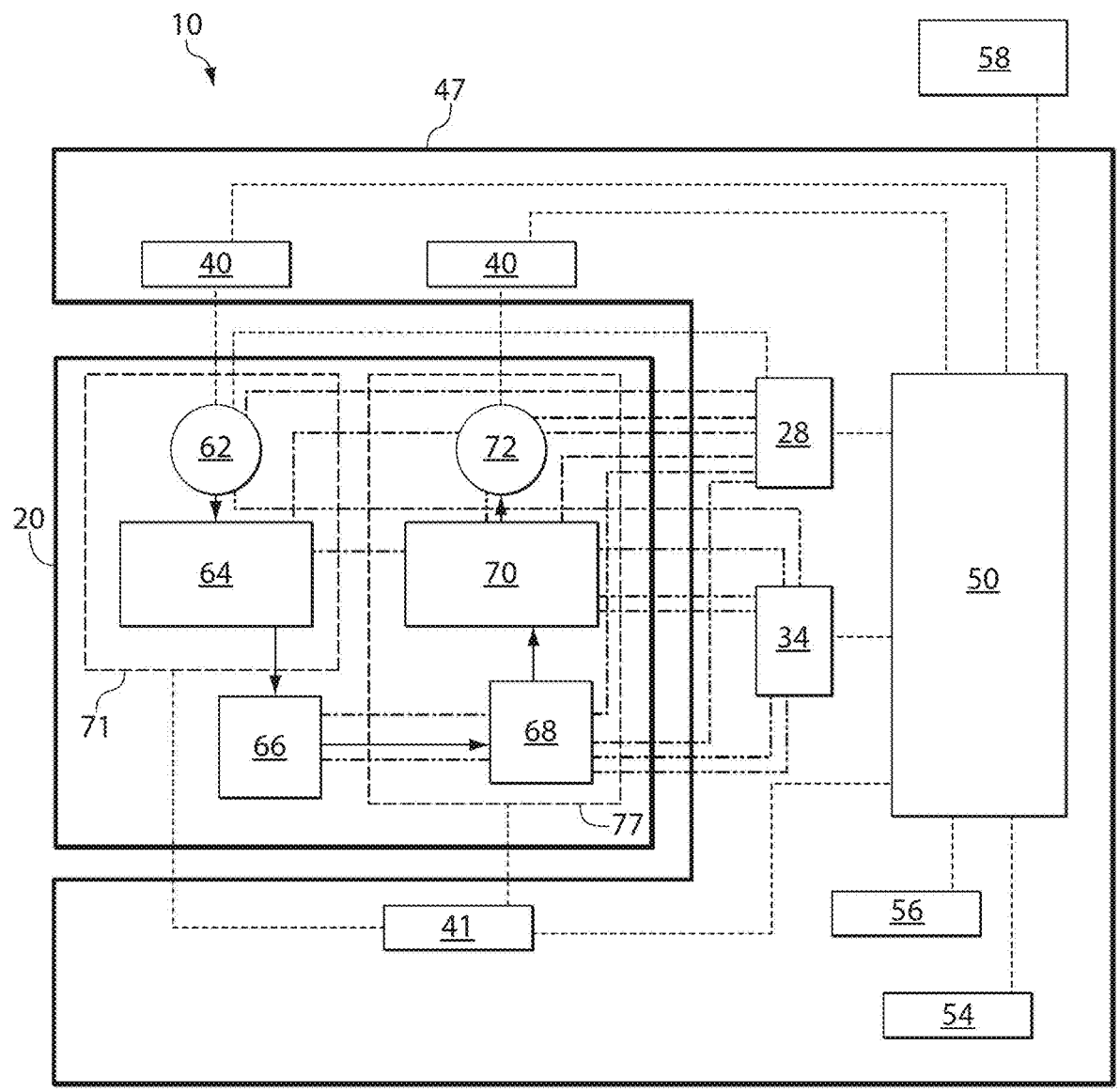
FIG. 1A is a block diagram showing a microfluidic system and a variety of components that may be part of a sample analyzer according to one embodiment.

Systems and methods for analysis of samples, and in certain embodiments, microfluidic sample analyzers configured to receive a cassette containing a sample therein to perform an analysis of the sample are described.

Applicant recognized the need for a unique microfluidic sample analyzer which may be configured to process a sample to measure the level of one or more analytes (e.g., a prostate specific antigen (PSA)) in the sample. As set forth below, measuring the PSA level or level of other analytes in a blood sample may help manage prostate cancer or other disease and/or conditions.

Microfluidic sample analyzers described herein may also be configured and used to process a sample for other reasons, as the invention is not limited to a particular application. For example, in one embodiment, the microfluidic sample analyzers discussed herein may be configured for various types of protein analysis and and/or DNA and/or RNA analysis. In some cases, the systems and methods described herein can be used to control fluid flow and mixing in a variety of microfluidic systems such as, for example, microfluidic point-of-care diagnostic platforms, microfluidic laboratory chemical analysis systems, fluidic control systems in cell cultures or bio-reactors, among others. In one embodiment, the microfluidic sample analyzer is configured for various types of hematology and/or urology applications. The microfluidic sample analyzers discussed herein may be configured for a wide variety of diagnostics and general chemical and/or biological analysis. The sample analyzer may be specifically configured for a particular application and/or may be configured to analyze a sample according to a variety of the applications discussed above and herein.

As set forth in more detail below, the microfluidic sample analyzer may be configured to receive a cassette which includes at least one channel with a sample contained therein. The sample cassette may be configured to be a disposable component that is discarded after the sample is analyzed.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, published as U.S. Patent Publication No. 2008/0273918, filed May 1, 2008 and entitled "Fluidic Connectors and Microfluidic Systems"; U.S. patent application Ser. No. 12/196,392, published as U.S. Patent Publication No. 2009/0075390, filed Aug. 22, 2008, entitled "Liquid containment for integrated assays"; U.S. patent application Ser. No. 12/428,372, filed Apr. 22, 2009, published as U.S. Patent Publication No. 2009/0266421, entitled "Flow Control in Microfluidic Systems"; U.S. patent application Ser. No. 12/640,420, published as U.S. Patent Publication No. 2010/0158756, filed Dec. 17, 2009, entitled, "Reagent Storage in Microfluidic Systems and Related Articles and Methods"; U.S. patent application Ser. No. 12/698,451, filed Feb. 2, 2010, entitled, "Structures for Controlling Light Interaction with Microfluidic Devices"; U.S. Patent Apl. Ser. No. 61/263,981, filed Nov. 14, 2009 and entitled, "Fluid Mixing and Delivery in Microfluidic Systems; U.S. Provisional Patent Application No. 61/325,044, filed Apr. 16, 2010 entitled, "System for Analysis of Samples"; and U.S. Provisional Patent Application No. 61/325,023, filed Apr. 16, 2010 entitled, "Feedback Control in Microfluidic Systems", each of which is incorporated herein by reference in its entirety for all purposes.

A series of exemplary systems and methods are now described.

FIG. 1A shows a block diagram 10 of a microfluidic system and various components that may provide feedback control according to one set of embodiments. The microfluidic system may include, for example, a cassette 20 operatively associated with one or more components such as a fluid flow source 40 such as a pump (e.g., for introducing one or more fluids into the cassette and/or for controlling the rates of fluid flow), optionally a fluid flow source 40 such as a pump or vacuum that may be configured to apply either of both of a positive pressure or vacuum (e.g., for moving/removing one or more fluids within/from the cassette and/or for controlling the rates of fluid flow), a valving system 28 (e.g., for actuating one or more valves), a detection system 34 (e.g., for detecting one or more fluids and/or processes), and/or a temperature regulating system 41 (e.g., to heat and/or cool one or more regions of the cassette). The components may be external or internal to the microfluidic device, and may optionally include one or more processors for controlling the component or system of components. In certain embodiments, one or more such components and/or processors are associated with a sample analyzer 47 configured to process and/or analyze a sample contained in the cassette.

In general, as used herein, a component that is "operatively associated with" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected (e.g., via channels such as tubing) so as to cause or enable the components so associated to perform their intended functionality.

The components shown illustratively in FIG. 1A, as well as other optional components such as those described herein, may be operatively associated with a control system 50. In some embodiments, the control system may be used to control fluids and/or conduct quality control by the use of feedback from one or more events taking place in the microfluidic system. For instance, the control system may be configured to receive input signals from the one or more components, to calculate and/or control various parameters, to compare one or more signals or a pattern of signals with signals preprogrammed into the control system, and/or to send signals to one or more components to modulate fluid flow and/or control operation of the microfluidic system, as described in more detail herein and in a U.S. Provisional Patent Application No. 61/325,023, filed Apr. 16, 2010 and entitled, "Feedback Control in Microfluidic Systems", which is incorporated herein by reference in its entirety for all purposes. The control system may also be optionally associated with other components such as a user interface 54, an identification system 56, an external communication unit 58 (e.g., a USB), and/or other components, as described in more detail below.

Cassette (e.g., microfluidic device) 20 may have any suitable configuration of channels and/or components for performing a desired analysis. In one set of embodiments, cassette 20 contains stored reagents that can be used for performing a chemical and/or biological reaction (e.g., an immunoassay), e.g., as described in more detail herein. The cassette may include, for example, an optional reagent inlet 62 in fluid communication with an optional reagent storage area 64. The storage area may include, for example, one or more channels and/or reservoirs that may, in some embodiments, be partially or completely filled with fluids (e.g., liquids and gases, including immiscible reagents such as reagent solutions and wash solutions, optionally separated by immiscible fluids, as described in more detail below). The cassette may also include an optional sample or reagent loading area 66, such as a fluidic connector that can be used to connect reagent storage area 64 to an optional measurement zone 68. The measurement zone, which may include one or more areas for detecting a component in a sample (e.g., measurement zones), may be in fluid communication with an optional waste area 70 and coupled to outlet 72. In some cases, such and other device features may be formed on or in different components or layers of a cassette, as described in more detail herein. Thus, it should be appreciated that a cassette may include a single component, or multiple components that are attached during use, such as a combination of an article with attached fluidic connector as described herein. In one set of embodiments, fluid may flow in the direction of the arrows shown in the figure. Further description and examples of such and other components are provided in more detail below.

In some embodiments, sections 71 and 77 of the cassette are not in fluid communication with one another prior to introduction of a sample into the cassette. In some cases, sections 71 and 77 are not in fluid communication with one another prior to first use of the cassette, wherein at first use, the sections are brought into fluid communication with one another. In other embodiments, however, sections 71 and 77 are in fluid communication with one another prior to first use and/or prior to introduction of a sample into the cassette. Other configurations of cassettes are also possible.

As shown in the exemplary embodiment illustrated in FIG. 1A, one or more fluid flow sources 40 such as a pump and/or a vacuum or other pressure-control system, valving system 28, detection system 34, temperature regulating system 41, and/or other components may be operatively associated with one or more of reagent inlet 62, reagent storage area 64, sample or reagent loading area 66, reaction area 68, waste area 70, outlet 72, and/or other regions of cassette 20. Detection of processes or events in one or more regions of the cassette can produce a signal or pattern of signals that can be transmitted to control system 50. Based on the signal(s) received by the control system, this feedback can be used to manipulate fluids within and/or between each of these regions of the microfluidic device, such as by controlling one or more of a pump, vacuum, valving system, detection system, temperature regulating system, and/or other components.

Figure 1B:
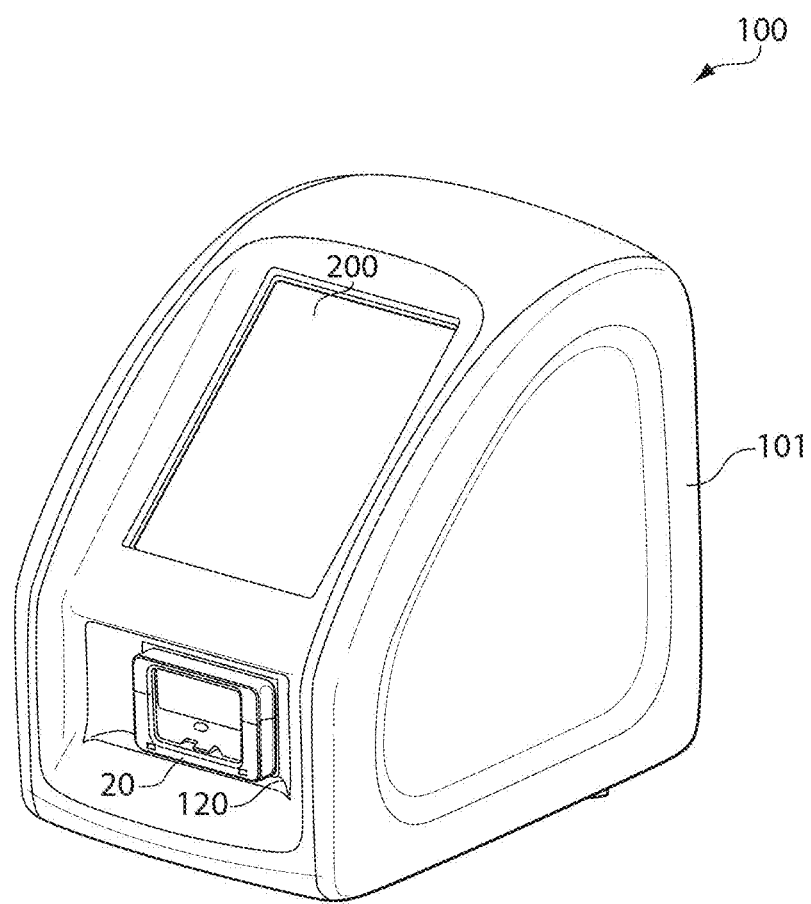
FIG. 1B is a perspective view of a sample analyzer and cassette according to one embodiment.
Figure 2:
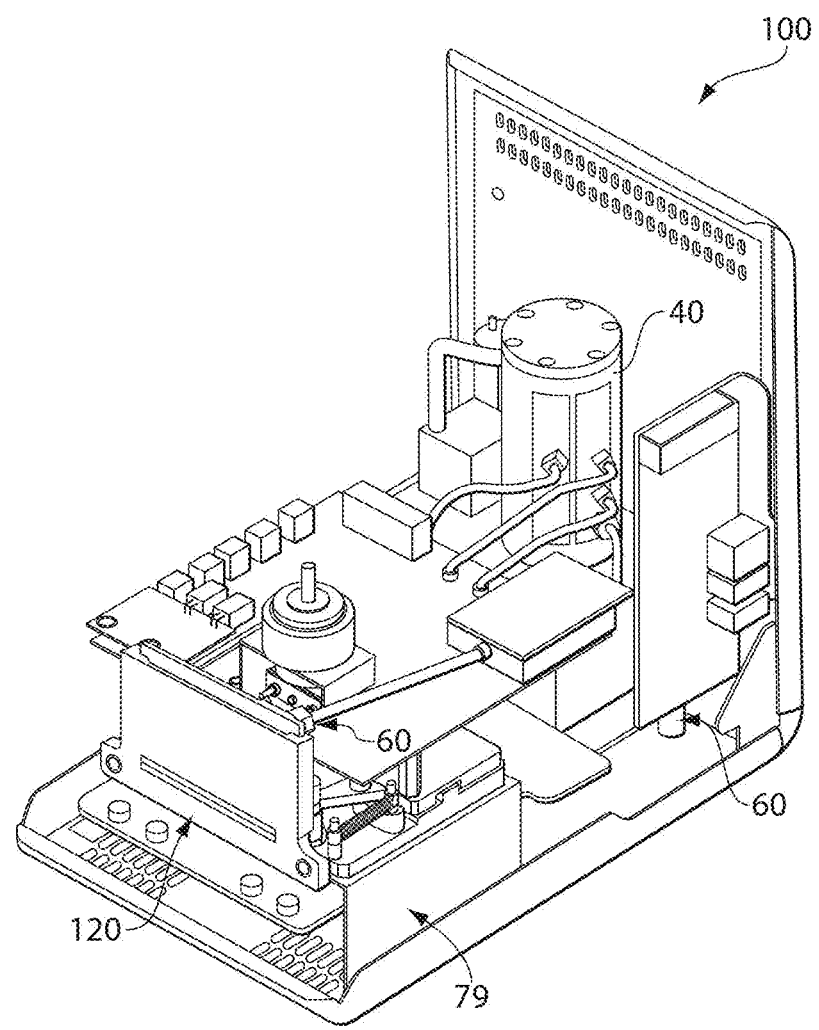
FIG. 2 is a perspective view of the internal components of a sample analyzer according to one embodiment with the housing removed.

Turning to FIGS. 1B-2, one embodiment of a microfluidic sample analyzer 100 is illustrated. As shown in the exemplary embodiment of FIG. 1B, the analyzer 100 includes a housing 101 which is configured to cover or retain the components of the analyzer 100 which are discussed in greater detail below. An opening 120 in the housing 101 is configured to receive a cassette 20. As set forth in greater detail below, the analyzer 100 may also include a user interface 200 positioned within the housing 101 which is configured for a user to input information into the sample analyzer. In this particular embodiment, the user interface 200 includes a touch screen, but as discussed below, the user interface may be configured differently.

FIG. 2 illustrates the sample analyzer 100 shown in FIG. 1B, except with a portion of the housing 101 and user interface 200 removed to depict some of the other components which may be positioned within the housing 101. These components will be described in greater detail below and include, but are not limited to a fluid flow source 40 (e.g., a vacuum system) configured to pressurize the cassette 20, an identification reader 60 configured to read information associated with the cassette, and a mechanical subsystem 79 which includes a component configured to interface with the cassette to detect the cassette within the housing. As mentioned above, an opening 120 in the housing is configured to receive a cassette 20. As shown in FIG. 2, in one embodiment, the opening 120 is configured as an elongated slot. The opening 120 may be configured in this manner to receive a substantially card-shaped cassette. It should be appreciated that in other embodiments, the opening 120 may be shaped and configured differently as the invention is not so limited.

Figure 3:
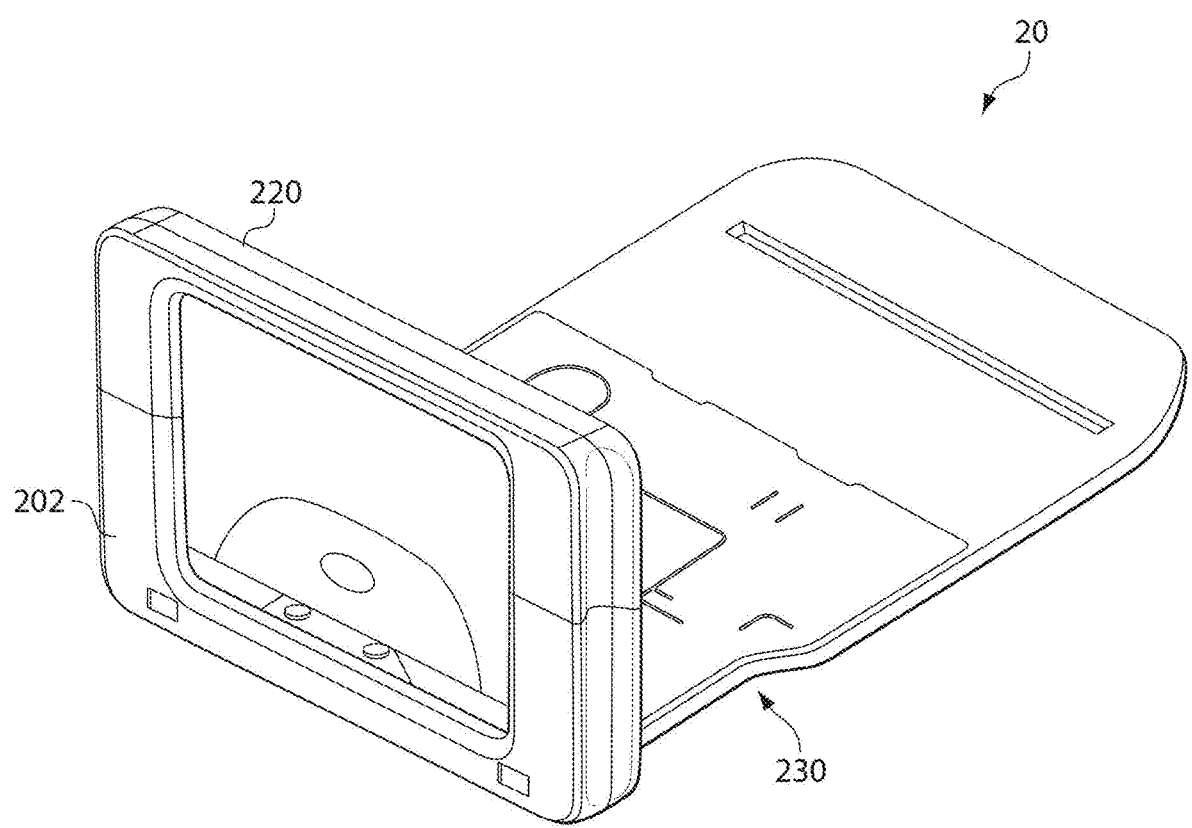
FIG. 3 is a perspective view of a cassette including a fluidic connector according to one embodiment.
Figure 4:
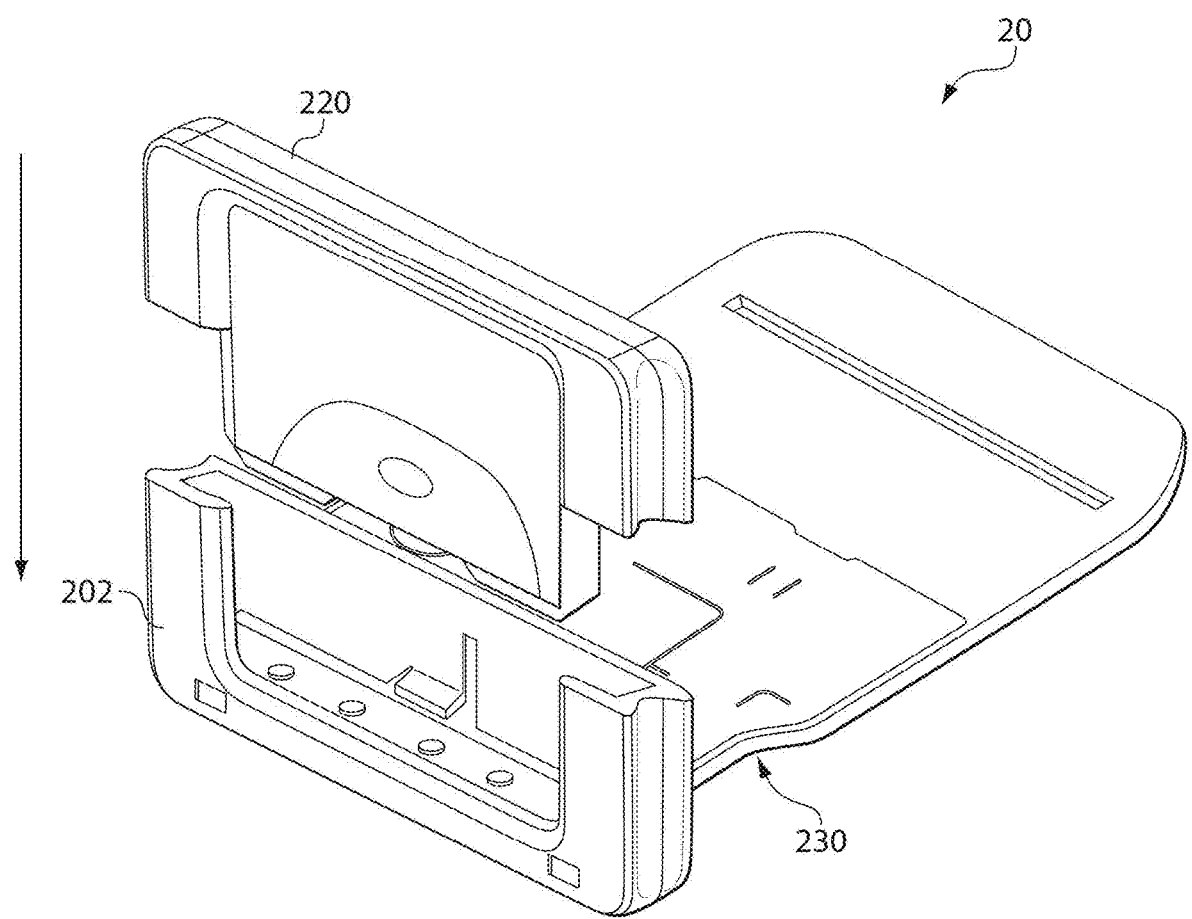
FIG. 4 is a perspective view showing the insertion of a fluidic connector into a portion of a cassette according to one embodiment.

As mentioned above, the microfluidic sample analyzer 100 may be configured to receive a variety of types of cassettes 20 (e.g., microfluidic devices). FIGS. 3-9 illustrate various exemplary embodiments of the cassette 20 for use with an analyzer 100. As shown in FIGS. 3-4 and 6, the cassette 20 may be substantially card-shaped (i.e. similar to a card key) having a substantially rigid plate-like structure. Non-limiting examples of microfluidic systems that can be part of cassette that can be used with the systems and methods described herein are described in more detail in International Patent Publication No. WO2005/066613 (International Patent Application Serial No. PCT/US2004/043585), filed Dec. 20, 2004 and entitled "Assay Device and Method" and U.S. patent application Ser. No. 12/113,503, published as U.S. Patent Publication No. 2008/0273918, filed May 1, 2008 and entitled "Fluidic Connectors and Microfluidic Systems", each of which are incorporated herein by reference in their entireties for all purposes.

The cassette 20 may be configured to include a fluidic connector 220, which as shown in exemplary embodiment illustrated in FIG. 4, may snap into one end of the cassette 20. In certain embodiments, the fluidic connector can be used to introduce one or more fluids (e.g., a sample or a reagent) into the cassette.

In one set of embodiments, the fluidic connector is used to fluidly connect two (or more) channels of the cassette during first use, which channels are not connected prior to first use. For example, the cassette may include two channels that are not in fluid communication prior to first use of the cassette. Non-connected channels may be advantageous in certain cases, such as for storing different reagents in each of the channels. For example, a first channel may be used to store dry reagents and a second channel may be used to store wet reagents. Having the channels be physically separated from one another can enhance long-term stability of the reagents stored in each of the channels, e.g., by keeping the reagent(s) stored in dry form protected from moisture that may be produced by reagent(s) stored in wet form. At first use, the channels may be connected via the fluidic connector to allow fluid communication between the channels of the cassette. For instance, the fluidic connected may puncture seals covering inlets and/or outlets of the cassette to allow insertion of the fluidic connector into the cassette.

As used herein, "prior to first use of the cassette" means a time or times before the cassette is first used by an intended user after commercial sale. First use may include any step(s) requiring manipulation of the device by a user. For example, first use may involve one or more steps such as puncturing a sealed inlet to introduce a reagent into the cassette, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the cassette. Those of ordinary skill in the art are well aware of the meaning of first use in this context, and will be able easily to determine whether a cassette of the invention has or has not experienced first use. In one set of embodiments, cassette of the invention are disposable after first use (e.g., after completion of an assay), and it is particularly evident when such devices are first used, because it is typically impractical to use the devices at all (e.g., for performing a second assay) after first use.

A cassette may be coupled to a fluidic connector using a variety of mechanisms. For example, the fluidic connector may include at least one non-fluidic feature complementary to a feature of the cassette so as to form a non-fluidic connection between the fluidic connector and the cassette upon attachment. The non-fluidic complementary feature may be, for example, a protruding feature of the fluidic connector and corresponding complementary cavities of the cassette, which can help the user align the fluidic connector with the cassette. In some cases, the feature creates a substantial resistance to movement of the fluidic connector relative to the cassette and/or alignment element upon the alignment element receiving the fluidic component (e.g., upon insertion of the fluidic component into the alignment element) and/or during intended use of the device. The fluidic connector and/or cassette may optionally include one or more features such as snap features (e.g., indentations), grooves, openings for inserting clips, zip-tie mechanisms, pressure-fittings, friction-fittings, threaded connectors such as screw fittings, snap fittings, adhesive fittings, magnetic connectors, or other suitable coupling mechanisms. These and other examples of coupling mechanisms are described in more detail in U.S. patent application Ser. No. 12/113,503, published as U.S. Patent Publication No. 2008/0273918, filed May 1, 2008 and entitled "Fluidic Connectors and Microfluidic Systems", which is incorporated herein by reference in its entirety for all purposes. Connection of the fluidic connector to the cassette may involve forming a liquid-tight and/or air-tight seal between the components. Attachment of a fluidic connector to a cassette may be reversible or irreversible.

As shown, the cassette 20 may be configured to include a fluidic connector 220. In particular, the cassette 20 may include a fluidic connector alignment element 202 which is configured to receive and mate with the connector 220. For instance, the alignment element may extend from the base of the cassette and comprise a cavity constructed and arranged to receive and engage the fluidic connector and thereby position the fluidic connector in a predetermined, set configuration relative to the base of the cassette. As shown in the illustrative embodiments of FIG. 4, the cassette may include an alignment element that extends approximately perpendicular to the cassette. In other embodiments, the alignment element may extend approximately parallel to the cassette. Examples of alignment elements are described in more detail in U.S. patent application Ser. No. 12/113,503, published as U.S. Patent Publication No. 2008/0273918, filed May 1, 2008 and entitled "Fluidic Connectors and Microfluidic Systems", which is incorporated herein by reference in its entirety for all purposes.

In some embodiments, the configuration of the alignment element and the fluidic connector may be adapted to allow insertion of the fluidic connector into the alignment element by a sliding motion. For example, the fluidic connector may slide against one or more surfaces of the alignment element when the fluidic connector is inserted into the alignment element.

Figure 5:
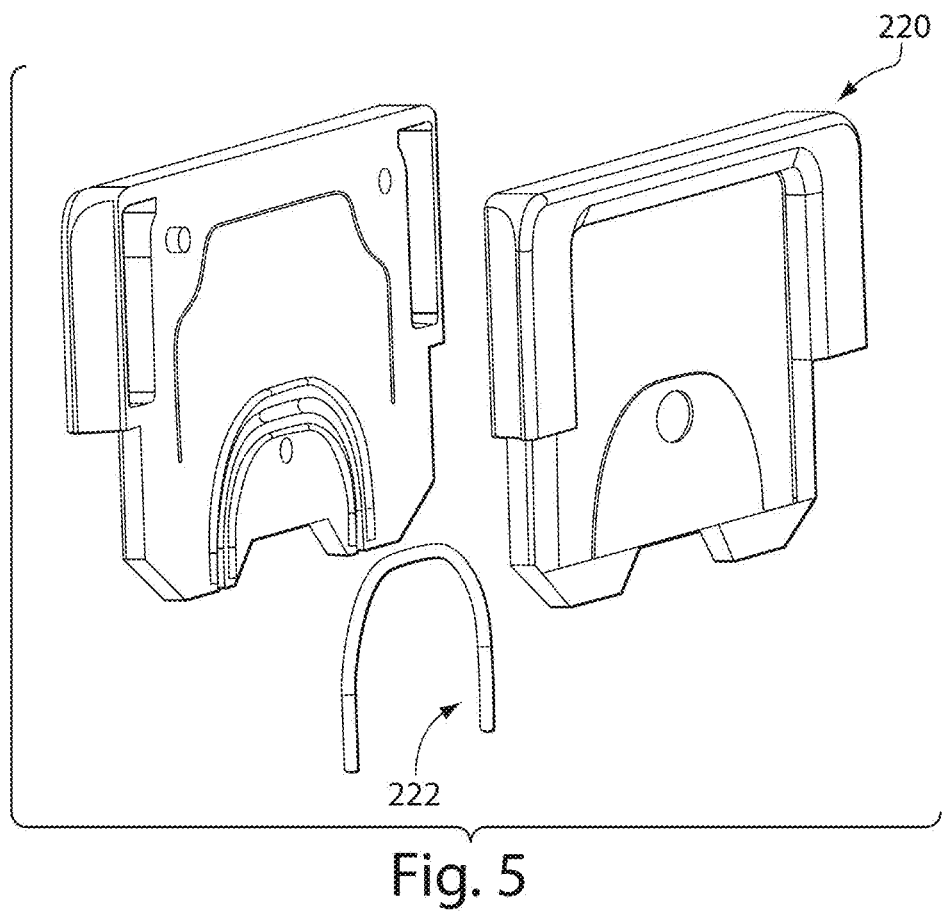
FIG. 5 is an exploded assembly view of a fluidic connector according to one embodiment.
Figure 6:
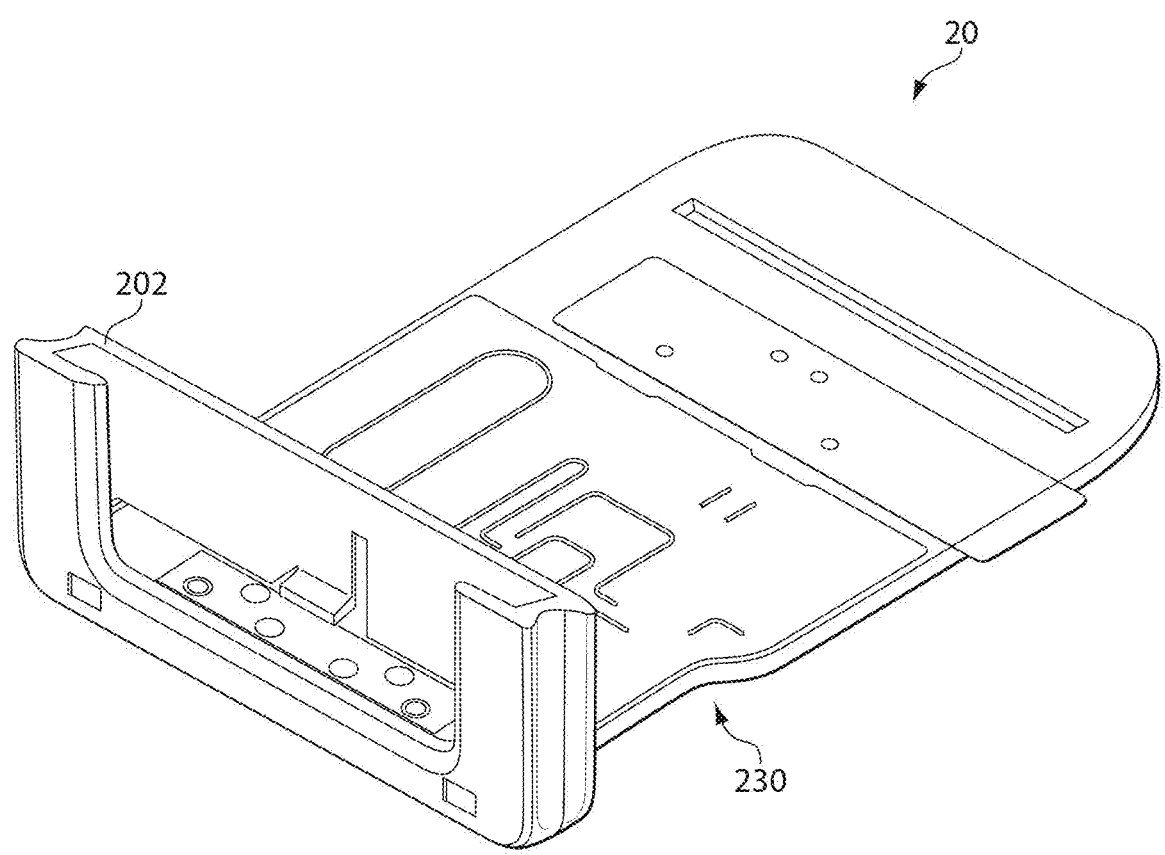
FIG. 6 is a perspective view of a cassette according to one embodiment.
Figure 7:
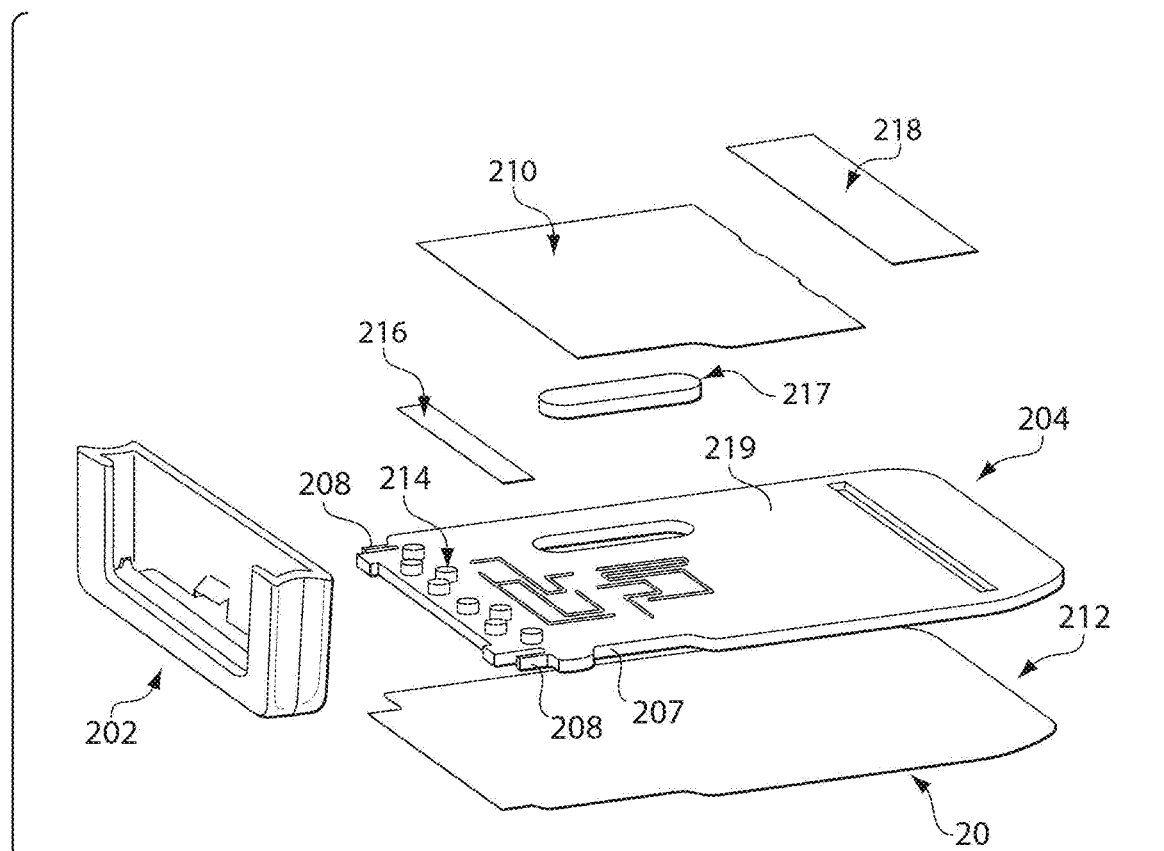
FIG. 7 is a an exploded assembly view of a cassette according to one embodiment.

As shown in exemplary embodiment illustrated in FIG. 5, the fluidic connector 220 may include a substantially U-shaped channel 222 which may hold a fluid and/or reagent (e.g., a fluid sample) prior to be connected to the cassette. Channel 222 may be housed between two shell components which form the connector 220. In some embodiments, the fluidic connector may be used to collect a sample from the patient prior to the fluidic connector being connected to the cassette. For example, a lancet or other suitable instrument can be used to obtain a finger-stick blood sample which may then be collected by the fluidic connector 220 and loaded into channel 222 by capillary action. In other embodiments, the fluidic connector 220 may be configured to puncture a patient's finger to collect the sample in the channel 222. In certain embodiments, fluid connector 220 does not contain a sample (or reagent) prior to connection to the cassette, but simply allows fluid communication between two or more channels of the cassette upon connection. In one embodiment, the U-shaped channel is formed with a capillary tube. The fluidic connector can also include other channel configurations, and in some embodiments, may include more than one channels that may be fluidically connected or unconnected to one another.

FIGS. 6-9 illustrate various exemplary embodiments of the cassette 20 in greater detail. As shown illustratively in the exploded assembly view of FIG. 7, the cassette 20 may include a cassette body 204 which includes at least one channel 206 configured to receive a sample or reagent and through which a sample or reagent may flow. The cassette body 204 may also include latches 208 positioned on one end that interlock with the fluidic connector alignment element 202 for a snap fit.

The cassette 20 may also include top and bottom covers 210 and 212, which may, for example, be made of a transparent material. In some embodiments, a cover can be in the form of a biocompatible adhesive and can be made of a polymer (e.g., polyethylene (PE), a cyclic olefin copolymer (COC), polyvinyl chloride (PVC)) or an inorganic material for example. In some cases, one or more covers are in the form of an adhesive film (e.g., a tape). For some applications, the material and dimensions of a cover are chosen such that the cover is substantially impermeable to water vapor. In other embodiments, the cover can be non-adhesive, but may bond thermally to the microfluidic substrate by direct application of heat, laser energy, or ultrasonic energy. Any inlet(s) and/or outlet(s) of a channel of the cassette can be sealed (e.g., by placing an adhesive over the inlet(s) and/or outlet(s)) using one or more covers. In some cases, the cover substantially seals one or more stored reagents in the cassette.

As illustrated, the cassette body 204 may include one or more ports 214 coupled to the channel 206 in the cassette body 204. These ports 214 can be configured to align with the substantially U-shaped channel 222 in the fluidic connector 220 when the fluidic connector 220 is coupled to the cassette 20 to fluidly connect the channel 206 in the cassette body 204 with the channel 222 in the fluidic connector 220. In certain embodiments, substantially U-shaped channel 222 can also be fluidically connected to channel 207, thereby coupling channels 206 and 207. As shown, a cover 216 may be provided over the ports 214 and the cover 216 may be configured to be pieced or otherwise opened (e.g., by the connector 220 or by other means) to fluidly connect the two channels 206 and 222. Additionally, a cover 218 may be provided to cover port 219 (e.g., a vacuum port) in the cassette body 204. As set forth in further detail below, the port 219 may be configured to fluidly connect a fluid flow source 40 with the channel 206 to move a sample through the cassette. The cover 218 over the port 219 may be configured to be pierced or otherwise opened to fluidly connect the channel 206 with the fluid flow source 40.

The cassette body 204 may optionally include a liquid containment region such as a waste area, including an absorbent material 217 (e.g., a waste pad). In some embodiments, the liquid containment region includes regions that capture one or more liquids flowing in the cassette, while allowing gases or other fluids in the cassette to pass through the region. This may be achieved, in some embodiments, by positioning one or more absorbent materials in the liquid containment region for absorbing the liquids. This configuration may be useful for removing air bubbles from a stream of fluid and/or for separating hydrophobic liquids from hydrophilic liquids. In certain embodiments, the liquid containment region prevents liquids from passing through the region. In some such cases, the liquid containment region may act as a waste area by capturing substantially all of the liquid in the cassette, thereby preventing liquid from exiting the cassette (e.g., while allowing gases to escape from an outlet of the cassette). For example, the waste area may be used to store the sample and/or reagents in the cassette after they have passed through the channel 206 during the analysis of the sample. These and other arrangements may be useful when the cassette is used as a diagnostic tool, as the liquid containment region may prevent a user from being exposed to potentially-harmful fluids in the cassette. Non-limiting examples of liquid containment regions are described in more detail in U.S. patent application Ser. No. 12/196,392, published as U.S. Patent Publication No. 2009/0075390, filed Aug. 22, 2008, entitled "Liquid containment for integrated assays", which is incorporated herein by reference in its entirety for all purposes.

Figure 8:
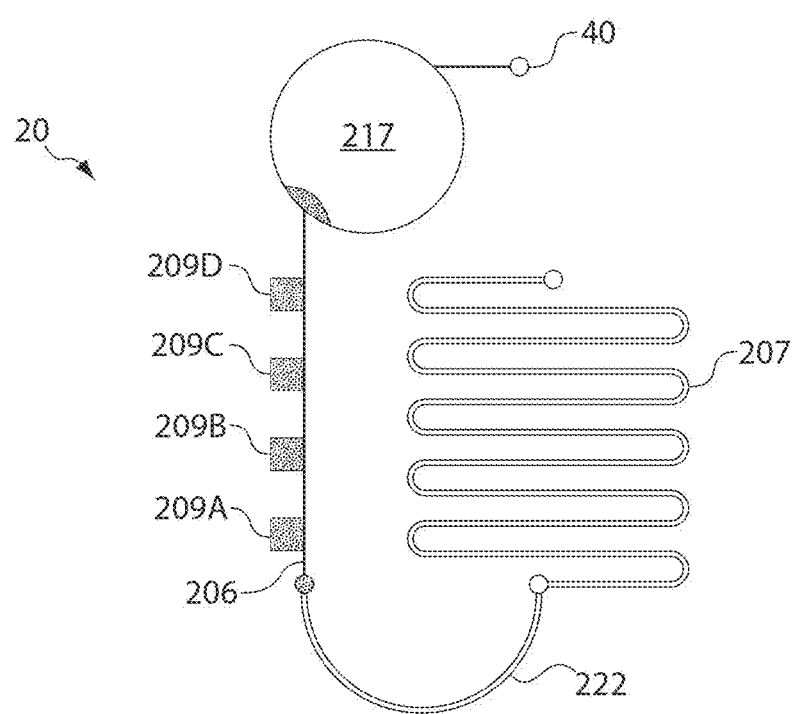
FIG. 8 is a schematic view of a cassette including a fluidic connector according to one embodiment.

The schematic view of the cassette 20 illustrated in FIG. 8 shows one embodiment where the cassette 20 includes a first channel 206 and a second channel 207 spaced apart from the first channel 206. In one embodiment, the channels 206, 207 range in largest cross-section dimension from approximately 50 micrometers to approximately 500 micrometers, although other channel sizes and configurations may be used, as described in more detail below.

The first channel 206 may include one or more measurement zones 209 used to analyze the sample. For example, in one illustrative embodiment, the channel 206 includes four measurement zones 209 (e.g., connected in series or in parallel) which are utilized during sample analysis.

In certain embodiments, one or more measurement zones are in the form of meandering regions (e.g., involving meandering channels), as described in more detail below and in International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, published as U.S. Patent Publication No. 2008/0273918, filed May 1, 2008 and entitled "Fluidic Connectors and Microfluidic Systems" and U.S. patent application Ser. No. 12/196,392, published as U.S. Patent Publication No. 2009/0075390, filed Aug. 22, 2008, entitled "Liquid containment for integrated assays", each of which is incorporated herein by reference in their entireties for all purposes. A meandering region may, for example, be defined by an area of at least $0.25$ $mm^2$, at least $0.5$ $mm^2$, at least $0.75$ $mm^2$, or at least $1.0$ $mm^2$, wherein at least 25%, 50%, or 75% of the area of the meandering region comprises an optical detection pathway. A detector that allows measurement of a single signal through more than one adjacent segments of the meandering region may be positioned adjacent the meandering region. In some cases, channel 206 is fluidically connected to at least two meandering regions connected in series.

As described herein, the first channel 206 and/or the second channel 207 may be used to store one or more reagents used to process and analyze the sample prior to first use of the cassette. In some embodiments, dry reagents are stored in one channel or section of a cassette and wet reagents are stored in a second channel or section of cassette. Alternatively, two separate sections or channels of a cassette may both contain dry reagents and/or wet reagents. Reagents can be stored and/or disposed, for example, as a liquid, a gas, a gel, a plurality of particles, or a film. The reagents may be positioned in any suitable portion of a cassette, including, but not limited to, in a channel, reservoir, on a surface, and in or on a membrane, which may optionally be part of a reagent storage area. A reagent may be associated with a cassette (or components of a cassette) in any suitable manner. For example, reagents may be crosslinked (e.g., covalently or ionically), absorbed, or adsorbed (physisorbed) onto a surface within the cassette. In one particular embodiment, all or a portion of a channel (such as a fluid path of a fluid connector or a channel of the cassette) is coated with an anti-coagulant (e.g., heparin). In some cases, a liquid is contained within a channel or reservoir of a cassette prior to first use and/or prior to introduction of a sample into the cassette.

In some embodiments, the stored reagents may include fluid plugs positioned in linear order so that during use, as fluids flow to a reaction site, they are delivered in a predetermined sequence. A cassette designed to perform an assay, for example, may include, in series, a rinse fluid, a labeled-antibody fluid, a rinse fluid, and a amplification fluid, all stored therein. While the fluids are stored, they may be kept separated by substantially immiscible separation fluids (e.g., a gas such as air) so that fluid reagents that would normally react with each other when in contact may be stored in a common channel.

Reagents can be stored in a cassette for various amounts of time. For example, a reagent may be stored for longer than 1 hour, longer than 6 hours, longer than 12 hours, longer than 1 day, longer than 1 week, longer than 1 month, longer than 3 months, longer than 6 months, longer than 1 year, or longer than 2 years. Optionally, the cassette may be treated in a suitable manner in order to prolong storage. For instance, cassettes having stored reagents contained therein may be vacuum sealed, stored in a dark environment, and/or stored at low temperatures (e.g., below 0 degrees C.). The length of storage depends on one or more factors such as the particular reagents used, the form of the stored reagents (e.g., wet or dry), the dimensions and materials used to form the substrate and cover layer(s), the method of adhering the substrate and cover layer(s), and how the cassette is treated or stored as a whole. Storing of a reagent (e.g., a liquid or dry reagent) in a channel may involve sealing the inlet(s) and outlet(s) of the channel prior to first use or during packaging of the device.

As illustrated in the exemplary embodiment shown in FIGS. 8 and 9A-9F, channels 206 and 207 may not be in fluid communication with each other until the fluidic connector 220 is coupled to the cassette 20. In other words, the two channels, in some embodiments, are not in fluid communication with one another prior to first use and/or prior to introduction of a sample into the cassette. In particular, as illustrated, the substantially U-shaped channel 222 of the connector 220 may fluidly connect the first and second channels 206, 207 such that the reagents in the second channel 207 can pass through the U-shaped channel 22 and selectively move into the measurement zones 209 in the first channel 206. In other embodiments, the two channels 206 and 207 are in fluid communication with one another prior to first use, and/or prior to introduction of a sample into the cassette, but the fluidic connector further connects the two channels (e.g., to form a closed-loop system) upon first use.

In some embodiments, a cassette described herein may include one more microfluidic channels, although such cassettes are not limited to microfluidic systems and may relate to other types of fluidic systems. "Microfluidic," as used herein, refers to a cassette, device, apparatus or system including at least one fluid channel having a maximum cross-sectional dimension of less than 1 mm, and a ratio of length to largest cross-sectional dimension of at least 3:1. A "microfluidic channel," as used herein, is a channel meeting these criteria.

The "cross-sectional dimension" (e.g., a diameter) of the channel is measured perpendicular to the direction of fluid flow. Most fluid channels in components of cassettes described herein have maximum cross-sectional dimensions less than 2 mm, and in some cases, less than 1 mm. In one set of embodiments, all fluid channels of a cassette are microfluidic or have a largest cross sectional dimension of no more than 2 mm or 1 mm. In another set of embodiments, the maximum cross-sectional dimension of the channel(s) are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any suitable method known to those of ordinary skill in the art. In some cases, more than one channel or capillary may be used.

A channel may include a feature on or in an article (e.g., a cassette) that at least partially directs the flow of a fluid. The channel can have any suitable cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more.

Cassettes described herein may include channels or channel segments positioned on one or two sides of the cassette. In some cases, the channels are formed in a surface of the cassette. The channel segments may be connected by an intervening channel passing through the cassette. Non-limiting examples of such and other channel configurations are described in more detail in U.S. patent application Ser. No. 12/640,420, filed Dec. 17, 2009, entitled, "Reagent Storage in Microfluidic Systems and Related Articles and Methods", which is incorporated herein by reference in its entirety for all purposes. In some embodiments, the channel segments are used to store reagents in the device prior to first use by an end user. The specific geometry of the channel segments and the positions of the channel segments within the cassettes may allow fluid reagents to be stored for extended periods of time without mixing, even during routine handling of the cassettes such as during shipping of the cassettes, and when the cassettes are subjected to physical shock or vibration.

In certain embodiments, a cassette includes optical elements that are fabricated on one side of a cassette opposite a series of fluidic channels. An "optical element" is used to refer to a feature formed or positioned on or in an article or cassette that is provided for and used to change the direction (e.g., via refraction or reflection), focus, polarization, and/or other property of incident electromagnetic radiation relative to the light incident upon the article or cassette in the absence of the element. For example, an optical element may comprise a lens (e.g., concave or convex), mirror, grating, groove, or other feature formed or positioned in or on a cassette. A cassette itself absent a unique feature, however, would not constitute an optical element, even though one or more properties of incident light may change upon interaction with the cassette. The optical elements may guide incident light passing through the cassette such that most of the light is dispersed away from specific areas of the cassette, such as intervening portions between the fluidic channels. By decreasing the amount of light incident upon these intervening portions, the amount of noise in a detection signal can be decreased when using certain optical detection systems. In some embodiments, the optical elements comprise triangular grooves formed on or in a surface of the cassette. The draft angle of the triangular grooves may be chosen such that incident light normal to the surface of the cassette is redirected at an angle dependent upon the indices of refraction of the external medium (e.g., air) and the cassette material. In some embodiments, one or more optical elements are positioned between adjacent segments of a meandering region of a measurement zone. Non-limiting examples of optical elements and configurations of channels and components with respect to the optical elements are described in more detail in U.S. patent application Ser. No. 12/698,451, filed Feb. 2, 2010, entitled, "Structures for Controlling Light Interaction with Microfluidic Devices", which is incorporated herein by reference in its entirety for all purposes.

A cassette, or portions thereof, can be fabricated of any material suitable for forming a channel or other component. Non-limiting examples of materials include polymers (e.g., polyethylene, polystyrene, polymethylmethacrylate, polycarbonate, poly(dimethylsiloxane), PVC, PTFE, PET, and a cyclo-olefin copolymer), glass, quartz, and silicon. The material forming the cassette and any associated components (e.g., a cover) may be hard or flexible. Those of ordinary skill in the art can readily select suitable material(s) based upon e.g., its rigidity, its inertness to (e.g., freedom from degradation by) a fluid to be passed through it, its robustness at a temperature at which a particular device is to be used, its transparency/opacity to light (e.g., in the ultraviolet and visible regions), and/or the method used to fabricate features in the material. For instance, for injection molded or other extruded articles, the material used may include a thermoplastic (e.g., polypropylene, polycarbonate, acrylonitrile-butadiene-styrene, nylon 6), an elastomer (e.g., polyisoprene, isobutene-isoprene, nitrile, neoprene, ethylene-propylene, hypalon, silicone), a thermoset (e.g., epoxy, unsaturated polyesters, phenolics), or combinations thereof. As described in more detail below, cassettes including two or more components or layers may be formed in different materials to tailor the components to the major function(s) of the each of the components, e.g., based upon those factors described above and herein.

In some embodiments, the material and dimensions (e.g., thickness) of a cassette and/or cover are chosen such that it is substantially impermeable to water vapor. For instance, a cassette designed to store one or more fluids therein prior to first use may include a cover comprising a material known to provide a high vapor barrier, such as metal foil, certain polymers, certain ceramics and combinations thereof. Examples of materials having low water vapor permeability are provided below. In other cases, the material is chosen based at least in part on the shape and/or configuration of the cassette. For instance, certain materials can be used to form planar devices whereas other materials are more suitable for forming devices that are curved or irregularly shaped.

In some instances, a cassette is comprised of a combination of two or more materials, such as the ones listed above. For instance, channels of the cassette may be formed in polystyrene or other polymers (e.g., by injection molding) and a biocompatible tape may be used to seal the channels. The biocompatible tape or flexible material may include a material known to improve vapor barrier properties (e.g., metal foil, polymers or other materials known to have high vapor barriers), and may optionally allow access to inlets and outlets by puncturing or unpeeling the tape. A variety of methods can be used to seal a microfluidic channel or portions of a channel, or to join multiple layers of a device, including but not limited to, the use of adhesives, use adhesive tapes, gluing, bonding, lamination of materials, or by mechanical methods (e.g., clamping, snapping mechanisms, etc.).

In some instances, a cassette comprises a combination of two or more separate components (e.g., layers or cassettes) mounted together. Independent channel networks (such as sections 71 and 77 of FIG. 1A), which may optionally include reagents stored therein prior to first use, may be included on or in the different components of the cassette. The separate components may be mounted together or otherwise associated with one another by any suitable means, such as by the methods described herein, e.g., to form a single (composite) cassette. In some embodiments, two or more channel networks are positioned in different components or layers of the cassette and are not connected fluidically prior to first use, but are connected fluidically at first use, e.g., by use of a fluidic connector. In other embodiments, the two or more channel networks are connected fluidically prior to first use.

Advantageously, each of the different components or layers that form a composite cassette may be tailored individually depending on the designed function(s) of that component or layer. For example, in one set of embodiments, one component of a composite cassette may be tailored for storing wet reagents. In some such embodiments, that component may be formed in a material having a relatively low vapor permeability. Additionally or alternatively, e.g., depending on the amount of fluids to be stored, the storage region(s) of that cassette may be made with larger cross-sectional dimensions than channels or regions of other components not used for storage of liquids. The material used to form the cassette may be compatible with fabrication techniques suitable for forming larger cross-sectional dimensions. By contrast, a second component that may be tailored for detection of an analyte may, in some embodiments, include channel portions having smaller cross-sectional dimensions. Smaller cross-sectional dimensions may be useful, for example, in certain embodiments to allow more contact time between fluids flowing in the channel (e.g., a reagent solution or a wash fluid) and an analyte bound to a surface of the channel, for a given volume of fluid. Additionally or alternatively, a channel portion of the second component may have a lower surface roughness (e.g., to increase the signal to noise ratio during detection) compared to a channel portion of another component. The smaller-cross sectional dimensions or lower surface roughness of the channel portions of the second component may, in certain embodiments, require a certain fabrication technique or fabrication tool different from that used to form a different component of the cassette. Furthermore, in some particular embodiments, the material used for the second component may be well characterized for protein attachment and detection. As such, it may be advantageous to form different channels portions used for different purposes on different components of a cassette, which can then be joined together prior to use by an intended user. Other advantages, features of components, and examples are provided below.

FIGS. 9B-9E show a device that may include multiple components 20B and 20C that are combined to form a single cassette. As shown in these illustrative embodiments, component 20B may include a first side 21A and a second side 21B. Component 20C may include a first side 22A and a second side 22B. Device components or parts described herein such as channels or other entities may be formed at, on, or in the first side of a component, a second side of a component and/or through the component in some embodiments. For example, as shown illustratively in FIG. 9C, component 20C may include a channel 206 having an inlet and an outlet, and may be formed in a first material. Channel 206 may have any suitable configuration as described herein and may include, for example, one or more reagent storage regions, measurement zones, liquid containment regions, mixing regions, and the like. In some embodiments, channel 206 is not formed through the entire thickness of component 20B. That is, the channel may be formed at or in one side of the component. Channel 206 may be optionally enclosed by a cover as described herein such as a tape (not shown), another component or layer of the cassette, or other suitable component. In other embodiments, channel 206 is formed through the entire thickness of component 20B and covers are required on both sides of the cassette to enclose the channel.

Component 20B may include channel 207 having an inlet and an outlet, and may be formed in a second material, which may be the same or different as the first material. Channel 207 may also have any suitable configuration as described herein, and may or may not be formed through the entire thickness of component 20C. Channel 207 may be enclosed by one or more covers. In some cases, the cover is not a component that includes one or more fluidic channels such as component 20C. For example, the cover may be a biocompatible tape or other surface positioned between components 20B and 20C. In other embodiments, channel 207 may be substantially enclosed by component 20C. That is, surface 22A of component 20C may form a portion of channel 207 as components 20B and 20C lay directly adjacent to one another.

Figure 9A:
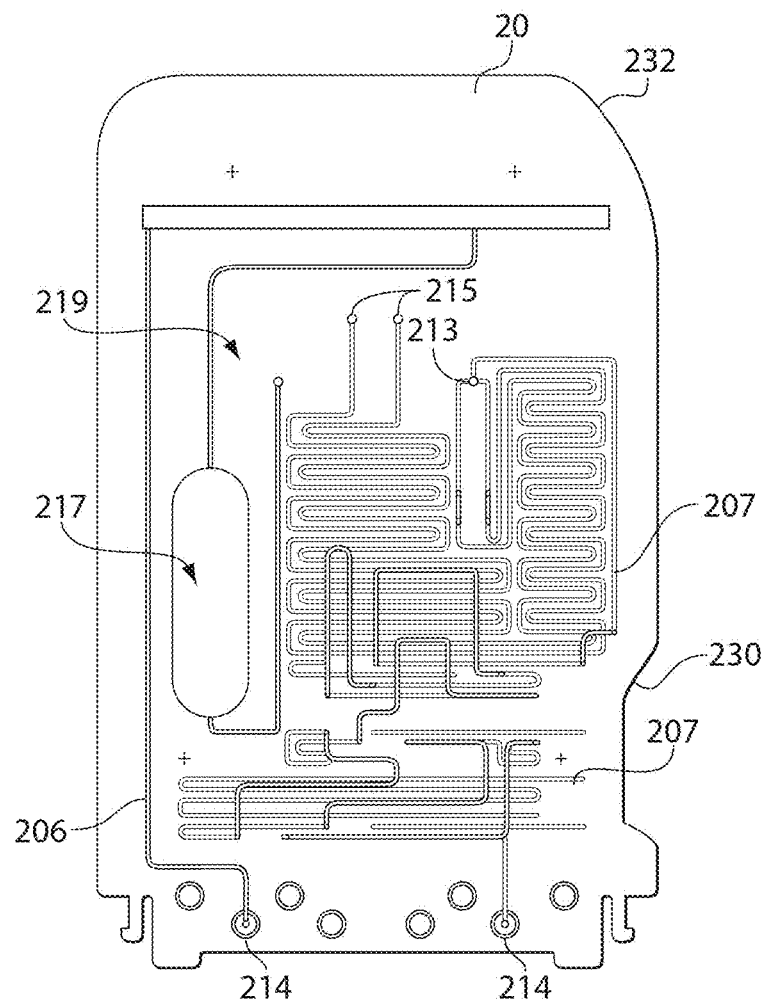
FIG. 9A is a schematic view of a cassette according to one embodiment.
Figure 9B:
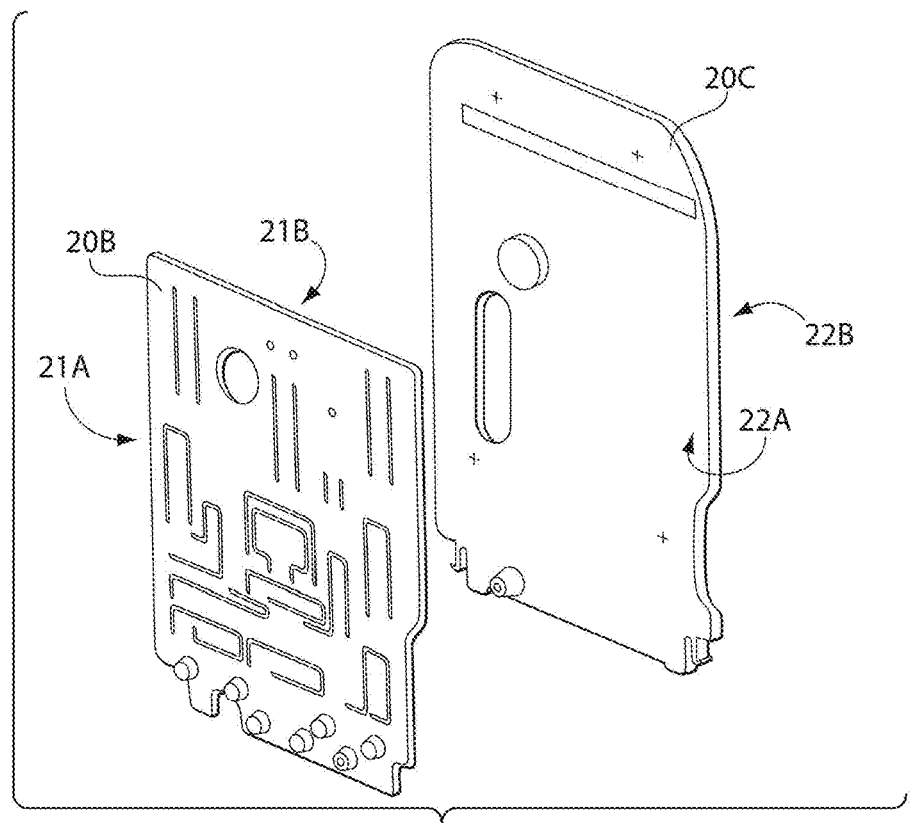
FIGS. 9B-9F are schematic views of cassettes formed of multiple components according to one set of embodiments.
Figure 9C:
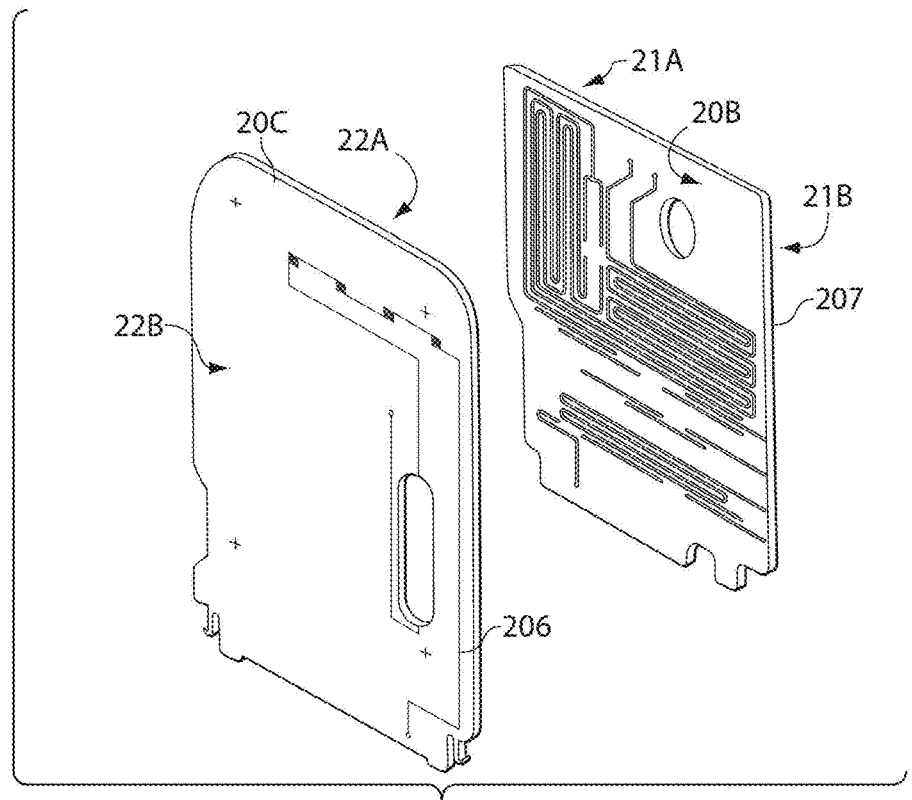
Figure 9D:
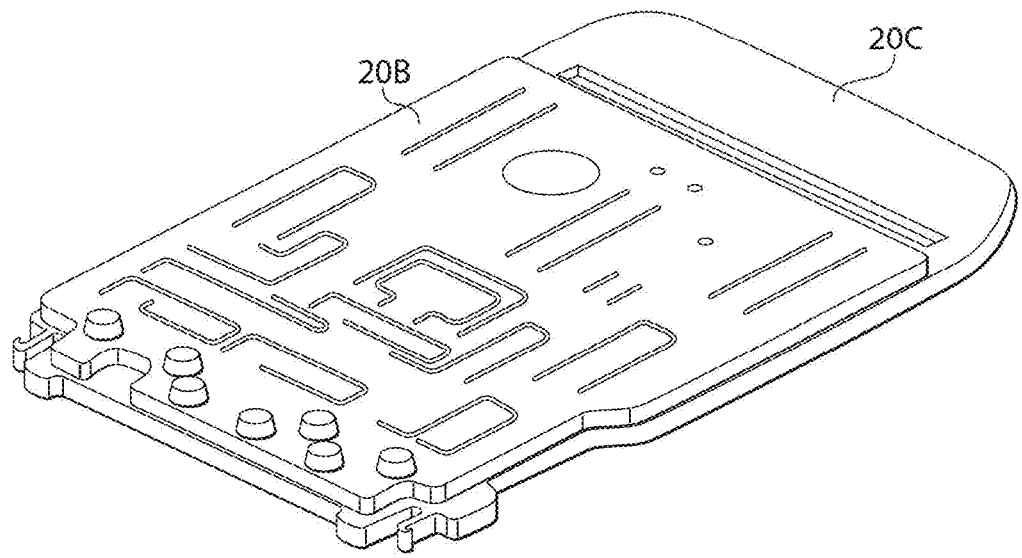
Figure 9E:
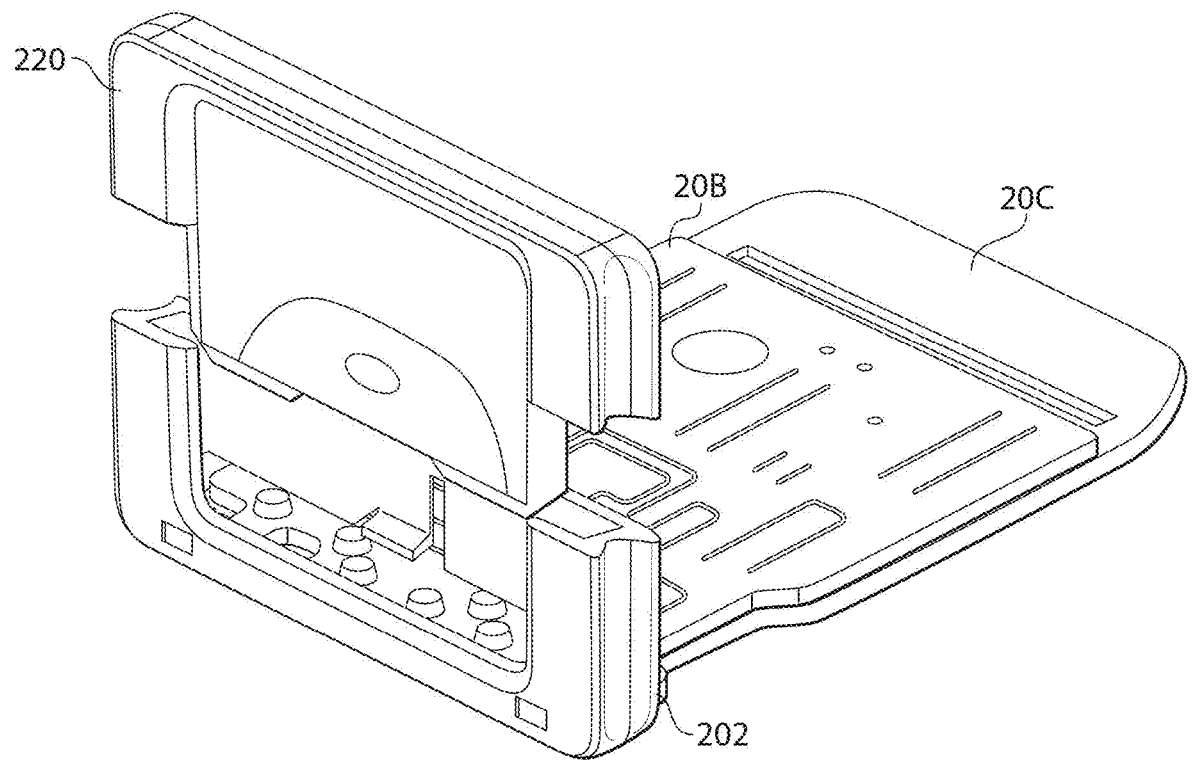
Figure 9F:
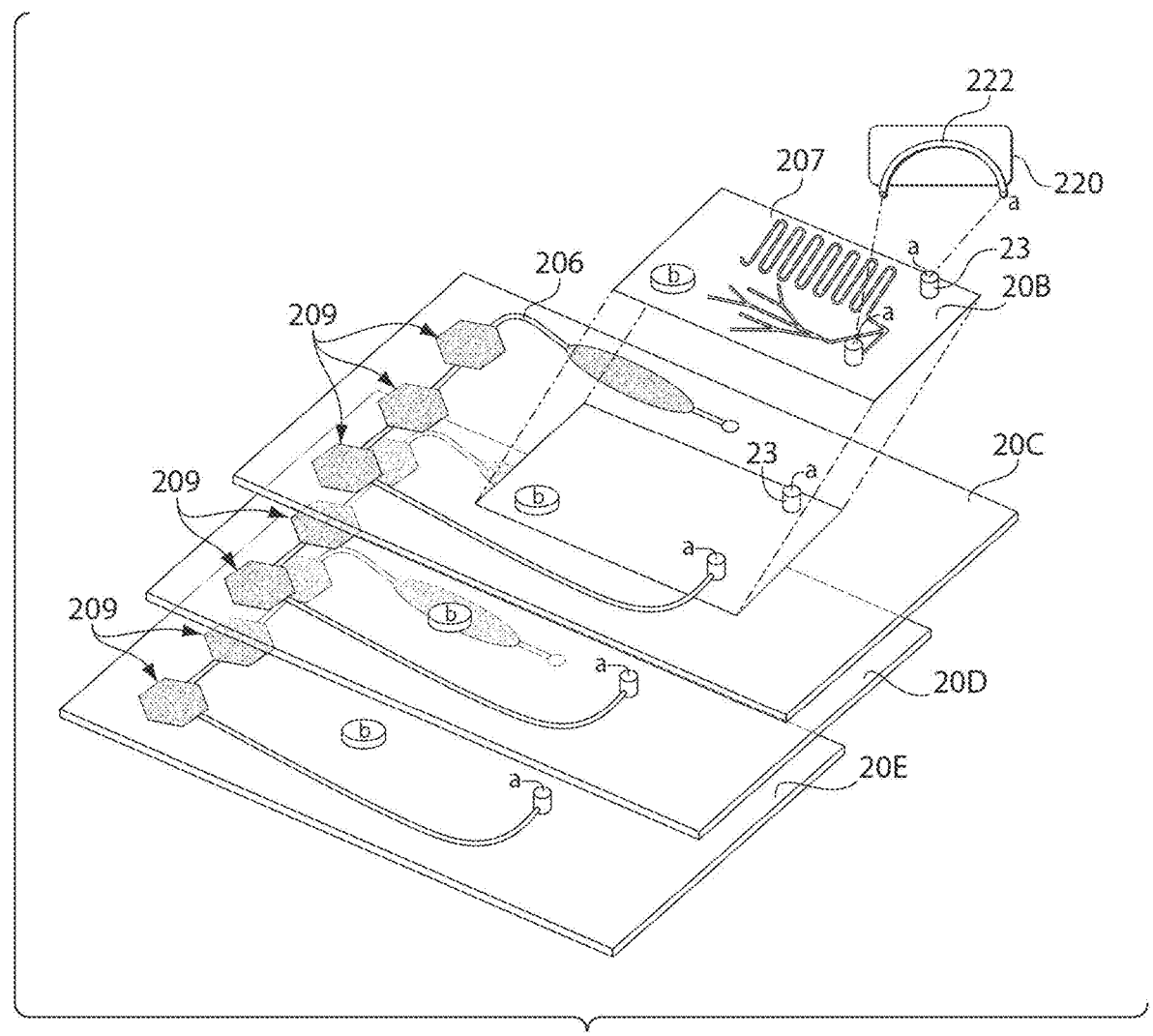

As shown illustratively in FIGS. 9D and 9E, components 20B and 20C may be substantially planar and may lay on top of one another. In general, however, the two or more components forming a cassette can lay in any suitable configuration with respect to one another. In some cases, the components lay adjacent to one another (e.g., side by side, on top of one another). The first components may completely overlap or only portions of the components may overlap with one another. For example, as shown illustratively in FIGS. 9D and 9E, component 20C may extend further than component 20B such that a portion of component 20C is not overlapping or covered by component 20B. In some cases, this configuration can be advantageous where component 20C is substantially transparent and requires light to travel through a portion of the component (e.g., a reaction area, measurement zone, or detection region), and where component 20B is opaque or less transparent than component 20C.

Furthermore, the first and second components may include any suitable shape and/or configuration. For instance, in some embodiments, the first component includes a feature complementary to a feature of the second component, so as to form a non-fluidic connection between the first and second components. The complementary features may, for example, aid alignment of the first and second components during assembly. Examples of complementary features are described herein. In some cases, coupling or mating mechanisms, such as those described herein, can be used to couple the first and second components.

The first and second components may be integrally connected to one another in some embodiments. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, or separating components fastened together via adhesives or tools. Integrally connected components may be irreversibly attached to one another during the course of normal use. For example, components 20B and 20C may be integrally connected by use of an adhesive or by other bonding methods. In other embodiments, two or more components of a cassette may be reversibly attached to one another.

As described herein, in some embodiments at least a first component and a second component forming a composite cassette may be formed in different materials. The system may be designed such that the first component includes a first material that aids or enhances one or more functionalities of the first component. For example, if the first component is designed to store a liquid reagent (e.g., in a channel of the component) prior to first use by a user (e.g., for at least a day, a week, a month, or a year), the first material may be chosen to have a relatively low vapor permeability so as to reduce the amount of evaporation of the stored liquid over time. It should be understood, however, that the same materials may be used for multiple components (e.g., layers) of a cassette in some embodiments. For instance, both first and second components of a cassette may be formed in a material having a low water vapor permeability.

A material used to form all or portions of a section or component of a device may have, for example, a water vapor permeability of less than about 5.0 g·mm/m$^2$·d, less than about 4.0 g·mm/m$^2$·d, less than about 3.0 g·mm/m$^2$·d, less than about 2.0 g·mm/m$^2$·d, less than about 1.0 g·mm/m$^2$·d, less than about 0.5 g·mm/m$^2$·d, less than about 0.3 g·mm/m$^2$·d, less than about 0.1 g·mm/m$^2$·d, or less than about 0.05 g·mm/m$^2$·d. In some cases, the water vapor permeability may be, for example, between about 0.01 g·mm/m$^2$·d and about 2.0 g·mm/m$^2$·d, between about 0.01 g·mm/m$^2$·d and about 1.0 g·mm/m$^2$·d, between about 0.01 g·mm/m$^2$·d and about 0.4 g·mm/m$^2$·d, between about 0.01 g·mm/m$^2$·d and about 0.04 g·mm/m$^2$·d, or between about 0.01 g·mm/m$^2$·d and about 0.1 g·mm/m$^2$·d. The water vapor permeability may be measured at, for example, 40° C. at 90% relative humidity (RH).

In some embodiments, a second component is not used to store a liquid prior to use by a user and may be formed in a second material having a higher water vapor permeability than that of the first component. For example, the second material may have a water vapor permeability of greater than about 0.05 g·mm/m$^2$·d, greater than about 0.1 g·mm/m$^2$·d, greater than about 0.3 g·mm/m$^2$·d, greater than about 0.5 g·mm/m$^2$·d, greater than about 1.0 g·mm/m$^2$·d, greater than about 2.0 g·mm/m$^2$·d, greater than about 3.0 g·mm/m$^2$·d, greater than about 4.0 g·mm/m$^2$·d, or greater than about 5.0 g·mm/m$^2$·d.

In some cases, a first material used to form a first component of a cassette has a water vapor permeability at least 1.5×, at least 2×, at least 3×, at least 5×, at least 10×, at least 20×, at least 50×, or at least 100× lower than that of a second material used to form a second component of a cassette.

Water vapor permeabilities of materials are known or can be determined by those of ordinary skill in the art. Materials such as certain cyclo-olefin copolymers, for example, typically have a water vapor permeability of less than about 0.1 g·mm/m²·d (e.g., between 0.02-0.04 g·mm/m²·d), whereas certain polypropylenes have a water vapor permeability of about 0.5 g·mm/m²·d or greater. Certain PETs have a water vapor permeability of about 1.0 g·mm/m²·d, certain PVCs have a water vapor permeability of about 1.2 g·mm/m²·d, and certain polycarbonates have a water vapor permeability of about 4.0 g·mm/m²·d.

In some embodiments, one or more components or layers of a device may be formed in a material that makes it more suitable for processing under certain conditions. For example, a material may be chosen in part based on its melting temperature to allow it to be compatible with certain fabrication tools and/or methods (e.g., for forming channels of certain dimensions) such as those described herein. In some embodiments, a first component is formed in a material having a melting temperature of greater than about 80° C., greater than about 100° C., greater than about 130° C., greater than about 160° C., or greater than about 200° C. In certain embodiments, a second component designed to be combined with the first component may be formed in a material having a melting temperature of less than or equal to about 200° C., less than or equal to about 160° C., less than or equal to about 130° C., less than or equal to about 100° C., or less than or equal to about 80° C. Other melting temperatures are also possible.

In one particular set of embodiments, component 20B is formed of a material having a higher melting temperature than the material used to form component 20C. In one particular embodiment, a component used for storage of a liquid reagent is formed in a material having a higher melting temperature than a material used to form another component of the cassette.

In certain embodiments, a cassette including first and second components have channel portions of different cross-sectional dimensions in each of the different components. As described herein, the particular cross-sectional dimensions may be chosen based in part on the function(s) of the channel portions, where the channel portions are positioned relative to other parts or components of the device, and other factors.

A channel portion of a cassette may have any suitable cross-sectional dimension. For example, a first component may include a first channel including at least one portion having a cross-sectional dimension of, for example, greater than about 50 microns, greater than about 100 microns, greater than about 200 microns, greater than about 350 microns, greater than about 500 microns, greater than about 750 microns or greater than about 1 mm. In some cases, a channel portion having a relatively large cross-sectional dimension may be used to store a liquid contained therein prior to first use by a user.

In some cases, a second component of a cassette may include a second channel including at least one portion having a cross-sectional dimension that is at least 1.5 times, at least 2 times, at least 3 times, at least 5 times, at least 7 times or at least 10 times different than the cross-sectional dimension of a first channel portion of a first component of the cassette. Such differences in cross-sectional dimensions may be due to the different functionality of the second channel portion in the second component compared to that of the first component. The second channel of the second component may include at least one portion having a cross-sectional dimension of, for example, less than about 1 mm, less than about 750 microns, less than about 500 microns, less than about 350 microns, less than about 200 microns, less than about 100 microns or less than about 50 microns. For example, in some cases, a channel having a relatively smaller cross-sectional dimension than that of a first channel of a first component may be suitable for a detection region of the device, for controlling rates of fluid flow, or for other purposes.

In some embodiments, channel portions in different components of a cassette have different cross-sectional dimensions and are formed in materials having different melting temperatures. For example, in some instances, a channel portion having a relatively small cross-sectional dimension (e.g., less than about 300 microns, less than about 200 microns, or less than about 100 microns) may be formed in a material having a relatively low melting temperature (e.g., less than about 100° C.), whereas a channel portion having a relatively larger cross-sectional dimension (e.g., greater than about 100 microns, greater than about 200 microns, or greater than about 300 microns) may be formed in a material having a relatively higher melting temperature (e.g., greater than about 100° C.).

In certain cases, channels from different components or layers of a device may have different surface roughness. For example, a channel that is designed to be part of a detection region may have a lower surface roughness than a channel that is not used in a detection process or is used in a detection process that requires less sensitivity. Substantial roughness on the surface of a channel portion may result in unwanted scattering or redirection of light at an undesired angle. Channels from different components or layers of a device having different surface roughness may be advantageous because a channel having a relatively low surface roughness may be more complicated and/or more expensive to fabricate than a channel having a higher surface roughness. For example, certain fabrication tools for molding made by micromachining or lithography techniques have less surface roughness (and, therefore, form channel portions having less surface roughness) compared to tools made by machining, but may be more complicated and/or expensive to fabricate.

In some embodiments, at least a portion of a first channel of a first component may have a root mean square surface (RMS) roughness of less than about less than or equal to about 10 microns. In certain embodiments, the RMS surface roughness may be, for example, less than or equal to about 5 microns, less than or equal to about 3 microns, less than or equal to about 1 micron, less than or equal to about 0.8 microns, less than or equal to about 0.5 microns, less than or equal to about 0.3 microns, or less than or equal to about 0.1 microns. RMS surface roughness is a term known to those skilled in the art, and may be expressed as:

$$\sigma_h = [\langle(z-z_m)^2\rangle]^{1/2} = \left[\frac{1}{A}\int_A (z-z_m)^2 dA\right]^{1/2}$$

where A is the surface to be examined, and $|z-z_m|$ is the local height deviation from the mean.

At least a portion of a second channel of a second component may have, for example, a root mean square surface roughness different from that of the first component. The second channel portion may have a RMS surface roughness of, for example, greater than about 0.1 microns, greater than about 0.3 microns, greater than about 0.5 micron, greater than about 1 micron, greater than about 3 microns, greater than about 5 microns, or greater than about 10 microns.

In certain embodiments, first and second components of a cassette have different degrees of optical clarity. For example, a first component may be substantially opaque, and a second component may be substantially transparent. The substantially transparent component may be suitable for optical detection of a sample or analyte contained within the component.

In one set of embodiments, a material used form a component (e.g., a first or a second component) of a cassette has an optical transmission of greater than 90% between 400 and 800 nm wavelengths of light (e.g., light in the visible range). Optical transmission may be measured through a material having a thickness of, for example, about 2 mm (or in other embodiments, about 1 mm or about 0.1 mm). In some instances, the optical transmission is greater than 80%, greater than 85%, greater than 88%, greater than 92%, greater than 94%, or greater than 96% between 400 and 800 nm wavelengths of light. Another component of the device may be formed in a material having an optical transmission of less than 96%, less than 94%, less than 92%, less than 90%, less than 85%, less than 80%, less than 50%, less than 30%, or less than 10% between 400 and 800 nm wavelengths of light.

As described herein, different components or layers of a device may include channels made by different (or the same) fabrication tools and/or methods. For instance, injection molding may be used to form one component, and a different technique (e.g., machining) may be used to form another component. In another example, a first channel portion of a first component may be formed by a molding (e.g., injection molding) process involving the use of a fabrication tool made by milling or by a lithography process. In some cases, channel portions formed by a fabrication tool made by milling may have a substantially rounded cross-sectional area, whereas channel portions formed by fabrication tool made by a lithography process may have a substantially trapezoidal cross-sectional area. Other methods for forming channel portions having substantially rounded cross-sectional areas, substantially trapezoidal cross-sectional areas, or cross-sectional shapes, are also possible. Advantages and further description of channel portions having different cross-sectional shapes are described in more detail in U.S. patent application Ser. No. 12/640,420, published as U.S. Patent Publication No. 2010/0158756, filed Dec. 17, 2009, entitled, "Reagent Storage in Microfluidic Systems and Related Articles and Methods", which is incorporated herein by reference in its entirety. A second channel portion of a second component may be formed using a fabrication tool made by the same or a different method, and/or may have the same or different cross-sectional shape compared to a channel portion of a first component.

As described herein, in some embodiments a channel of a first component of a cassette is not in fluid communication with a channel of a second component of a cassette prior to first use by a user. For instance, even after mating of the two components, as shown illustratively in FIG. 9D, channels 206 and 207 are not in fluid communication with one another. However, the cassette may further include other parts or components such as fluidic connector alignment element 202 (FIG. 9E), which can attach to first and/or second components 20B and 20C or to other portions of the cassette. As described herein, the fluidic connector alignment element may be configured to receive and mate with fluidic connector 220, which can allow fluid communication between channels 206 and 207 of the first and second components, respectively. For example, the fluidic connector may include a fluid path including a fluid path inlet and a fluid path outlet, wherein the fluid path inlet can be fluidically connected to the outlet of channel 206 and the fluid path outlet can be fluidically connected to the inlet of channel 207 (or vice versa). The fluid path of the fluidic connector may have any suitable length (e.g., at least 1 cm, at least 2 cm, at least 3 cm, at least 5 cm) for connecting the channels. The fluidic connector may be a part of a kit along with a cassette, and packaged such that the fluidic connector is not fluidically connecting channels 206 and 207.

A fluidic connector may have any suitable configuration with respect to a cassette, or components of a cassette. As shown illustratively in FIG. 9E, upon connection of the fluidic connector to the cassette, the fluidic connector may be positioned on a side of a component (e.g., component 20B) opposite another component (e.g., component 20C). In other embodiments, a fluidic connector can be positioned between two components of a cassette. For instance, the fluidic connector may be a component or layer positioned between (e.g., sandwiched between) two components of the cassette. Other configurations are also possible.

Additionally, a fluidic connector may lie substantially perpendicular to one or more components or layers of a cassette, e.g., as shown illustratively in FIG. 9E. In other embodiments, a fluidic connector may lie substantially parallel to (e.g., on top of or flat against) one or more components of a cassette. Other configurations are also possible.

In some cases, an alignment element and/or a fluidic connector is physically connected to only a single component of a multi-component cassette, while in other cases, an alignment element and/or a fluidic connector is physically connected to multiple components of a multi-component cassette. In certain embodiments, a portion of a component of the cassette that is physically connected to an alignment element and/or a fluidic connector has a certain thickness to allow suitable connection. For example, where the fluidic connector is designed to be inserted into an inlet and an outlet of channels of a cassette, the cassette at the insertion region may have a certain (e.g., minimal) thickness. The cassette, or one or more components of a cassette, at a region designed for connection with a fluidic connector may be, for example, have a thickness of at least 1 cm, at least 1.5 cm, at least 2 cm, at least 2.5, at least 3 cm, at least 4 cm, or at least 5 cm. Other portions of the cassette (or components of the cassette) not designed for connection with an alignment element and/or a fluidic connector may have a thickness of, for example, less than 5 cm, less than 4 cm, less than 3 cm, less than 2.5 cm, less than 2 cm, less than 1.5 cm, less than 1 cm, less than 0.5 cm, or less than 0.1 cm.

Although much of the description herein is directed towards a cassette having one or more components or layers including channel networks, in other embodiments, a cassette may include more than 2, more than 3, or more than 4 such components or layers. For example, as shown illustratively in FIG. 9F, a cassette may include components 20B, 20C, 20D, and 20E, each including at least one channel or network of channels. In some instances, the channel(s) of one or more components (e.g., 2, 3, or all components) may be fluidically unconnected prior to first use, but may be connected fluidically at first use, e.g., by use of a fluidic connector. In other embodiments, the channel(s) of one or more components (e.g., 2, 3, or all components) are connected fluidically prior to first use.

As described herein, each of the components or layers of a cassette may be designed to have a specific function that is different from a function of another component of the cassette. In other embodiments, two or more components may have the same function. For example, as shown in the illustrative embodiment of FIG. 9F, each of components 20C, 20D and 20E may have multiple measurement zones 209 connected in series. Upon connection of fluidic connector 222 to the composite cassette, portions of a sample (or multiple samples) may be introduced into the channel network in each of components 20C, 20D and 20E to perform multiple analyses.

In some embodiments, at least first and second components of a cassette may be a part of a device or a kit used for determining a particular chemical or biological condition. The device or kit may include, for example, a first component comprising a first channel in a first material, the first channel including an inlet, an outlet and, between the first inlet and outlet, at least one portion having a cross-sectional dimension greater than 200 microns. The device or kit may also include a second component comprising a second channel in a second material, the second channel including an inlet, an outlet and, between the second inlet and outlet, at least one portion having a cross-sectional dimension less than 200 microns. In some cases, the device or kit is packaged such that the first and second components are connected to one another. For example, the first and second components may be integrally connected to one another. In other embodiments, the first and second components are reversibly attached to one another. The device or kit may further include a fluidic connector for fluidically connecting the first and second channels, the fluidic connector comprising a fluid path, including a fluid path inlet and a fluid path outlet, wherein the fluid path inlet can be fluidically connected to the outlet of the first channel and the fluid path outlet can be fluidically connected to the inlet of the second channel. In some embodiments, the device or kit is packaged such that the fluidic connector is not fluidically connecting the first and second channels in the package. Upon first use of the device by an intended user, the fluidic connector can be used to bring the first and second channels into fluid communication with one another.

As described herein, a device or kit may include channel portions on different components of a cassette that may differ from one another. As such, in certain embodiments, a device comprises one or more of the following features: the first material used to form a first channel portion of a first component is different from a second material used to form a second channel portion of a second component; the first channel portion has a different cross-sectional shape from that of the second channel portion; and/or the first channel portion has a different RMS surface roughness than that of the second channel portion. Channel portions may also have other differences as described herein.

A cassette described herein may have any suitable volume for carrying out an analysis such as a chemical and/or biological reaction or other process. The entire volume of a cassette includes, for example, any reagent storage areas, measurement zones, liquid containment regions, waste areas, as well as any fluid connectors, and fluidic channels associated therewith. In some embodiments, small amounts of reagents and samples are used and the entire volume of the fluidic device is, for example, less than 10 mL, 5 mL, 1 mL, 500 µL, 250 µL, 100 µL, 50 µL, 25 µL, 10 µL, 5 µL, or 1 µL.

A cassette described herein may be portable and, in some embodiments, handheld. The length and/or width of the cassette may be, for example, less than or equal to 20 cm, 15 cm, 10 cm, 8 cm, 6 cm, or 5 cm. The thickness of the cassette may be, for example, less than or equal to 5 cm, 3 cm, 2 cm, 1 cm, 8 mm, 5 mm, 3 mm, 2 mm, or 1 mm. Advantageously, portable devices may be suitable for use in point-of-care settings.

It should be understood that the cassettes and their respective components described herein are exemplary and that other configurations and/or types of cassettes and components can be used with the systems and methods described herein.

The methods and systems described herein may involve variety of different types of analyses, and can be used to determine a variety of different samples. In some cases, an analysis involves a chemical and/or biological reaction. In some embodiments, a chemical and/or biological reaction involves binding. Different types of binding may take place in cassettes described herein. Binding may involve the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some cases, a heterogeneous reaction (or assay) may take place in a cassette; for example, a binding partner may be associated with a surface of a channel, and the complementary binding partner may be present in the fluid phase. Other solid-phase assays that involve affinity reaction between proteins or other biomolecules (e.g., DNA, RNA, carbohydrates), or non-naturally occurring molecules, can also be performed. Non-limiting examples of typical reactions that can be performed in a cassette include chemical reactions, enzymatic reactions, immuno-based reactions (e.g., antigen-antibody), and cell-based reactions.

Non-limiting examples of analytes that can be determined (e.g., detected) using cassettes described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g., thyroid stimulating hormone (TSH), thyroxine (T4), luteinizing hormone (LH), follicle-stimulating hormones (FSH), testosterone, progesterone, human chorionic gonadotropin, estradiol; other proteins or peptides, e.g. troponin I, c-reactive protein, myoglobin, brain natriuretic protein, prostate specific antigen (PSA), free-PSA, complexed-PSA, pro-PSA, EPCA-2, PCADM-1, ABCA5, hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Typical sample fluids include physiological fluids such as human or animal whole blood, blood serum, blood plasma, semen, tears, urine, sweat, saliva, cerebrospinal fluid, vaginal secretions; in-vitro fluids used in research or environmental fluids such as aqueous liquids suspected of being contaminated by the analyte.

In some embodiments, one or more reagents that can be used to determine an analyte of a sample (e.g., a binding partner of the analyte to be determined) is stored in a channel or chamber of a cassette prior to first use in order to perform a specific test or assay. In cases where an antigen is being analyzed, a corresponding antibody or aptamer can be the binding partner associated with a surface of a microfluidic channel. If an antibody is the analyte, then an appropriate antigen or aptamer may be the binding partner associated with the surface. When a disease condition is being determined, it may be preferred to put the antigen on the surface and to test for an antibody that has been produced in the subject. Such antibodies may include, for example, antibodies to HIV.

In some embodiments, a cassette is adapted and arranged to perform an analysis involving accumulating an opaque material on a region of a microfluidic channel, exposing the region to light, and determining the transmission of light through the opaque material. An opaque material may include a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than, for example, 90, 80, 70, 60, 50, 40, 30, 20, 10 or 1 percent of the light illuminating the opaque material. Examples of opaque materials include molecular layers of metal (e.g., elemental metal), ceramic layers, polymeric layers, and layers of an opaque substance (e.g., a dye). The opaque material may, in some cases, be a metal that can be electrolessly deposited. These metals may include, for example, silver, copper, nickel, cobalt, palladium, and platinum.

An opaque material that forms in a channel may include a series of discontinuous independent particles that together form an opaque layer, but in one embodiment, is a continuous material that takes on a generally planar shape. The opaque material may have a dimension (e.g., a width of length) of, for example, greater than or equal to 1 micron, greater than or equal to 5 microns, greater than 10 microns, greater than or equal to 25 microns, or greater than or equal to 50 microns. In some cases, the opaque material extends across the width of the channel (e.g., a measurement zone) containing the opaque material. The opaque layer may have a thickness of, for example, less than or equal to 10 microns, less than or equal to 5 microns, less than or equal to 1 micron, less than or equal to 100 nanometers or less than or equal to 10 nanometers. Even at these small thicknesses, a detectable change in transmittance can be obtained. The opaque layer may provide an increase in assay sensitivity when compared to techniques that do not form an opaque layer.

In one set of embodiments, a cassette described herein is used for performing an immunoassay (e.g., for human IgG or PSA) and, optionally, uses silver enhancement for signal amplification. A cassette described herein may have one or more similar characteristics as those described in U.S. patent application Ser. No. 12/113,503, published as U.S. Patent Publication No. 2008/0273918, filed May 1, 2008 and entitled "Fluidic Connectors and Microfluidic Systems", which is incorporated herein by reference. In such an immunoassay, after delivery of a sample containing human IgG to a reaction site or analysis region, binding between the human IgG and anti-human IgG can take place. One or more reagents, which may be optionally stored in a channel of the device prior to use, can then flow over this binding pair complex. One of the stored reagents may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone, chlorohydroquinone, pyrogallol, metol, 4-aminophenol and phenidone), which can optionally be stored in different channels prior to use.

As a positive or negative pressure differential is applied to the system, the silver salt and reducing solutions can merge at a channel intersection, where they mix (e.g., due to diffusion) in a channel, and then flow over the analysis region. Therefore, if antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. An opaque layer that is formed in the channel can be detected optically, for example, by measuring a reduction in light transmittance through a portion of the analysis region (e.g., a serpentine channel region) compared to a portion of an area that does not include the antibody or antigen. Alternatively, a signal can be obtained by measuring the variation of light transmittance as a function of time, as the film is being formed in an analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

Various types of fluids can be used with the cassettes described herein. As described herein, fluids may be introduced into the cassette at first use, and/or stored within the cassette prior to first use. Fluids include liquids such as solvents, solutions and suspensions. Fluids also include gases and mixtures of gases. When multiple fluids are contained in a cassette, the fluids may be separated by another fluid that is preferably substantially immiscible in each of the first two fluids. For example, if a channel contains two different aqueous solutions, a separation plug of a third fluid may be substantially immiscible in both of the aqueous solutions. When aqueous solutions are to be kept separate, substantially immiscible fluids that can be used as separators may include gases such as air or nitrogen, or hydrophobic fluids that are substantially immiscible with the aqueous fluids. Fluids may also be chosen based on the fluid's reactivity with adjacent fluids. For example, an inert gas such as nitrogen may be used in some embodiments and may help preserve and/or stabilize any adjacent fluids. An example of an substantially immiscible liquid for separating aqueous solutions is perfluorodecalin. The choice of a separator fluid may be made based on other factors as well, including any effect that the separator fluid may have on the surface tension of the adjacent fluid plugs. It may be preferred to maximize the surface tension within any fluid plug to promote retention of the fluid plug as a single continuous unit under varying environmental conditions such as vibration, shock and temperature variations. Separator fluids may also be inert to an reaction site (e.g., measurement zone) to which the fluids will be supplied. For example, if a reaction site includes a biological binding partner, a separator fluid such as air or nitrogen may have little or no effect on the binding partner. The use of a gas (e.g., air) as a separator fluid may also provide room for expansion within a channel of a fluidic device should liquids contained in the device expand or contract due to changes such as temperature (including freezing) or pressure variations.

As set forth in greater detail below, the microfluidic sample analyzer 100 may include a fluid flow source 40 (e.g., a pressure-control system) which may be fluidly connected to the channels 206, 207, 222 to pressurize the channels to move the sample and/or other reagents through the channels. In particular, the fluid flow source 40 may be configured to move a sample and/or reagent initially from the substantially U-shaped channel 222 into the first channel 206. The fluid flow source 40 may also be used to move the reagents in the second channel 207 through the substantially U-shaped channel 222 and into the first channel 206. After the sample and reagents pass through the measurement zones 209 and are analyzed, the fluid flow source 40 may be configured to move the fluids into the absorbent material 217 of the cassette 200. In one embodiment, the fluid flow source is a vacuum system. It should be understood, however, that other sources of fluid flow such as valves, pumps, and/or other components can be used.

The top view of a cassette 20 in FIG. 9A illustrates many of the components discussed above, except that in this embodiment, the channels 206, 207 within the cassette housing are configured differently than in the schematic view shown in FIG. 8. In one embodiment, the cassette housing includes at least one surface configured to interact with a microfluidic sample analyzer such that the cassette may be inserted into and retained within the analyzer. In one embodiment, as illustrated in FIG. 9A, the housing includes a cammed surface along a side portion of the cassette 20. In this particular embodiment, the cammed surface includes a notch 230 formed at one end of the cassette 20. The other end of the cassette 20 includes a curved corner surface 232. As set forth in greater detail below, this cammed surface of the cassette may be configured to interact with the sample analyzer 100 such that the analyzer 100 can detect the presence of the cassette 20 within the housing 10 and/or position the cassette 20 within the analyzer 100. In particular, the curved corner surface may be configured to contact a portion of the analyzer, such as an arm, and the notch may be configured to retain that portion of the analyzer to retain the cassette within the analyzer.

Figure 10:
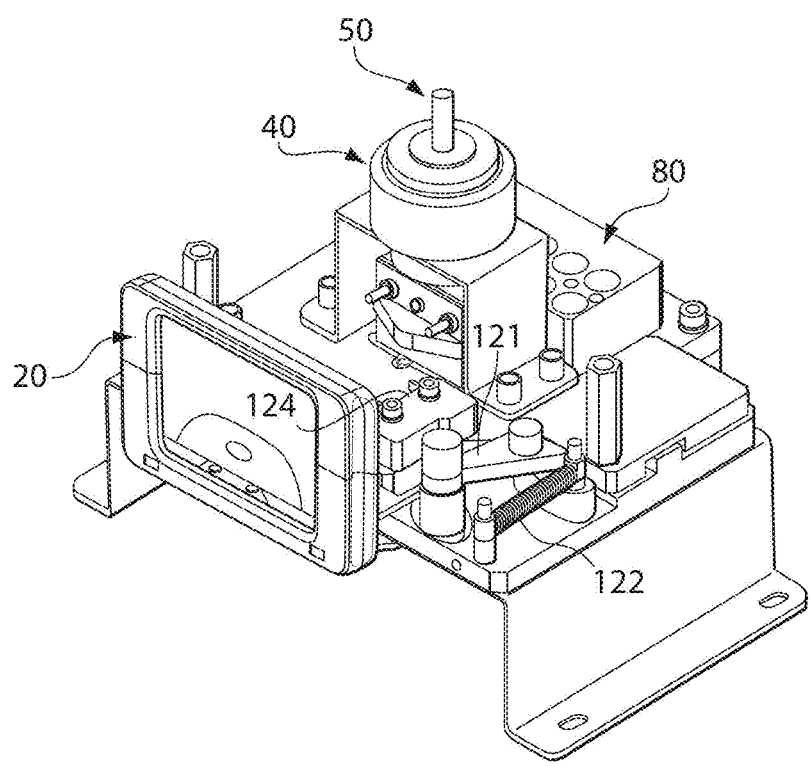
FIG. 10 is a partial assembly view of a sample analyzer according to one embodiment.
Figure 11:
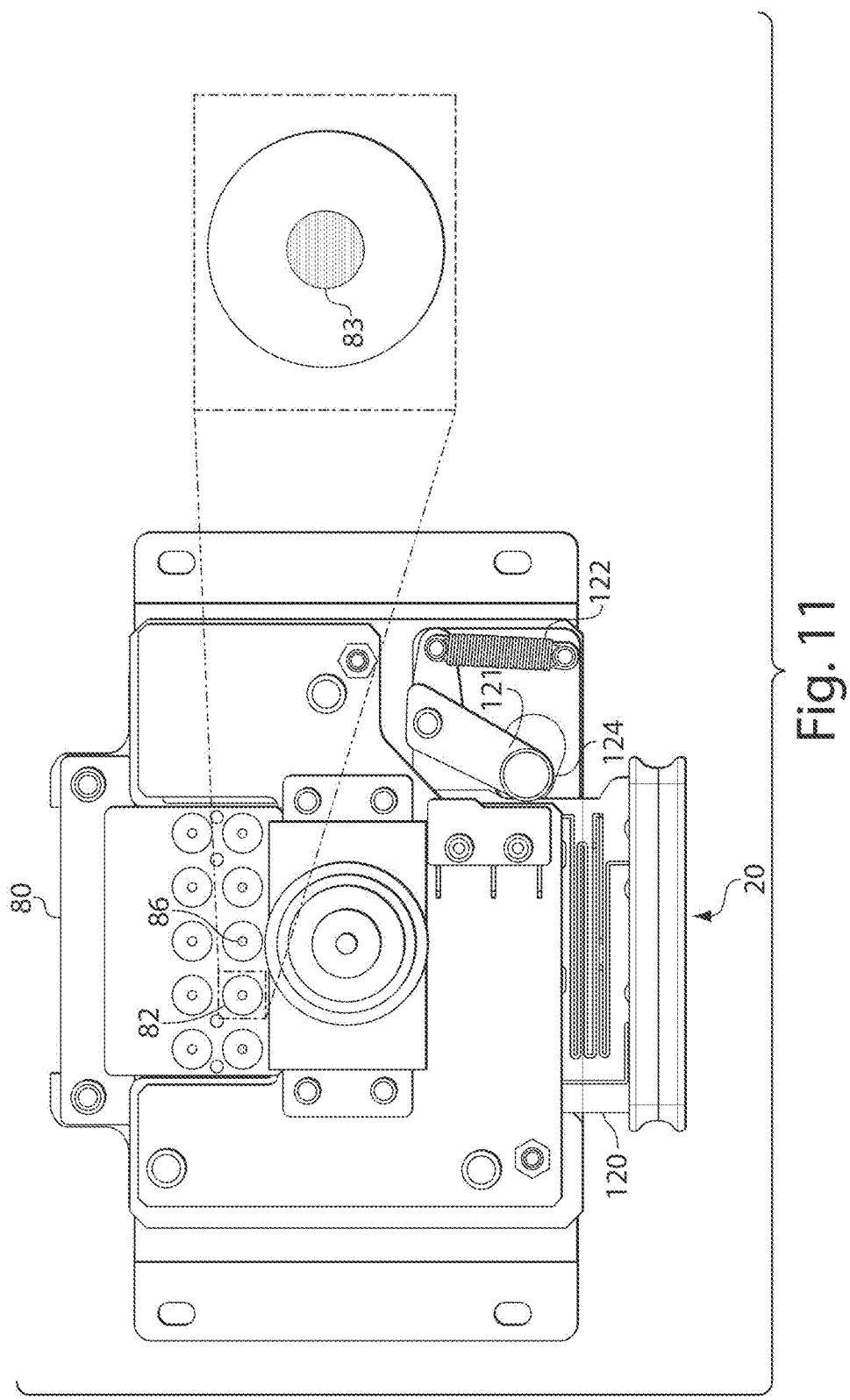
FIG. 11 is a top view of a partial assembly of a sample analyzer according to one embodiment.
Figure 12:
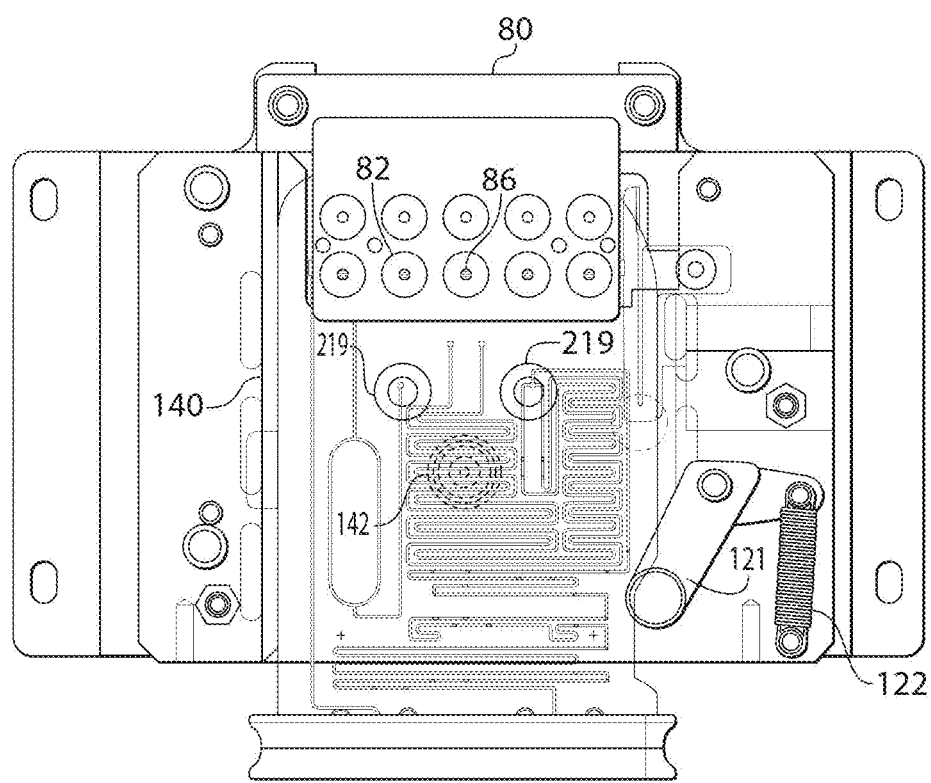
FIG. 12 is another top view of a partial assembly of a sample analyzer according to one embodiment.
Figure 13:
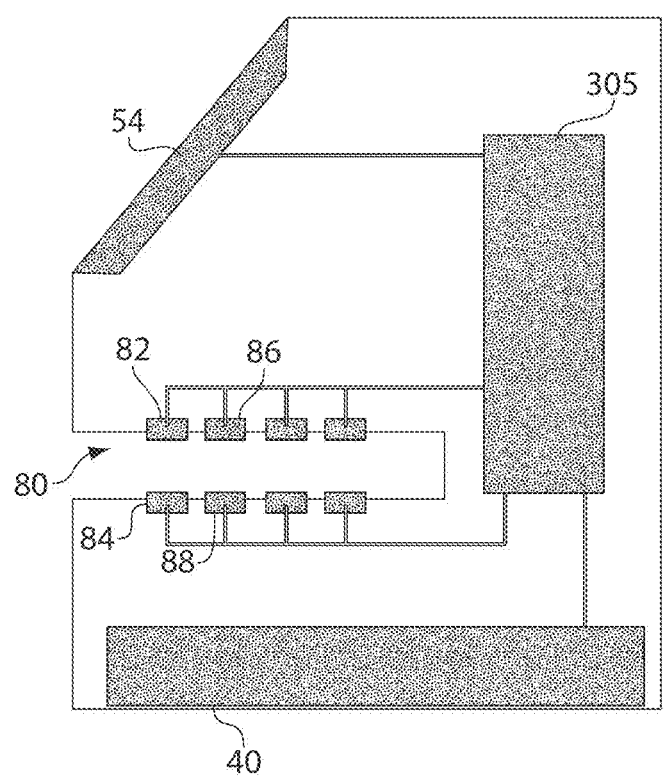
FIG. 13 is a schematic view of a portion of a sample analyzer according to one embodiment.

Turning now to FIGS. 10-12, internal components of the sample analyzer 100 will now be discussed. In the sub-assembly views of FIGS. 10-12, a cassette 20 is shown inserted into the opening 120 in the housing. In one embodiment, the housing 101 includes a component configured to interface with and engage a mating component on the cassette. In this particular illustrated embodiment, the housing 101 includes an arm 121 positioned within the housing that is configured to engage the cammed surface on the cassette discussed above. In a first position, the arm 121 extends at least partially into the opening 120 in the housing such that as the cassette 20 is inserted into the opening 120, the arm is pushed away from the opening 120 into a second position allowing the cassette 20 to enter the opening 120.

The arm 121 may be configured to contact a side surface of the cassette as the cassette is inserted into the opening 120. As shown in FIG. 9A, the end of the cassette 20 may include a curved surface 232 which may provide a smooth transition for the arm 121 to contact the side surface of the cassette. In one embodiment, the arm 121 is coupled to a spring 122 to make the arm spring loaded such that it will press against the side surface of the cassette when the cassette is within the analyzer 100. In particular, the spring loaded arm is urged back towards and, in certain embodiments essentially into the first position. In one embodiment, the end of the arm 121 includes a roller 124 which engages the side surface of the cassette 20. The roller 124 may be configured to minimize friction between the two components as the cassette is inserted into position. As shown in FIGS. 11 and 12, once the arm 121 engages the notch 230, the arm 121 is pushed back out to its first position due to the bias of the spring 122. Once the arm 121 engages this inwardly cammed surface, the cassette 20 is positioned and retained within the housing 10 of the analyzer 100, and the bias of the spring 122 prevents the cassette 20 from slipping out of the analyzer.

It should be appreciated that the spring loaded arm 121 in the analyzer 100 and the notch 230 on the cassette 20 may be configured to detect and position the cassette 20 in the analyzer. As set forth below, it should also be recognized that this arrangement may help to indicate to a user that the cassette 20 is positioned correctly in the analyzer and is ready to be analyzed and processed. After the analysis is conducted, a user may remove the cassette 20 from the analyzer 100 by pulling the cassette 20 out of the opening 120. The user may either exert a force that would overcome the bias of the spring 122 and/or the analyzer 100 may be configured with an unlocking mechanism (not shown) to move the arm 121 into its second position such that it is no longer in contact with the notch 230 on the cassette 20.

In one embodiment, an electronic position switch indicates when the roller 124 on the arm 121 is pushed out into its second position (e.g., as the cassette 20 is being inserted into the analyzer). The electronic position switch may also indicate when the roller returns back towards/to its first position (e.g., either when there is no cassette within the analyzer or when the cassette is fully inserted into the analyzer and the roller is engaged within the notch 230). Another position switch may be configured to indicate when the cassette is fully inserted and accurately positioned within the analyzer 100. Thus, the switch may be used to indicate to a user that the cassette 20 is positioned correctly in the analyzer. These various cassette sensors 410 are shown in the schematic diagram shown in FIG. 16, which is discussed in greater detail below.

Many mechanical and electro-mechanical techniques can be used to reliably load and unload the cassette. For example, a tray, such as that found in a CD player, may hold a cassette and slide in and out of the analyzer. This sliding can be accomplished by hand or by a motor (e.g., directly driving the tray or by use of pulleys). Another example of loading and unloading the cassette includes the use of a motorized unit that is in physical contact with the cassette. For instance, the motorized unit may mate with the cassette through friction one or more sides and/or a top and/or bottom of the cassette. In some cases, the unit may mate with the cassette with gear teeth fabricated on the side of the cassette.

Figure 15:
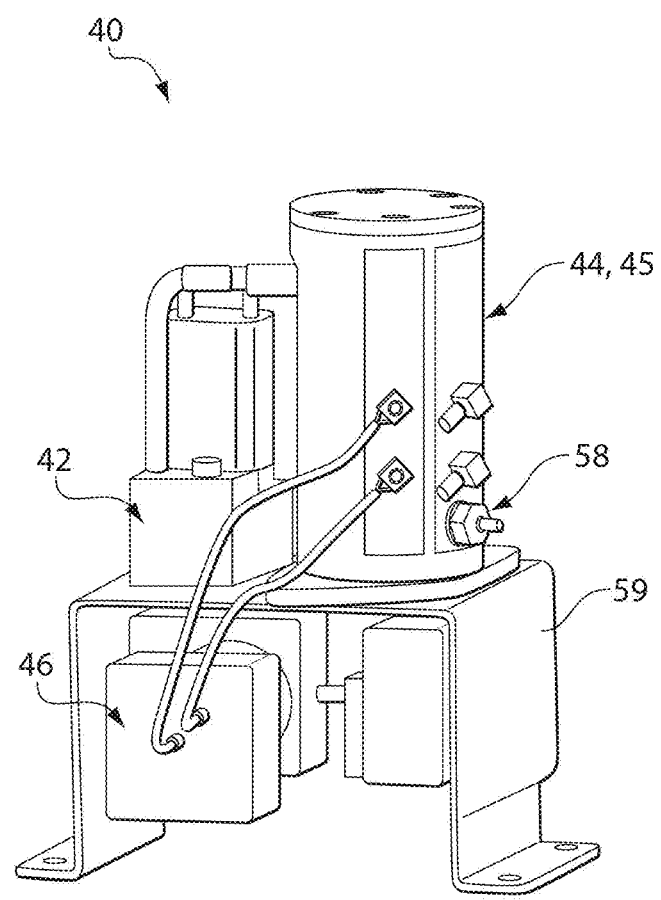
FIG. 15 is a perspective view of a vacuum system of a sample analyzer according to one embodiment.

FIG. 10 also illustrates a portion of a fluid flow source 40 which may be configured to pressurize the channel 206 (and channel 207 if fluidly connected to 206) in the cassette 20 to move a sample through the channel. FIG. 15 also illustrates a fluid flow source 40. In one illustrative embodiment, the fluid flow source 40 is a vacuum system and includes a vacuum source or pump 42, two vacuum reservoirs 44, 45 which may be separated by a vacuum regulator 46 and a manifold 48 to provide a fluid connection between the vacuum reservoirs 44 and the cassette 20. The manifold 48 may also include one or more fluid connections to one or more ports on the cassette. For example, the manifold may provide a fluidic connection between port 213 and a valve (such as a solenoid valve). Opening and closing this valve may control where air can enter the cassette, thus serving as a vent valve in certain embodiments.

As mentioned above, in one embodiment, the vacuum source 42 is a pump, such as a solenoid operated diaphragm pump. In other embodiments, fluid flow may be driven/controlled via use of other types of pumps or sources of fluid flow. For example, in one embodiment, a syringe pump may be used to create a vacuum by pulling the syringe plunger in an outward direction. In other embodiments, a positive pressure is applied to one or more inlets of the cassette to provide a source of fluid flow.

In some embodiments, fluid flow takes place while applying a substantially constant non-zero pressure drop (i.e., $\Delta P$) across an inlet and an outlet of a cassette. In one set of embodiments, an entire analysis is performed while applying a substantially constant non-zero pressure drop (i.e., $\Delta P$) across an inlet and an outlet of a cassette. A substantially constant non-zero pressure drop can be achieved, for example, by applying a positive pressure at the inlet or a reduced pressure (e.g., a vacuum) at the outlet. In some cases, a substantially constant non-zero pressure drop is achieved while fluid flow does not take place predominately by capillary forces and/or without the use of actuating valves (e.g., without changing a cross-sectional area of a channel of a fluid path of the cassette). In some embodiments, during essentially the entire analysis conducted in the cassette, a substantially constant non-zero pressure drop may be present across, for example, an inlet to a measurement zone (which may be connected to a fluidic connector) and an outlet downstream of the measurement zone (e.g., an outlet downstream of a liquid containment region), respectively.

In one embodiment, a vacuum source is configured to pressurize a channel to approximately −60 kPa (approximately ⅔ atmosphere). In another embodiment, the vacuum source is configured to pressurize a channel to approximately −30 kPa. In certain embodiments, a vacuum sources is configured to pressurize a channel to, for example, between −100 kPa and −70 kPa, between −70 kPa and −50 kPa, between −50 kPa and −20 kPa, or between −20 kPa and −1 kPa.

As mentioned above, in one embodiment, two vacuum reservoirs 44, 45 may be provided. The pump may be turned on such that the first reservoir 44 may be pressurized to approximately −60 kPa. A regulator 46 positioned between reservoir 44 and 45 may ensure that the second reservoir 45 may only be pressurized to a different pressure, for example, approximately −30 kPa. This regulator may maintain the pressure of reservoir 45 at −30 kPa (or at another suitable pressure) as long as reservoir 44 remained at a certain pressure range, e.g., between −60 kPa and −30 kPa. Pressure sensors may monitor the pressure within each reservoir 44, 45. If the pressure in the first reservoir 44 reaches a set point (for example, approximately −40 kPa), the pump may be actuated to decrease the pressure in the first reservoir 44. The second reservoir 45 may be configured to detect any leaks in the overall vacuum system 40. As shown in FIG. 15, the vacuum system 40 may include a filter 58 coupled to the reservoirs 44, 45. A solenoid valve 59 is shown which serves as the vent valve connected through the manifold to port 213.

Figure 14:
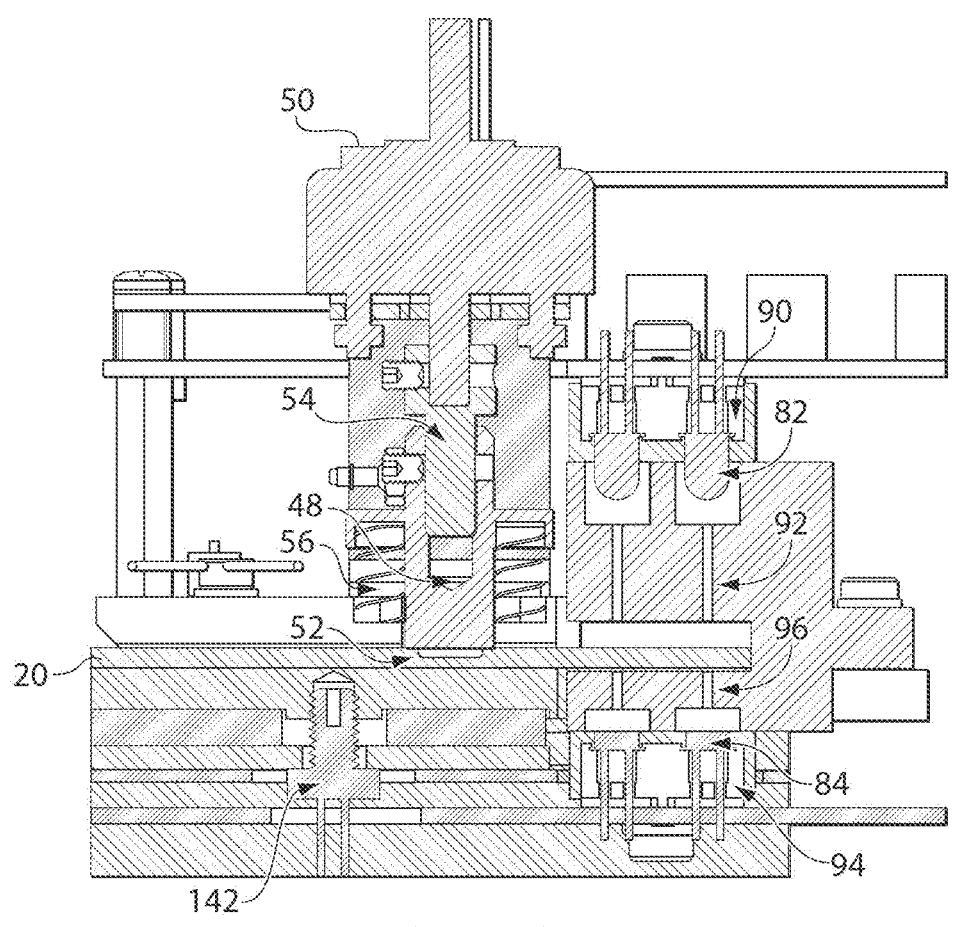
FIG. 14 is a schematic side view of a portion of a sample analyzer according to one embodiment.

Once the cassette 20 is positioned within the analyzer 100, the fluid flow source 40 may be coupled to the cassette 20 to ensure a fluid-tight connection. As mentioned above, the cassette 20 may include a port 219 configured to couple the channel 206, and channel 207 if fluidically connected to 206, with the fluid flow source 40. As shown in FIG. 14, in one embodiment, seals, or o-rings 52 are positioned around the port 219 and a linear solenoid 50 may be positioned above the o-rings 52 to press and seal the o-rings against the cassette body 200. As shown in FIG. 14, a manifold adapter 54 may be positioned between the linear solenoid 50 and the manifold 48, and passive return springs 56 may be provided around the manifold 48 to urge the manifold away from the cassette body 200 when the solenoid is not charged. In one embodiment, multiple ports on the cassette 20 may interface with the manifold 48. For example, as shown in the exemplary embodiment illustrated in FIG. 9A, in addition to the port 219, there may be two venting ports 215 and a mixing port 213. The interface between each port and the manifold may be independent (e.g., there may be no fluidic connection inside the manifold).

In one embodiment, when the fluid flow source 40 is activated, the channel 206, 207 in the cassette 20 may be pressurized (e.g., to approximately −30 kPa) which will drive the fluids within the channel (both fluid sample as well as reagents) toward the outlet. In an embodiment which includes the vent ports 215 and the mixing port 213, a vent valve 59 connected to port 213 through the manifold 48 may initially be open which may enable all of the reagents downstream of the mixing port 213 to move toward the outlet, but will not cause reagents upstream of the mixing port 213 to move. Configurations and uses of vent valves are described in more detail in U.S. Patent Apl. Ser. No. 61/263,981, filed Nov. 14, 2009 and entitled, "Fluid Mixing and Delivery in Microfluidic Systems, which is incorporated herein by reference in its entirety for all purposes. Once the vent valve is closed, reagents upstream of the mixing port 213 may move toward a mixing port and then to the outlet. For example, fluids can be stored serially in a channel upstream of the mixing port, and after closing a vent valve positioned along the channel, the fluids can flow sequentially towards the channel outlet. In some cases, fluids can be stored in separate, intersecting channels, and after closing a vent valve the fluids will flow together toward a point of intersection. This set of embodiments can be used, for example, to controllably mix the fluids as they flow together. The timing of delivery and the volume of fluid delivered can be controlled, for example, by the timing of the vent valve actuation.

Advantageously, vent valves can be operated without constricting the cross-section of the microfluidic channel on which they operate, as might occur with certain valves in the prior art. Such a mode of operation can be effective in preventing leaking across the valve. Moreover, because vent valves can be used, some systems and methods described herein do not require the use of certain internal valves, which can be problematic due to, for example, their high expense, complexity in fabrication, fragility, limited compatibility with mixed gas and liquid systems, and/or unreliability in microfluidic systems.

It should be understood that while vent valves are described, other types of valving mechanisms can be used with the systems and methods described herein. Non-limiting examples of a valving mechanism which may be operatively associated with a valve include a diaphragm valve, ball valve, gate valve, butterfly valve, globe valve, needle valve, pinch valve, poppet valve, or pinch valve. The valving mechanism may be actuated by any suitable means, including a solenoid, a motor, by hand, by electronic actuation, or by hydraulic/pneumatic pressure.

As previously mentioned, all of the liquids in the cassette 20 (sample and reagents) may move into the liquid containment area which may include an absorbent material 217. In one embodiment, the absorbent material absorbs only liquids such that gases may flow out of the cassette through the outlet.

A variety of determination (e.g., measuring, quantifying, detecting, and qualifying) techniques may be used, e.g., to analyze a sample component or other component or condition associated with a microfluidic system or cassette described herein. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. In other embodiments, determination techniques may measure conductivity or resistance. As such, an analyzer may be configured to include such and other suitable detection systems.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. In some embodiments, a system may be operated with a minimum of optical devices (e.g., a simplified optical detector). For instance, the determining device may be free of a photomultiplier, may be free of a wavelength selector such as a grating, prism or filter, may be free of a device to direct or columnate light such as a columnator, or may be free of magnifying optics (e.g., lenses). Elimination or reduction of these features can result in a less expensive, more robust device.

FIGS. 10-14 illustrate an exemplary optical system 80 which may be positioned in the housing 10 of the analyzer 100. As shown illustratively in these embodiments, the optical system 80 includes at least a first light source 82 and a detector 84 spaced apart from the first light source. The first light source 82 may be configured to pass light through a first measurement zone of the cassette 20 when the cassette is inserted into the analyzer 100. The first detector 84 may be positioned opposite the first light source 82 to detect the amount of light that passes through the first measurement zone of the cassette 20. As shown illustratively in FIGS. 11 and 12, in one embodiment, the optical system includes ten light sources and ten detectors. It should be appreciated that in other embodiments, the number of light sources and detectors may vary as the invention is not so limited. As mentioned above, the cassette 20 may include a plurality of measurement zones 209 and the cassette 20 may be positioned within the analyzer such that each measurement zone 209 aligns with a light source and corresponding detector. In some embodiments, the light source includes an optical aperture 83 (FIG. 11) which may help direct light from the light source to a particular region within a measurement zone of the cassette.

In one embodiment, the light sources are light emitting diodes (LED's) or laser diodes. For example, an InGaAlP red semiconductor laser diode emitting at 654 nm may be used. Other light sources can also be used. The light source, e.g., as shown illustratively in FIG. 14, may be positioned within a nest or housing 90. The nest or housing 90 may include a narrow aperture or thin tube 92 that may assist in collimating light. As shown, the light sources may be positioned above where the cassette 20 is inserted into the analyzer such that the light source shines down onto the top surface of the cassette 20. Other suitable configurations of the light source with respect to the cassette are also possible.

It should be appreciated that the wavelength of the light sources may vary as the invention is not so limited. For example, in one embodiment, the wavelength of the light source is approximately 670 nm, and in another embodiment, the wavelength of the light source is approximately 650 nm. It should be appreciated that in one embodiment, the wavelength of each light source may be different such that each measurement zone 209 of the cassette receives a different light wavelength. In one particular embodiment when measuring hemocrit or hemoglobin, an isobestic wavelength range between approximately 590 nm and approximately 805 nm may be used for at least one of the measurement zones.

As mentioned, a detector 84 may be spaced apart from and positioned below a light source 82 to detect the amount of light that passes through the cassette. In one embodiment, one or more of the detectors are photodetectors (e.g., photodiodes). In certain embodiments, the photodetector may be any suitable device capable of detecting the transmission of light that is emitted by the light source. One type of photodetector is an optical integrated circuit (IC) including a photodiode having a peak sensitivity at 700 nm, an amplifier and a voltage regulator. The detector, e.g., as shown in FIG. 14, may be positioned within a nest or housing 94 which may include a narrow aperture or thin tube 96 to ensure that only light from the center of the measurement zone 209 is measured at the detector 84. As described in more detail below, if the light source is pulse modulated, the photodetector may include a filter to remove the effect of light that is not at the selected frequency. When multiple and neighboring signals are detected at the same time, the light source used for each measurement zone (e.g., detection region) can be modulated at a frequency sufficiently different from that of its neighboring light source. In this configuration, the each detector can be configured (e.g., using software) to select for its attributed light source, thereby avoiding interfering light form neighboring optical pairs.

As described herein, a cassette may include a measurement zone which includes a meandering channel configured and arranged to align with a detector such that upon alignment, the detector can measure a single signal through more than one adjacent segment of the meandering channel. In some embodiments, the detector is able to detect a signal within at least a portion of the area of the meandering channel and through more than one segment of the meandering channel such that a first portion of the signal, measured from a first segment of the meandering channel, is similar to a second portion of the signal, measured from a second segment of the meandering channel. In such embodiments, because the signal is present as a part of more than one segment of the meandering channel, there is no need for precise alignment between a detector and a measurement zone.

The positioning of the detector over the measurement zone (e.g., a meandering region) without the need for precision is an advantage, since external (and possibly, expensive) equipment such as microscopes, lenses, and alignment stages are not required (although they may be used in certain embodiments). Instead, alignment may be performed by low-cost methods that do not necessarily require an active or separate alignment step by the user. For example, in one embodiment, a cassette comprising a meandering region can be placed in a slot of an analyzer described herein (e.g., in a cavity having the same or similar shape as the cassette), and the measurement zone can be automatically located in a beam of light of the detector. Possible causes of misalignment caused by, for instance, cassette-to-cassette variations, the exact location of the cassette in the slot, and normal usage of the cassette, may be negligible compared to the dimensions of the measurement zone. As a result, the meandering region can stay within the beam of light and detection is not interrupted due to these variations.

The detector may detect a signal within all, or a portion, of a measurement zone (e.g., including a meandering region). In other words, different amounts of the meandering region may be used as an optical detection pathway. For instance, the detector may detect a signal within at least 15% of the measurement zone, at least 20% of the measurement zone, at least 25% of the measurement zone, within at least 50% of the measurement zone, or within at least 75% of the measurement zone (but less than 100% of the measurement zone). The area in which the measurement zone is used as an optical detection pathway may also depend on, for instance, the opacity of the material in which the channel is fabricated (e.g., whether all, or, a portion, of the channel is transparent), the amount of a non-transparent material that may cover a portion of the channel (e.g., via use of a protective cover), and/or the size of the detector and the measurement zone.

In one embodiment, a signal produced by a reaction carried out in the cassette is homogenous over the entire measurement zone (e.g., over an entire meandering channel region). That is, the measurement zone (e.g., meandering channel region) may allow production and/or detection of a single, homogenous signal in said region upon carrying out a chemical and/or biological reaction (e.g., and upon detection by a detector). Prior to carrying out a reaction in the meandering channel region, the meandering channel may include, for example, a single species (and concentration of species) to be detected/determined. The species may be adsorbed to a surface of the meandering channel. In another embodiment, the signal may be homogeneous over only portions of the meandering region, and one or more detectors may detect different signals within each of the portions. In certain instances, more than one measurement zone can be connected in series and each measurement zone can be used to detect/determine a different species. It should be understood that while meandering regions are described, measurement zones that do not include meandering regions can also be used.

Applicant has recognized that the amount of light transmitted through a measurement zone of the cassette may be used to determine information about not only the sample, but also information about specific processes occurring in the fluidic system of the cassette (e.g., mixing of reagents, flow rate, etc.). In some cases, measurement of light through a region can be used as feedback to control fluid flow in the system. In certain embodiments, quality control or abnormalities in the operation of the cassette can be determined. For example, feedback from a measurement zone to a control system can be used to determine abnormalities that have occurred in the microfluidic system, and the control system may send a signal to one or more components to cause all or portions of the system to shut down. Consequently, the quality of the processes being performed in the microfluidic system can be controlled using the systems and methods described herein. A more detailed discussion of such and other processes may be found below and in a U.S. Provisional Patent Application No. 61/325,023, filed Apr. 16, 2010 and entitled "Feedback Control in Microfluidic Systems", which is herein incorporated by reference in its entirety.

It should be recognized that a clear liquid (such as water) may allow a large amount of light to be transmitted from the light source 82, through the measurement zone 209 and to the detector 84. Air within the measurement zone 209 may lead to less light transmitted through the measurement zone 209 because more light may scatter within the channel compared to when a clear liquid is present. When a blood sample is in a measurement zone 209, a significantly less amount of light may pass through to the detector 84 due to the light scattering off of blood cells and also due to absorbance. In one embodiment, silver associates with a sample component bound to a surface within the measurement zone and as silver builds up within the measurement zone 209, less and less light is transmitted through the measurement zone 209.

It is recognized that measuring the amount of light that is detected at each detector 84 enables a user to determine which reagents are in a particular measurement zone 209 at a particular point in time. It is also recognized that by measuring the amount of light that is detected with each detector 84, it is possible to measure the amount of silver deposited in each measurement zone 209. This amount may correspond to the amount of analyte captured during a reaction which may thus provide a measure of the concentration of the analyte in the sample.

As noted above, Applicant has recognized that the optical system 80 may be used for a variety of quality control reasons. First, the time it takes for a sample to reach a measurement zone where the optical system detects the light that passes though the measurement zone may be used to determine whether there is a leak or clog in the system. Also, when the sample is expected to be a certain volume, for example, approximately 10 microliters, there is an expected flow time which would be associated for the sample to pass through the channels and measurement zones. If the sample falls outside of that expected flow time, it could be an indication that there is not enough sample to conduct the analysis and/or that the wrong type of sample was loaded into the analyzer. Additionally, an expected range of results may be determined based upon the type of sample (e.g., serum, blood, urine, etc.) and if the sample is outside of the expected range, it could be an indication of an error.

In one embodiment, the optical system 80 includes a plurality of light sources 82, 86 and a plurality of corresponding detectors 84, 88. As shown illustratively in FIGS. 11-13, in one embodiment, a first light source 82 is adjacent a second light source 86, where the first light source 82 is configured to pass light though a first measurement zone of the cassette 20 and the second light source is configured to pass light through a second measurement zone of the cassette 20. In one embodiment, the light sources are configured such that the second light source 86 is not activated unless the first light source 82 is deactivated. Applicant has recognized that some light from one light source may spread over to an adjacent detector and may affect the amount of light detected at the adjacent detector. In one set of embodiments, if the adjacent light source is activated at the same time as the first light source, then both detectors 84, 88 are also measuring the amount of light that passes through the first and second measurement zones of the cassette at the same time, which may lead to inaccurate measurements.

Thus, in one set of embodiments, the plurality of light sources are configured to activate sequentially with only one light source activated at a time. The corresponding detector for the activated light source is thus only detecting the amount of light that passes through the corresponding measurement zone 209. In one particular embodiment, the light sources are configured to each activate for a short period of time (e.g., at least approximately 500, 250, 100, or 50 microseconds, or, in some embodiments, less than or equal to approximately 500, 250, 100, or 50 microseconds), and then an adjacent light source is configured to activate for a similar time frame. Activation for 100 microseconds corresponds to a rate of 10 kHz. In one embodiment, a multiplexed analog to digital converter is used to pulse the light and measure the amount of light detected at each corresponding detector every 500, 250, 100, or 50 microseconds. Pulsing the light in this manner may help to prevent stray light passing through one measurement zone to alter the amount of light detected that passes through an adjacent measurement zone.

Although there may be some benefits associated with pulsing the light sources in the manner described above, it should be recognized that the invention is not so limited and that other arrangements may be possible, such as where multiple light sources may be activated at the same time. For example, in one embodiment, light sources that are not directly adjacent to one another can be activated substantially simultaneously.

Figure 17:
FIGS. 17-21 are schematic views of a user interface of a sample analyzer according to one embodiment.

Referring to FIG. 17, in one embodiment, the analyzer 100 includes a temperature regulating system positioned within the housing 101 which may be configured to regulate the temperature within the analyzer. For certain sample analysis, the sample may need to be kept within a certain temperature range. For example, in one embodiment, it is desirable to maintain the temperature within the analyzer 100 at approximately 37° C. Accordingly, in one embodiment, the temperature regulating system includes a heater 140 configured to heat the cassette 20. In one embodiment, the heater 140 is a resistive heater which may be positioned on the underside of where the cassette 20 is placed in the analyzer 100. In one embodiment, the temperature regulating system also includes a thermistor 142 to measure the temperature of the cassette 20 and a controller circuit may be provided to control the temperature.

In one embodiment, the passive flow of air within the analyzer may act to cool the air within the analyzer if needed. A fan (not shown) may optionally be provided in the analyzer 100 to lower the temperature within the analyzer 100. In some embodiments, the temperature regulating system may include Peltier thermoelectric heaters and/or coolers within the analyzer.

In certain embodiments, an identification system including one or more identifiers is used and associated with one or more components or materials associated with a cassette and/or analyzer. The "identifiers," as described in greater detail below, may themselves be "encoded with" information (i.e. carry or contain information, such as by use of an information carrying, storing, generating, or conveying device such as a radio frequency identification (RFID) tag or bar code) about the component including the identifier, or may not themselves be encoded with information about the component, but rather may only be associated with information that may be contained in, for example, a database on a computer or on a computer readable medium (e.g., information about a user, and/or sample to be analyzed). In the latter instance, detection of such an identifier can trigger retrieval and usage of the associated information from the database.

Identifiers "encoded with" information about a component need not necessarily be encoded with a complete set of information about the component. For example, in certain embodiments, an identifier may be encoded with information merely sufficient to enable a unique identification of the cassette (e.g. relating to a serial no., part no., etc.), while additional information relating to the cassette (e.g. type, use (e.g., type of assay), ownership, location, position, connectivity, contents, etc.) may be stored remotely and be only associated with the identifier.

"Information about" or "information associated with" a cassette, material, or component, etc. is information regarding the identity, positioning, or location of the cassette, material or component or the identity, positioning, or location of the contents of a cassette, material or component and may additionally include information regarding the nature, state or composition of the cassette, material, component or contents. "Information about" or "information associated with" a cassette, material or component or its contents can include information identifying the cassette, material or component or its contents and distinguishing the cassette, material, component or its contents from others. For example, "information about" or "information associated with" a cassette, material or component or its contents may refer to information indicating the type or what the cassette, material or component or its contents is, where it is or should be located, how it is or should be positioned, the function or purpose of the cassette, material or component or its contents, how the cassette, material or component or its contents is to be connected with other components of the system, the lot number, origin, calibration information, expiration date, destination, manufacturer or ownership of the cassette, material or component or its contents, the type of analysis/assay to be performed in the cassette, information about whether the cassette has been used/analyzed, etc.

In one set of embodiments, an identifier is associated with a cassette and/or analyzer described herein. In general, as used herein, the term "identifier" refers to an item capable of providing information about the cassette and/or analyzer (e.g. information including one or more of identity, location, or position/positioning of the cassette and/or analyzer or a component thereof) with which the identifier is associated or installed into, or capable of being identified or detected and the identification or detection event being associated with information about the cassette and/or analyzer with which the identifier is associated. Non-limiting examples of identifiers that may be used in the context of the invention include radio frequency identification (RFID) tags, bar codes, serial numbers, color tags, fluorescent or optical tags (e.g., using quantum dots), chemical compounds, radio tags, magnetic tags, among others.

Figure 16:
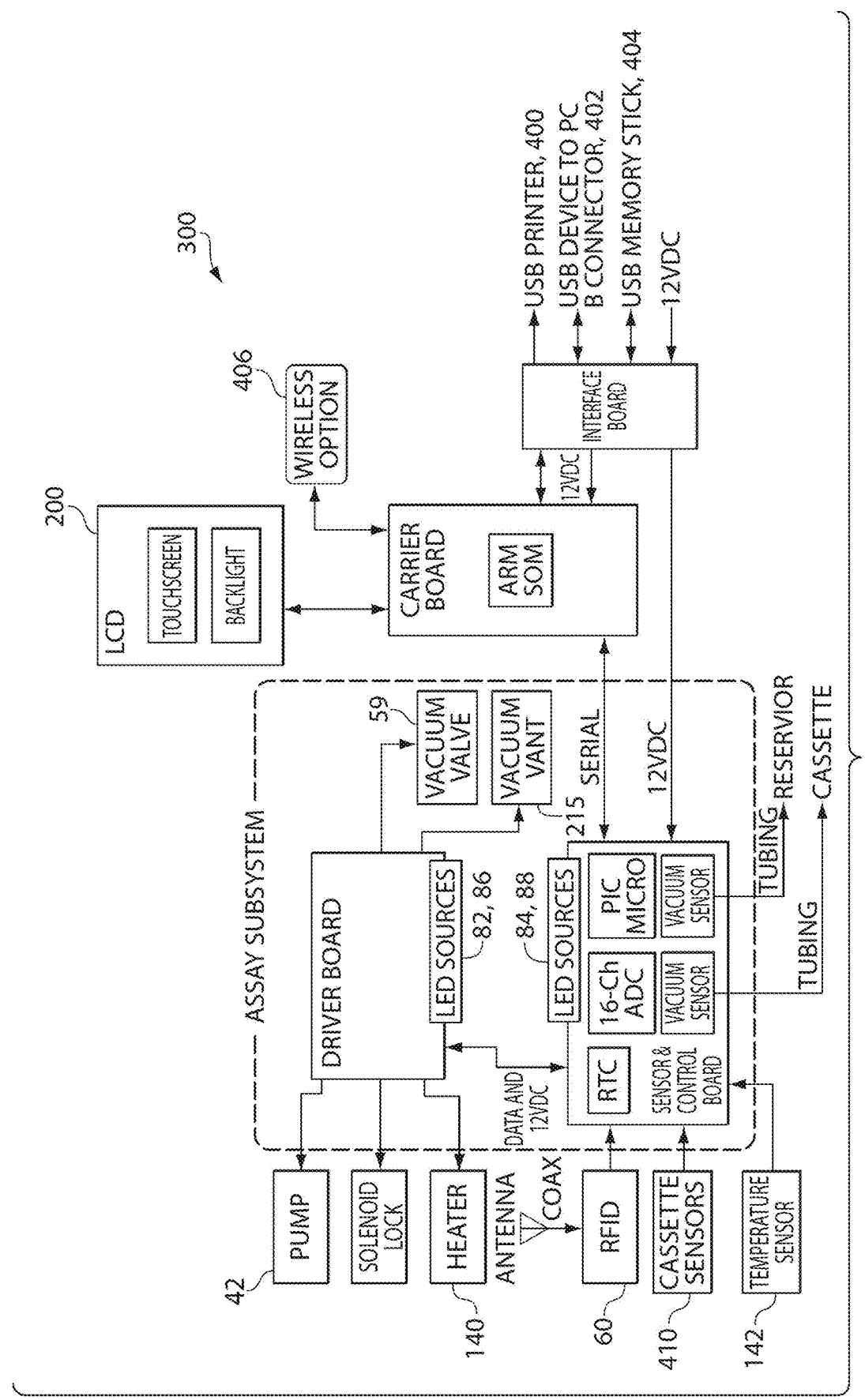
FIG. 16 is a block diagram showing a control system of a sample analyzer associated with a variety of different components according to one embodiment.

In one embodiment, as shown illustratively in FIG. 16, the analyzer 100 includes an identification reader 60 positioned within the housing 101 configured to read information about with the cassette 20. Any suitable identification reader that can be used to read information from an identifier. Non-limiting examples of identification readers include RFID readers, bar code scanners, chemical detectors, cameras, radiation detectors, magnetic or electric field detectors, among others. The method of detection/reading and appropriate type of identification detector depends on the particular identifier utilized and can include, for example, optical imaging, fluorescence excitation and detection, mass spectrometry, nuclear magnetic resonance, sequencing, hybridization, electrophoresis, spectroscopy, microscopy, etc. In some embodiments, the identification readers may be mounted or pre-embedded in specific locations (e.g., on or within a cassette and/or analyzer).

In one embodiment, the identification reader 60 is an RFID reader configured to read an RFID identifier associated with the cassette 20. For example, as shown illustratively in FIG. 2, in one embodiment, the analyzer 100 includes an RFID module and antenna that are configured to read information from the cassette 20 inserted into the analyzer 100. In another embodiment, the identification reader 60 is a barcode reader configured to read a barcode associated with the cassette 20. Once the cassette 20 is inserted into the analyzer 100, the identification reader 60 may read the information from the cassette 20. The identifier on the cassette may include one or more of the types of information such as cassette type, type of analysis/assay to be performed, lot number, information about whether the cassette has been used/analyzed, and other information described herein. The reader 60 may also be configured to read information provided with a group of cassettes, such as in a box of cassettes, such as, but not limited to calibration information, expiration date, and any additional information specific to that lot. The information identified may be optionally displayed to a user, e.g., to confirm that a correct cassette and/or type of assay is being performed.

In some cases, the identification reader may be integrated with a control system via communication pathways. Communication between the identification readers and the control system may occur along a hard-wired network or may be transmitted wirelessly. In one embodiment, the control system can be programmed to recognize a specific identifier (e.g., of a cassette associated with information relating to a cassette type, manufacturer, assay to be performed, etc.) as indicating the cassette is suitably connected or inserted within a particular type of analyzer.

In one embodiment, the identifier of a cassette be associated with predetermined or programmed information contained in a database regarding the use of the system or cassette for a particular purpose, user or product, or with particular reaction conditions, sample types, reagents, users, and the like. If an incorrect match is detected or an identifier has been deactivated, the process may be halted or the system may be rendered not operable until the user has been notified, or upon acknowledgement by a user.

The information from or associated with an identifier can, in some embodiments, be stored, for example in computer memory or on a computer readable medium, for future reference and record-keeping purposes. For example, certain control systems may employ information from or associated with identifiers to identify which components (e.g., cassettes) or type of cassettes were used in a particular analysis, the date, time, and duration of use, the conditions of use, etc. Such information may be used, for example, to determine whether one or more components of the analyzer should be cleaned or replaced. Optionally, a control system or any other suitable system could generate a report from gathered information, including information encoded by or associated with the identifiers, that may be used in providing proof of compliance with regulatory standards or verification of quality control.

Information encoded on or associated with an identifier may also be used, for example, to determine whether the component associated with the identifier (e.g., a cassette) is authentic or counterfeit. In some embodiments, the determination of the presence of a counterfeit component causes system lockout. In one example, the identifier may contain a unique identity code. In this example, the process control software or analyzer would not permit system startup (e.g., the system may be disabled) if a foreign or mismatched identity code (or no identity code) was detected.

In certain embodiments, the information obtained from or associated with an identifier can be used to verify the identity of a customer to whom the cassette and/or analyzer is sold or for whom a biological, chemical, or pharmaceutical process is to be performed. In some cases, the information obtained from or associated with an identifier is used as part of a process of gathering data for troubleshooting a system. The identifier may also contain or be associated with information such as batch histories, assembly process and instrumentation diagrams (P and IDs), troubleshooting histories, among others. Troubleshooting a system may be accomplished, in some cases, via remote access or include the use of diagnostic software.

In one embodiment, the analyzer 100 includes a user interface 200, which may be positioned within the housing 101 and configured for a user to input information into the sample analyzer 100. In one embodiment, the user interface 200 is a touch screen, which is illustrated in FIG. 1 and FIGS. 16-21.

Figure 18:
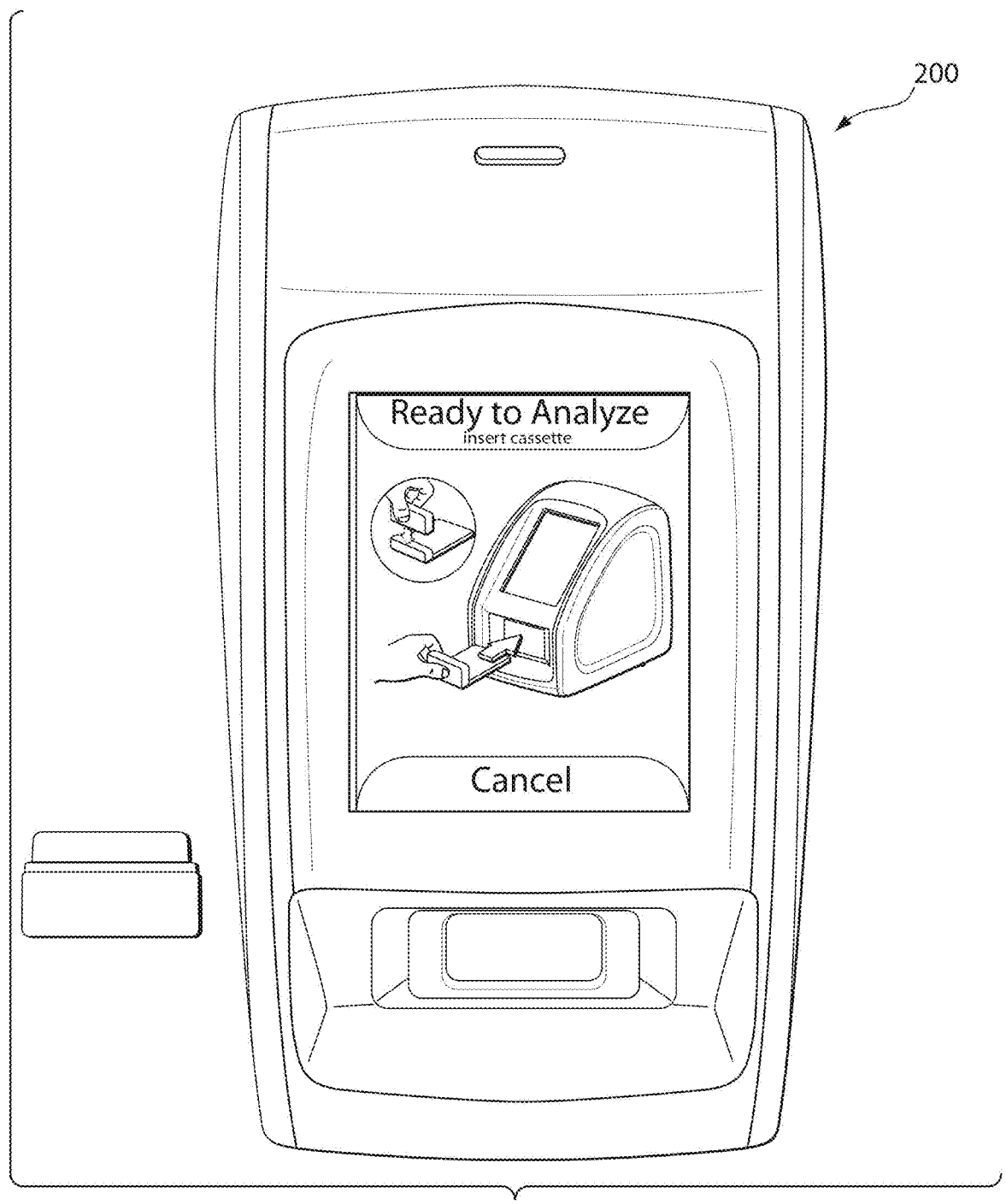
Figure 19:
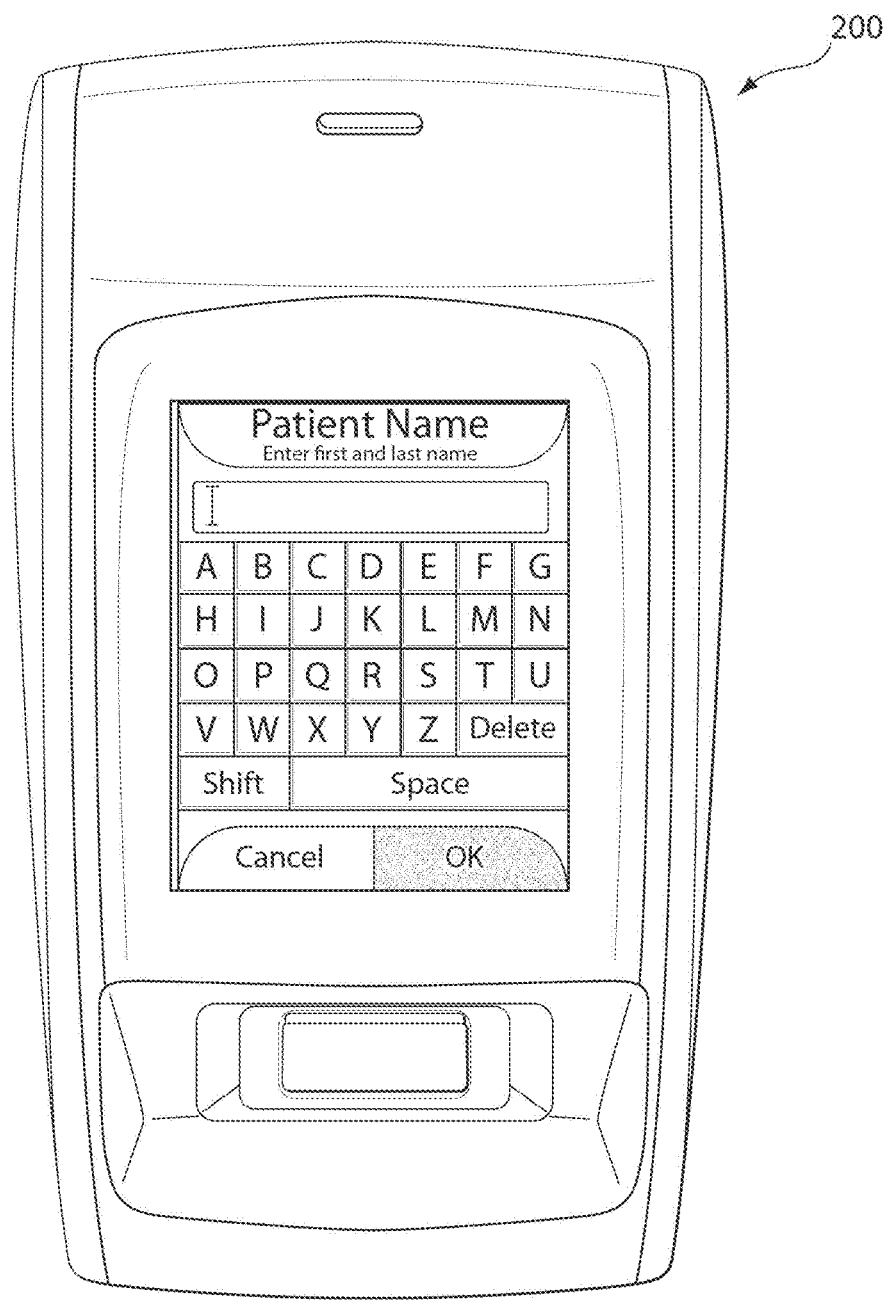
Figure 20:
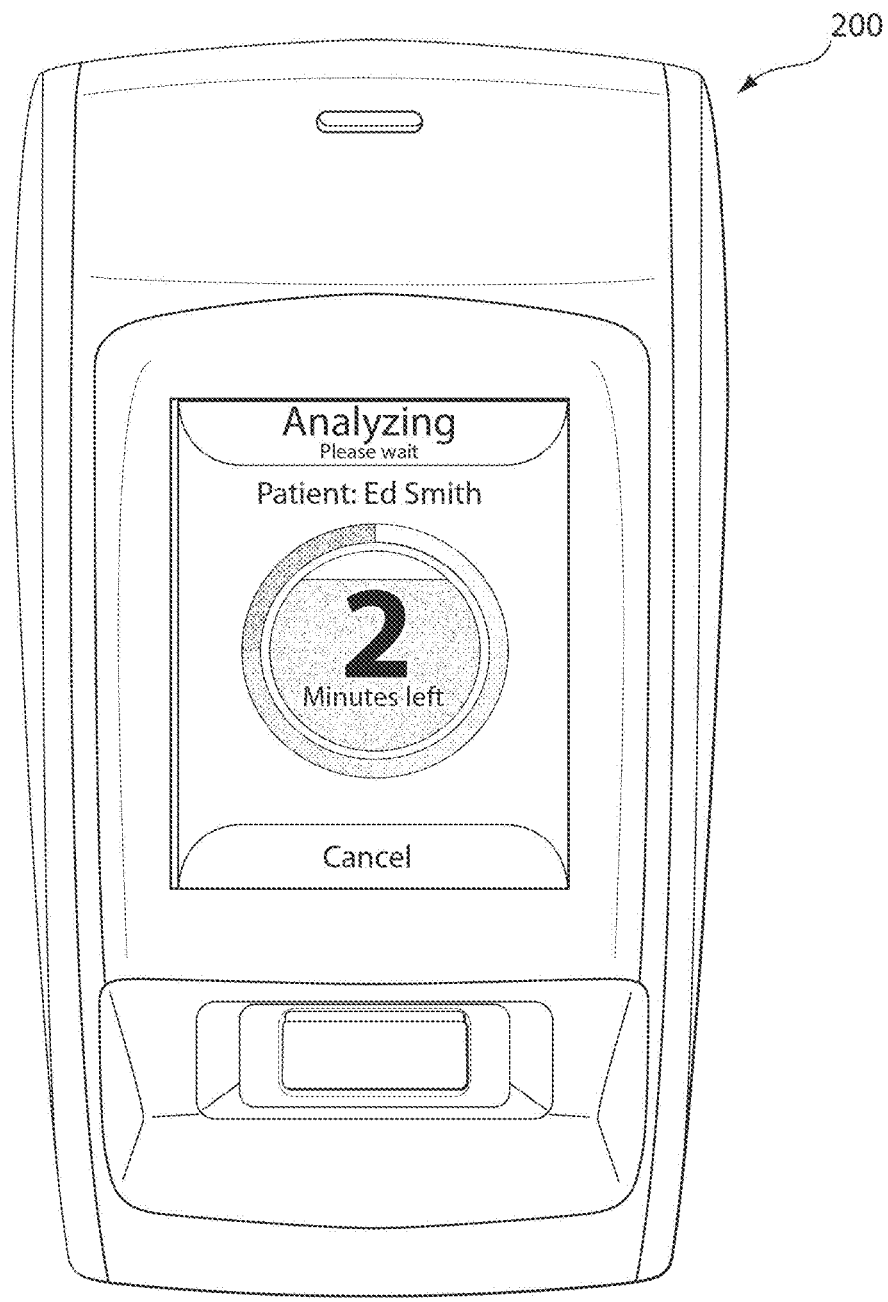
Figure 21:

As set forth in FIGS. 16-21, the touch screen may guide a user through the operation of the analyzer 100, providing text and/or graphical instructions for use of the analyzer 100. FIG. 17 illustrates one example of the graphics for the touch screen user interface 200 at the beginning of the sample analysis process. FIG. 18 illustrates one example of the graphics for the touch screen user interface 200 which guides the user to insert the cassette 20 into the analyzer 100. FIG. 19 illustrates one example of the graphics for the touch screen user interface 200 which guides the user to input the patient's name or other patient identification source/number into the analyzer 100. It should be appreciated that the patient information such as name, date of birth, and/or patient ID number may be inputted into the touch screen user interface to identify the patient. FIG. 20 illustrates one example of the graphics for the touch screen user interface 200 while the sample is being analyzed. As shown, the touch screen may indicate the amount of time remaining to complete the analysis of the sample. Finally, FIG. 21 illustrates one example of the graphics for the touch screen user interface 200 which illustrates the results of the sample analysis along with the patient's name or other identifying information.

In another embodiment, the user interface may be configured differently, such as with an LCD display and a single button scroll through menu. In another embodiment, the user interface may simply include a start button to activate the analyzer. In other embodiments, the user interface from separate independent devices (such as a smart phone or mobile computer) can be used to interface with the analyzer.

The above-described analyzer 100 may be used in a variety of ways to process and analyze a sample placed within the analyzer. In one particular embodiment, once the mechanical component 121 configured to interface with the cassette indicates that the cassette 20 is properly loaded in the analyzer 100, the identification reader 60 reads and identifies information associated with the cassette 20. The analyzer 100 may be configured to compare the information to data stored in a control system to ensure that it has calibration information for this particular sample. In the event that the analyzer does not have the proper calibration information, the analyzer may output a request to the user to upload the specific information needed. The analyzer may also be configured to review expiration date information associated with the cassette and cancel the analysis if the expiration date has passed.

In one embodiment, once the analyzer 100 has determined that the cassette 20 may be analyzed, a fluid flow source such as the vacuum manifold 48 may be configured to contact the cassette 20 to ensure an airtight seal around the vacuum port 219 and vent ports 215. In one embodiment, the optical system 80 may take initial measurements to obtain reference readings. Such reference readings may be taken both with the light sources 82, 86 activated and deactivated.

To initiate movement of the sample, the vacuum system 40 may be activated, which may rapidly change the pressure within the channel 206, 207 (e.g., reduced to approximately –30 kPa). This reduction of pressure within the channel may drive the sample into the channel 206 and through each of the measurement zones 209A-209D (see FIG. 8). After the sample reaches the final measurement zone 209D, the sample may continue to flow into the liquid containment region 217.

In one particular embodiment, the microfluidic sample analyzer 100 is used to measure the level of a prostate specific antigen (PSA) in a blood sample. In this embodiment, four measurement zones 209A-209D may be utilized to analyze the sample. For example, in a first measurement zone, the walls of the channel may be blocked with a blocking protein (such as Bovine Serum Albumin) such that little or no proteins in the blood sample attach to the walls of the measurement zone 209 (except for perhaps some non-specific binding which may be washed off). This first measurement zone may act as a negative control.

In a second measurement zone 209, the walls of the channel 206 may be coated with a predetermined large quantity of a prostate specific antigen (PSA) to act as a high or positive control. As the blood sample passes through the second measurement zone 209, little or no PSA proteins in the blood may bind to the walls of the channel. Gold conjugated signal antibodies in the sample may be dissolved from inside of the fluidic connector tube 222 or may be flowed from any other suitable location. These antibodies may not yet be bound to the PSA in the sample, and thus they may bind to the PSA on the walls of the channel to act as a high or positive control.

In a third measurement zone 209, the walls of the channel 206 may be coated with a predetermined small quantity of PSA to act as a low control. As the blood sample flows through this measurement zone 209, no PSA proteins in the sample bind to the wall of the channel. Gold conjugated signal antibodies in the sample may be dissolved from inside of the fluidic connector tube 222 (which are not yet bound to the PSA in the sample) or may be flowed from any other suitable location, and may bind to the PSA on the walls of the channel to act as a low control.

In a fourth measurement zone 209, the walls of the channel 206 may be coated with the capture antibody, an anti-PSA antibody, which binds to a different epitope on the PSA protein than the gold conjugated signal antibody. As the blood sample flows through the fourth measurement zone, PSA proteins in the blood sample may bind to the anti-PSA antibody in a way that is proportional to the concentration of these proteins in the blood. Thus, in one embodiment, the first three measurement zones 209 may act as controls and the fourth measurement zone 209 may actually test the sample. In other embodiments, different numbers of measurement zones can be provided, and an analysis may optionally include more than one measurement zones that actually test the sample.

In some instances, measurements from a region that analyzes the sample (e.g., the fourth measurement zone described above) can be used not only to determine the concentration of an analyte in a sample, but also as a control as well. For example, a threshold measurement can be established at an early phase of amplification. Measurements above this value (or below this value) may indicate that the concentration of analyte is outside the desired range for the assay. This technique may be used to identify, for example, whether a High Dose Hook Effect is taking place during the analysis, i.e., when a very high concentration of analyte gives an artificially low reading.

In other embodiments, different numbers of measurement zones can be provided, and an analysis may optionally include more than one measurement zones that actually test the sample. Additional measurement zones can be used to measure additional analytes so that the system can perform multiplex assays simultaneously with a single sample.

In one particular embodiment, it takes approximately eight minutes for a 10 microliter blood sample to flow through the four measurement zones 209. The start of this analysis may be calculated when the pressure within the channel 206 is approximately –30 kPa. During this time, the optical system 80 is measuring the light transmission for each measurement zone, and in one embodiment, this data may be transmitted to a control system approximately every 0.1 seconds. Using reference values, these measurements may be converted using the following formulas:

$$\text{Transmission} = (l - ld)/(lr - ld) \quad (1)$$

Where:
l = the intensity of transmitted light through a measurement zone at a given point in time
ld = the intensity of transmitted light through a measurement zone with the light source off
lr = a reference intensity (i.e. the intensity of the transmitted light at a measurement zone with the light source activated, or before the start of an analysis when only air is in the channel and $$\text{Optical Density} = -\log(\text{Transmission}) \quad (2)$$

Thus, using these formulas, the optical density in a measurement zone 209 may be calculated.

As described herein, a variety of methods can be used to control fluid flow in a cassette, including the use of pumps, vacuums, valves, and other components associated with an analyzer. In some cases, fluid control can also be performed at least in part by one or more components within the cassette, such as by using a valve positioned within the cassette, or the use of specific fluids and channel configurations with the cassette. In one set of embodiments, control of fluid flow can be achieved based at least in part on the influence of channel geometry and the viscosity of one or more fluids (which may be stored) inside the cassette.

One method includes flowing a plug of a low viscosity fluid and a plug of a high viscosity fluid in a channel including a flow constriction region and a non-constriction region. In one embodiment, the low viscosity fluid flows at a first flow rate in the channel and the flow rate is not substantially affected by the fluid flowing in the flow constriction region. When the high viscosity fluid flows from the non-constriction region to the flow constriction region, the flow rates of the fluids decrease substantially, since the flow rates, in some systems, are influenced by the highest viscosity fluid flowing in the smallest cross-sectional area of the system (e.g., the flow constriction region). This causes the low viscosity fluid to flow at a second, slower flow rate than its original flow rate, e.g., at the same flow rate at which the high viscosity fluid flows in the flow constriction region.

For example, one method of controlling fluid flow may involve flowing a first fluid from a first channel portion to a second channel portion in a microfluidic system, wherein a fluid path defined by the first channel portion has a larger cross-sectional area than a cross-sectional area of a fluid path defined by the second channel portion, and flowing a second fluid in a third channel portion in the microfluidic system in fluid communication with the first and second channel portions, wherein the viscosity of the first fluid is different than the viscosity of the second fluid, and wherein the first and second fluids are substantially incompressible. Without stopping the first or second fluids, a volumetric flow rate of the first and second fluids may be decreased by a factor of at least 3, at least 10, at least 20, at least 30, at least 40, or at least 50 in the microfluidic system as a result of the first fluid flowing from the first channel portion to the second channel portion, compared to the absence of flowing the first fluid from the first channel portion to the second channel portion. A chemical and/or biological interaction involving a component of the first or second fluids may take place at a first measurement zone in fluid communication with the channel portions while the first and second fluids are flowing at the decreased flow rate.

Accordingly, by designing microfluidic systems with flow constriction regions positioned at particular locations and by choosing appropriate viscosities of fluids, a fluid can be made to speed up or slow down at different locations within the system without the use of valves and/or without external control. In addition, the length of the channel portions can be chosen to allow a fluid to remain in a particular area of the system for a certain period of time. Such systems are particularly useful for performing chemical and/or biological assays, as well as other applications in which timing of reagents is important. Non-limiting examples of methods and configurations of channels for controlling fluid flow are described in more detail in U.S. patent application Ser. No. 12/428,372, filed Apr. 22, 2009, published as U.S. Patent Publication No. 2009/0266421, entitled "Flow Control in Microfluidic Systems", which is incorporated herein by reference in its entirety for all purposes.

FIG. 16 is a block diagram 300 that illustrates how a control system 305 (see FIG. 13) may be operatively associated with a variety of different components according to one embodiment. Control systems described herein can be implemented in numerous ways, such as with dedicated hardware or firmware, using a processor that is programmed using microcode or software to perform the functions recited above or any suitable combination of the foregoing. A control system may control one or more operations of a single analysis (e.g., for a biological, biochemical or chemical reaction), or of multiple (separate or interconnected) analyses. As shown illustratively in FIG. 13, the control system 305 may be positioned within the housing 101 of the analyzer and may be configured to communicate with the identification reader 60, the user interface 200, the fluid flow source 40, the optical system 80, and/or the temperature regulating system to analyze a sample in the cassette.

In one embodiment, the control system includes at least two processors, including a real time processor that controls and monitors all of the sub-systems which directly interface with the cassette. In one embodiment, at a particular time interval (e.g., every 0.1 seconds), this processor communicates with a second higher level processor which communicates with the user through the user interface and/or the communication subsystem (discussed below) and directs the operation of the analyzer (e.g., determines when to start analyzing a sample and interprets the results). In one embodiment, communication between these two processors occurs through a serial communication bus. It should be appreciated that in another embodiment, the analyzer may only include one processor, or more than two processors, as the invention is not so limited.

In one embodiment, the analyzer is capable of interfacing with external devices and may, for example, include ports for connection with one or more external communication units. External communication may be accomplished, for example, via USB communication. For example, as shown in FIG. 16, the analyzer may output the results of a sample analysis to a USB printer 400, or to a computer 402. Additionally, the data stream produced by the real time processor may be outputted to a computer or a USB memory stick 404. In some embodiments, a computer may be able to directly control the analyzer through a USB connection as well. Further, other types of communication options are available as the present invention is not limited in this respect. For example, Ethernet, Bluetooth and/or WI-FI communication 406 with the analyzer may be established through the processor.

The calculation methods, steps, simulations, algorithms, systems, and system elements described herein may be implemented using a computer implemented control system, such as the various embodiments of computer implemented systems described below. The methods, steps, systems, and system elements described herein are not limited in their implementation to any specific computer system described herein, as many other different machines may be used.

The computer implemented control system can be part of or coupled in operative association with a sample analyzer, and, in some embodiments, configured and/or programmed to control and adjust operational parameters of the sample analyzer, as well as analyze and calculate values, as described above. In some embodiments, the computer implemented control system can send and receive reference signals to set and/or control operating parameters of the sample analyzer and, optionally, other system apparatus. In other embodiments, the computer implemented system can be separate from and/or remotely located with respect to the sample analyzer and may be configured to receive data from one or more remote sample analyzer apparatus via indirect and/or portable means, such as via portable electronic data storage devices, such as magnetic disks, or via communication over a computer network, such as the Internet or a local intranet.

The computer implemented control system may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the computer system may be a multi-processor computer system or may include multiple computers connected over a computer network.

The computer implemented control system may include a processor, for example, a commercially available processor such as one of the series x86, Celeron and Pentium processors, available from Intel, similar devices from AMD and Cyrix, the 680X0 series microprocessors available from Motorola, and the PowerPC microprocessor from IBM. Many other processors are available, and the computer system is not limited to a particular processor.

A processor typically executes a program called an operating system, of which WindowsNT, Windows95 or 98, UNIX, Linux, DOS, VMS, MacOS and OS8 are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer implemented control system is not limited to a particular computer platform.

The computer implemented control system may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer implemented control system also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer implemented control system that implements the methods, steps, systems and system elements described above in relation to FIG. 16 is not limited thereto. The computer implemented control system is not limited to a particular memory system.

At least part of such a memory system described above may be used to store one or more data structures (e.g., look-up tables) or equations described above. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer implemented control system may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer implemented control system may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer implemented control system also may include one or more input devices. Example input devices include a keyboard, keypad, track ball, mouse, pen and tablet, communication devices such as described above, and data input devices such as audio and video capture devices and sensors. The computer implemented control system is not limited to the particular input or output devices described herein.

It should be appreciated that one or more of any type of computer implemented control system may be used to implement various embodiments described herein. Aspects of the invention may be implemented in software, hardware or firmware, or any combination thereof. The computer implemented control system may include specially programmed, special purpose hardware, for example, an application-specific integrated circuit (ASIC). Such special-purpose hardware may be configured to implement one or more of the methods, steps, simulations, algorithms, systems, and system elements described above as part of the computer implemented control system described above or as an independent component.

The computer implemented control system and components thereof may be programmable using any of a variety of one or more suitable computer programming languages. Such languages may include procedural programming languages, for example, C, Pascal, Fortran and BASIC, object-oriented languages, for example, C++, Java and Eiffel and other languages, such as a scripting language or even assembly language.

The methods, steps, simulations, algorithms, systems, and system elements may be implemented using any of a variety of suitable programming languages, including procedural programming languages, object-oriented programming languages, other languages and combinations thereof, which may be executed by such a computer system. Such methods, steps, simulations, algorithms, systems, and system elements can be implemented as separate modules of a computer program, or can be implemented individually as separate computer programs. Such modules and programs can be executed on separate computers.

Such methods, steps, simulations, algorithms, systems, and system elements, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system, or system element, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system, or system element.

It should be appreciated that various embodiments may be formed with one or more of the above-described features. The above aspects and features may be employed in any suitable combination as the present invention is not limited in this respect. It should also be appreciated that the drawings illustrate various components and features which may be incorporated into various embodiments. For simplification, some of the drawings may illustrate more than one optional feature or component. However, the invention is not limited to the specific embodiments disclosed in the drawings. It should be recognized that the invention encompasses embodiments which may include only a portion of the components illustrated in any one drawing figure, and/or may also encompass embodiments combining components illustrated in multiple different drawing figures.

EXAMPLES

The following example is intended to illustrate certain features of the present invention, but do not exemplify the full scope of the invention.

Example 1

Figure 22:
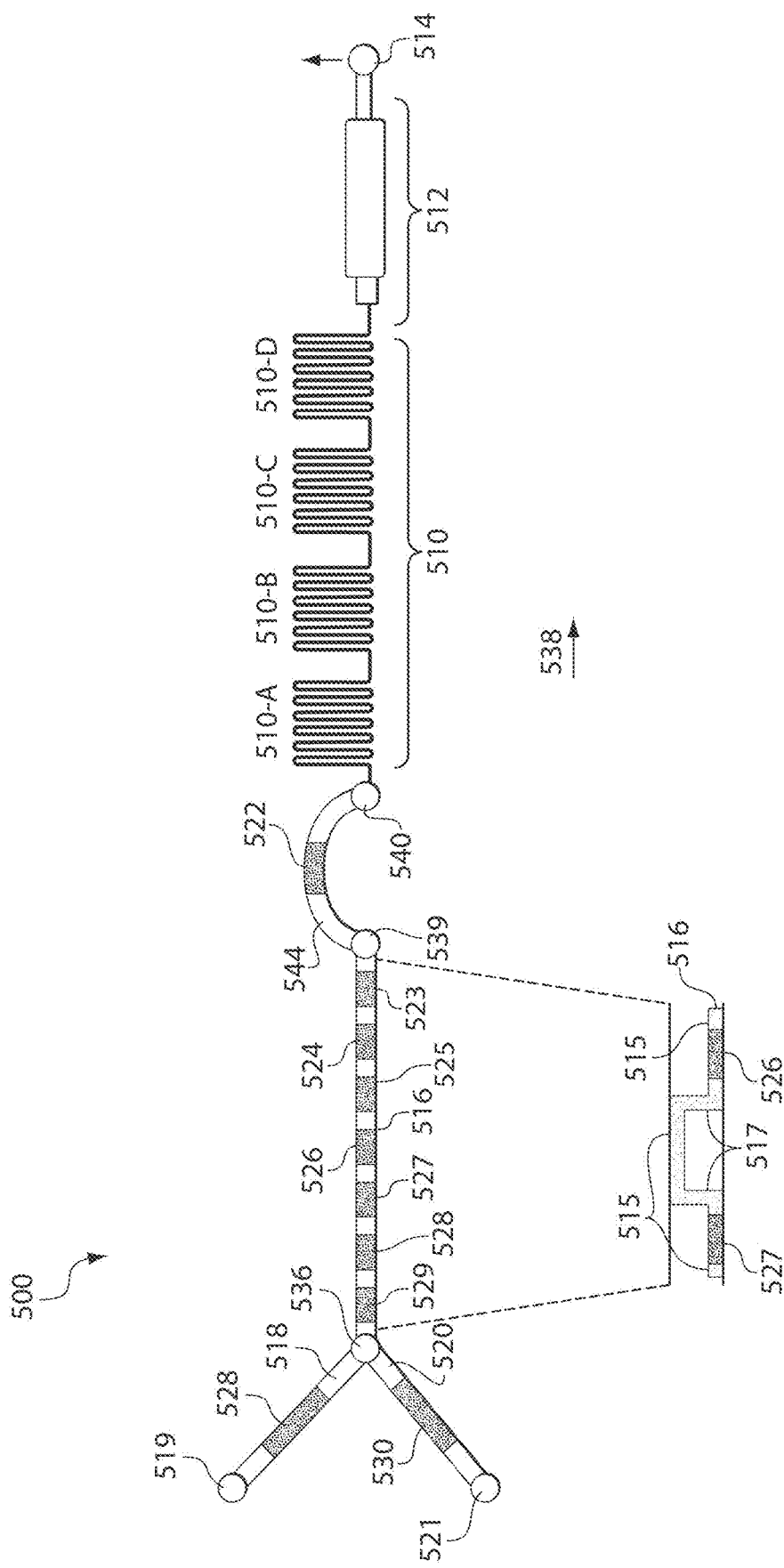
FIG. 22 is a schematic diagram showing a microfluidic system of a cassette according to one embodiment.

This example describes the use of a cassette and analyzer to perform an assay to detect PSA in a sample by electrolessly depositing silver onto gold particles that are associated with the sample. FIG. 22 includes a schematic illustration of a microfluidic system 500 of a cassette used in this example. The cassette had a similar shape to cassette 20 shown in FIG. 3. The microfluidic system used in this example is generally described in International Patent Publication No. WO2005/066613 (International Patent Application Serial No. PCT/US2004/043585), filed Dec. 20, 2004 and entitled "Assay Device and Method," which is incorporated herein by reference in its entirety for all purposes.

The microfluidic system included measurement zones 510A-510D, waste containment region 512, and an outlet 514. The measurement zones included a microfluidic channel 50 microns deep and 120 microns wide, with a total length of 175 mm. The microfluidic system also included microfluidic channel 516 and channel branches 518 and 520 (with inlets 519 and 521, respectively). Channel branches 518 and 520 were 350 microns deep and 500 microns wide. Channel 516 was formed of sub-channels 515, which were 350 microns deep and 500 microns wide located on alternating sides of the cassette, connected by through holes 517 having a diameter of approximately 500 microns. Although FIG. 22 shows that reagents were stored on a single side of the cassette, in other embodiments, reagents were stored on both sides of the cassette. Channel 516 had a total length of 390 mm, and branches 518 and 520 were each 360 mm long. Before sealing the channels, anti-PSA antibodies were attached to a surface of the microfluidic system in a segment of the measurement zone 510.

Prior to first use, the microfluidic system was loaded with liquid reagents which were stored in the cassette. A series of 7 wash plugs 523-529 (either water of buffer, approximately 2 microliters each) were loaded using a pipette into sub-channels 515 of channel 516 using the thru-holes. Each of the wash plugs was separated by plugs of air. Fluid 528, containing a solution of silver salt, was loaded into branching channel through port 519 using a pipette. Fluid 530, containing a reducing solution, was loaded into branching channel 520 through port 521. Each of the liquids shown in FIG. 9 were separated from the other liquids by plugs of air. Ports 514, 519, 521, 536, 539, and 540 were sealed with an adhesive tape that can be easily removed or pierced. As such, the liquids were stored in the microfluidic system prior to first use.

At first use, the ports 514, 519, 521, 536, 539, and 540 were unsealed by a user peeling off a tape covering the opening of the ports. A tube 544 containing lyophilized anti-PSA antibodies labeled with colloidal gold and to which 10 microliters of sample blood (522) was added, was connected to ports 539 and 540. The tube was part of a fluid connector having a shape and configuration shown in FIG. 3. This created a fluidic connection between measurement zone 510 and channel 516, which were otherwise unconnected and not in fluid communication with one another prior to first use.

The cassette including microfluidic system 500 was inserted into an opening of an analyzer (e.g., as shown in FIGS. 10, 12 and 17). The housing of the analyzer included an arm positioned within the housing that was configured to engage a cammed surface on the cassette. The arm extended at least partially into the opening in the housing such that as the cassette was inserted into the opening, the arm was pushed away from the opening into a second position allowing the cassette to enter the opening. Once the arm engaged the inwardly cammed surface of the cassette, the cassette was positioned and retained within the housing of the analyzer, and the bias of the spring prevented the cassette from slipping out of the analyzer. The analyzer senses the cassette's insertion by means of a position sensor.

An identification reader (RFID reader) positioned within the housing of the analyzer was used to read an RFID tag on the cassette which includes lot identification information. The analyzer used this identifier to match lot information (e.g., calibration information, expiration date of the cassette, verification that the cassette is new, and the type of analysis/assay to be performed in the cassette) stored in the analyzer. The user was prompted to input information about the patient (from which the sample was acquired) into the analyzer using the touch screen. After the information about the cassette was verified by the user, the control system initiated the analysis.

The control system included programmed instructions to perform the analysis. To initiate the analysis, a signal was sent to the electronics controlling a vacuum system, which was a part of the analyzer and used to provide fluid flow. A manifold with o-rings was pressed against the cassette surface by a solenoid. One port on the manifold sealed (by an o-ring) to port 536 of the microfluidic system of the cassette. This port on the manifold was connected by a tube to a simple solenoid valve (SMC V124A-6G-M5, not shown) which was open to the atmosphere. A separate vacuum port on the manifold sealed (by-o-ring) to port 514 of the microfluidic system of the cassette. A vacuum of approximately −30 kPa was applied to port 514. Throughout the analysis, the channel including measurement zone 510 positioned between ports 540 and 514 had a substantially constant non-zero pressure drop of approximately −30 kPa. Sample 522 was flowed in the direction of arrow 538 into each of measurement zones 510A-510D. As the fluid passed through the measurement zones, the PSA proteins in sample 522 were captured by anti-PSA antibodies immobilized on the measurement zone walls, as described in more detail below. The sample took about 7-8 minutes to pass through the measurement zone, after which it was captured in the waste containment region 512.

Initiation of the analysis also involved the control system sending a signal to the optical detectors, which were positioned adjacent each of measurement zones 510, to initiate detection. Each of the detectors associated with the measurement zones recorded the transmission of light through the channels of the measurement zones, as shown in a plot 600 illustrated in FIG. 10. As the sample passed by each of the measurement zones, peaks 610A-610D were produced. The peaks (and troughs) measured by the detectors are signals (or are converted to signals) that are sent to the control system which compared the measured signals to reference signals or values pre-programmed into the control system. The control system included a pre-programmed set of instructions for providing feedback to the microfluidic system based at least in part on the comparison of signals/values.

In a first measurement zone 510-A of device 500 of FIG. 22, the walls of the channel of this measurement zone were blocked with a blocking protein (Bovine Serum Albumin) prior to first use (e.g., prior to sealing the device). Little or no proteins in the blood sample attached to the walls of the measurement zone 510-A (except for perhaps some non-specific binding which may be washed off). This first measurement zone acted as a negative control.

In a second measurement zone 510-B, the walls of the channel of this measurement zone were coated with a predetermined large quantity of a prostate specific antigen (PSA) prior to first use (e.g., prior to sealing the device) to act as a high or positive control. As the blood sample passed through the second measurement zone 510-B, little or no PSA proteins in the blood bound to the walls of the channel. Gold conjugated signal antibodies in the sample may not yet be bound to the PSA in the sample, and thus they may bind to the PSA on the walls of the channel to act as a high or positive control.

In a third measurement zone 510-C, the walls of the channel of this measurement zone were coated with a predetermined low quantity of PSA prior to first use (e.g., prior to sealing the device) to act as a low control. As the blood sample flowed through this measurement zone, little or no PSA proteins in the sample bind to the wall of the channel. Gold conjugated signal antibodies in the sample may bind to the PSA on the walls of the channel to act as a low control.

In a fourth measurement zone 510-D, the walls of the channel of this measurement zone were coated with the capture antibody, an anti-PSA antibody, which binds to a different epitope on the PSA protein than the gold conjugated signal antibody. The walls were coated prior to first use (e.g., prior to sealing the device). As the blood sample flowed through the fourth measurement zone during use, PSA proteins in the blood sample bound to the anti-PSA antibody in a way that is proportional to the concentration of these proteins in the blood. Since the sample, which included PSA, also included gold-labeled anti-PSA antibodies coupled to the PSA, the PSA captured on the measurement zone walls formed a sandwich immunocomplex.

Wash fluids 523-529 followed the sample through the measurement zones 510 towards waste containment region 512 in the direction of arrow 538. As the wash fluids were passed through the measurement zones, they washed away remaining unbound sample components. Each wash plug cleaned the channels of the measurement zones, providing progressively more complete cleaning. The last wash fluid 529 (water) washed away salts that could react with silver salts (e.g., chloride, phosphate, azide).

Figure 23:
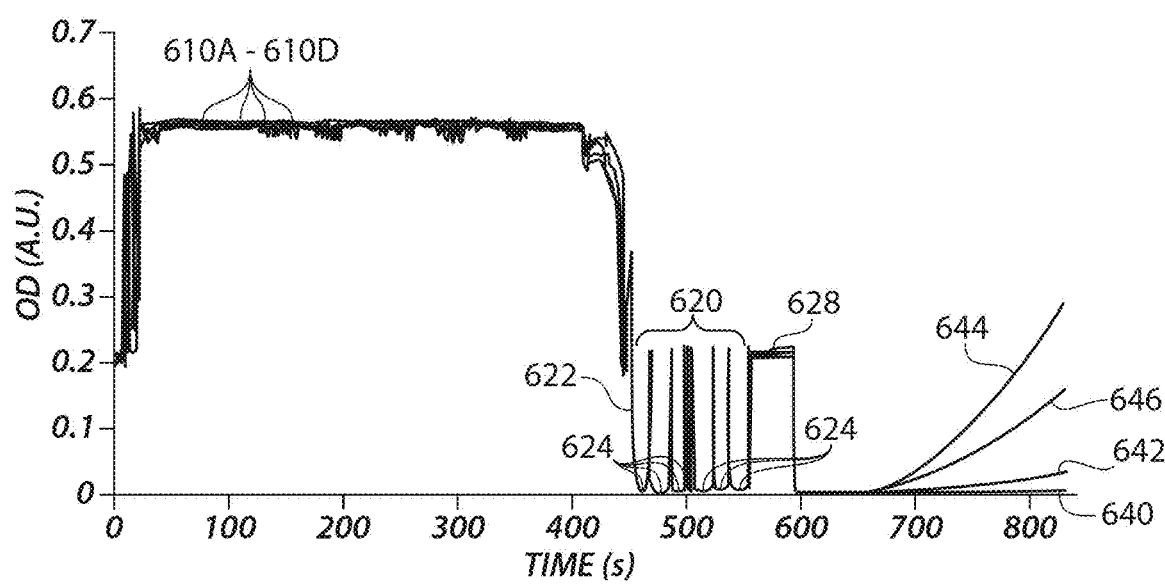
FIG. 23 is a plot showing measurement of optical density as a function of time according to one embodiment.

As shown in the plot illustrated in FIG. 23, while the wash fluids were flowing through the measurement zones, each of the detectors associated with the measurement zones measures a pattern 620 of peaks and troughs. The troughs corresponded to the wash plugs (which are clear liquids and thus provide maximum light transmission). The peaks between each plug represent the air between each plug of clear liquid. Since the assay included 7 wash plugs, 7 troughs and 7 peaks are present in plot 600. The first trough 622 is generally not as deep as the other troughs 624 since the first wash plug often catches blood cells left in the channel and thus is not completely clear.

The final peak of air 628 is much longer than the previous peaks because there were no wash plugs to follow. As a detector detects the length of this air peak, one or more signals is sent to the control system which compares the length of time of this peak to a pre-set reference signal or input value having a particular length. If the length of time of the measured peak is long enough compared to the reference signal, the control system sends a signal to the electronics controlling vent valve 536 to actuate the valve and initiate mixing of fluids 528 and 530. (Note that the signal of peak of air 628 may be combined with a signal indicating either 1) the intensity of the peak; 2) where this peak is positioned as a function of time, and/or 3) one or more signals indicating that a series of peaks 620 of particular intensity has already passed. In this way, the control system distinguishes peak of air 628 from other peaks of long duration such as peak 610 from the sample, e.g., using a pattern of signals.)

To initiate mixing, the solenoid connected by the manifold to vent port 536 is closed. Since the vacuum remains on and no air can enter through vent valve 536, air enters the device through ports 519 and 521 (which are open). This forces the two fluids 528 and 530 in the two storage channels upstream of vent valve 536 to move substantially simultaneously toward outlet 514. These reagents mix at the intersection of the channels to form an amplification reagent (a reactive silver solution) having a viscosity of about $1 \times 10^{-3}$ Pa·s. The ratio of the volumes of fluids 528 and 530 was about 1:1. The amplification reagent continued through the downstream storage channel, through tube 544, through measurement zones 510, and then to waste containment region 512. After a set amount of time (12 seconds), the analyzer reopened vent valve 536 such that air flows through vent valve 536 (instead of the vent ports). This left some reagent behind in the upstream storage channels 518 and 520 on the device. This also results in a single plug of mixed amplification reagent. The 12 seconds of vent-valve closure results in an amplification plug of approximately 50 µL. (Instead of simple timing, another way to trigger the re-opening of the vent valve would be to detect the amplification reagent as it first enters the measurement zones.)

Because the mixed amplification reagent is stable for only a few minutes (usually less than 10 minutes), the mixing was performed less than a minute before use in measurement zone 510. The amplification reagent is a clear liquid, so when it enters the measurement zones, optical density is at its lowest. As the amplification reagent passed across the measurement zones, silver was deposited on the captured gold particles to increase the size of the colloids to amplify the signal. (As noted above, gold particles were present in the low and high positive control measurement zones and, to the extent that PSA was present in the sample, in the test measurement zone.) Silver can then be deposited on top of the already deposited silver, leaving more and more silver deposited in the measurement zones. Eventually the deposited silver reduces the transmission of light through the measurement zones. The reduction in transmitted light is proportional to the amount of silver deposited and can be related to the amount of gold colloids captured on the channel walls. In a measurement zone where no silver is deposited (the negative control for example, or the test area when the sample contains none of the target protein, such as PSA), there will be no (or minimal) increase in optical density. In a measurement zone with significant silver deposition, the slope and ultimate level of the pattern of increasing optical density will be high. The analyzer monitors the pattern of this optical density during amplification in the test area to determine the concentration of analyte in the sample. In one version of the test, the pattern is monitored within the first three minutes of amplification. The optical density in each of the measurement zones as a function of time was recorded and are shown as curves 640, 644, 642, and 646 in FIG. 10. These curves corresponded to signals that were produced in measurement zones 510-A, 510-B, 510-C, and 510-D, respectively.

After three minutes of amplification, the analyzer stops the test. No more optical measurements are recorded and the manifold is disengaged from the device. The test result is displayed on the analyzer screen and communicated to a printer, computer, or whatever output the user has selected. The user may remove the device from the analyzer and throw it away. The sample and all the reagents used in the assay remain in the device. The analyzer is ready for another test.

It should be noted that the control of the flow rates of the fluids within channel 516 and the measurement zone 510 were important when flowing fluids through the system. Due to the measurement zone's relatively small cross sectional area, it served as a bottleneck, controlling the overall flow rate in the system. When the measurement zone contained liquids, the linear flow rates of the fluids in channel 516 was about 0.5 mm $s^{-1}$. Fluids flowing from branching channels 518 and 520 into main channel 516 might not have mixed reproducibly at this rate, as one fluid might have flowed faster than the other, causing unequal portions of fluids 528 and 530 to be mixed. On the other hand, when the measurement zone contained air, the linear flow rates of the fluids in channel 516 and branching channels 518 and 520 were about 15 mm $s^{-1}$. At this higher flow rate, the flow rate in branching channels 518 and 520 were equal and reproducible (when vent valve 536 was closed), producing reproducible mixing. For this reason, the valve connected to port 536 was not closed until fluid 542 passed through the measurement zone to the waste containment region. As noted above, determination of when fluid 542 had exited the measurement zone 510 was performed using an optical detector so as to measure transmission of light through part of measurement zone 510 in combination with a feedback system.

The microfluidic system shown in FIG. 22 was designed such that the volume of the channel between vent valve 536 and measurement zone 510 was larger than the expected volume of the mixed activated silver solution (i.e., the combined portion of fluids 528 and 530 which traveled into channel 516 while vent valve 536 was closed). This ensured that substantially all of the mixing took place at a relatively high linear flow rate (since no liquid, and only air, was present in the measurement zone 510 at this time), and before the activated solution reached the measurement zone. This configuration helped promote reproducible and equal mixing. For the assay described in this example, it was important to sustain a flow of the activated silver mixture within the measurement zone for a few minutes (e.g., 2 to 10 minutes).

This example shows that analysis of a sample in a microfluidic system of a cassette can be performed by using an analyzer that controls fluid flow in the cassette, and by using feedback from one or more measured signals to modulate fluid flow.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device comprising:
a first component comprising a first channel formed in a first material and including at least a first port;
a second component comprising a second channel formed in a second material and including at least a second port, the second channel comprising at least one measurement zone, wherein the measurement zone comprises a binding partner for prostate specific antigen (PSA);
a fluidic connector that can be connected to the first and second components, the fluid connector comprising a fluid path including a fluid path inlet and a fluid path outlet, wherein upon connection, the fluid path inlet fluidically connects to the first port and the fluid path outlet fluidically connects to the second port to allow fluid communication between the first and second channels, and
wherein the first and second channels are not in fluid communication with one another absent connection via the fluidic connector.

2. The device of claim 1, wherein the first channel includes at least one portion having a cross-sectional dimension greater than 200 microns.

3. The device of claim 1, wherein the first material has a water vapor permeability of less than about 5.0 g·mm/m²·d.

4. The device of claim 1, wherein the second channel includes at least one portion having a cross-sectional dimension less than 200 microns.

5. The device of claim 1, wherein the first material is different from the second material.

6. The device of claim 1, wherein both the first port and the second port are accessible from a top surface of the first component or the second component.

7. The device of claim 1, wherein the binding partner for PSA is an anti-PSA antibody.

8. The device of claim 1, wherein the binding partner for PSA is selected from the group consisting of binding partners that bind free-PSA, complexed-PSA, and pro-PSA.

9. The device of claim 1, wherein the binding partner for PSA is immobilized on one or more walls of the at least one measurement zone.

10. The device of claim 1, wherein the binding partner for PSA is configured to bind to PSA in a sample.

11. The device of claim 10, wherein the sample is whole blood, serum, or plasma.

12. The device of claim 10, wherein the binding partner for PSA is configured to bind to PSA in the sample in a way that is proportional to the amount of PSA in the sample.

13. The device of claim 10, wherein the PSA in the sample is selected from the group consisting of free-PSA, complexed-PSA, and pro-PSA.

14. The device of claim 1, wherein the second channel comprises at least four measurement zones.

15. The device of claim 1, comprising an optical system configured to measure a signal at the at least one measurement zone.

16. The device of claim 15, wherein the optical system comprises one or more detectors.

17. The device of claim 16, wherein the optical system is configured to use optical detection to detect the presence of PSA in a sample at the at least one measurement zone.

18. The device of claim 16, wherein the optical system is configured to use optical detection to detect the binding and/or non-binding of a detection antibody to a positive and/or negative control.

19. The device of claim 17, wherein the optical system is configured to measure an optical density to detect the presence of PSA in the sample at the at least one measurement zone.

20. The device of claim 1, wherein the first material and/or the second material comprises polystyrene, PMMA, or a cyclo-olefin copolymer.

* * * * *